US010859675B2

United States Patent
McMahon et al.

(10) Patent No.: US 10,859,675 B2
(45) Date of Patent: Dec. 8, 2020

(54) GESTURE RECOGNITION WITH SENSORS

(71) Applicant: RESMED SENSOR TECHNOLOGIES LIMITED, Dublin (IE)

(72) Inventors: Stephen McMahon, Dublin (IE); Emma Marie Meade, Dublin (IE); Redmond Shouldice, Dublin (IE)

(73) Assignee: ResMed Sensor Technologies Limited

( * ) Notice: Subject to any disclaimer, the term of this patent is extended or adjusted under 35 U.S.C. 154(b) by 223 days.

(21) Appl. No.: 15/562,215

(22) PCT Filed: Apr. 20, 2016

(86) PCT No.: PCT/EP2016/058806
§ 371 (c)(1),
(2) Date: Sep. 27, 2017

(87) PCT Pub. No.: WO2016/170011
PCT Pub. Date: Oct. 27, 2016

(65) Prior Publication Data
US 2018/0120420 A1      May 3, 2018

Related U.S. Application Data

(60) Provisional application No. 62/150,086, filed on Apr. 20, 2015.

(51) Int. Cl.
*G01S 7/41* (2006.01)
*G01S 13/56* (2006.01)
(Continued)

(52) U.S. Cl.
CPC ............ *G01S 7/415* (2013.01); *A61B 5/1102* (2013.01); *A61B 5/113* (2013.01); *A61B 5/1114* (2013.01);
(Continued)

(58) Field of Classification Search
CPC ............ G01S 7/415; G01S 7/417; G06F 3/017
See application file for complete search history.

(56) References Cited

U.S. PATENT DOCUMENTS

| 4,197,537 A | 4/1980 | Follen et al. |
| 5,361,070 A | 11/1994 | McEwan |

(Continued)

FOREIGN PATENT DOCUMENTS

| JP | 2011015887 A | 1/2011 |
| WO | 2013151614 A1 | 10/2013 |

(Continued)

OTHER PUBLICATIONS

"International Search Report".
(Continued)

*Primary Examiner* — Marc Anthony Armand
(74) *Attorney, Agent, or Firm* — Botos Churchill IP Law LLP

(57) ABSTRACT

A sensor for motion or gesture sensing may be configured to emit radio frequency signals such as for pulsed range gated sensing. The sensor may include a radio frequency transmitter configured to emit the pulses and a receiver configured to receive reflected ones of the emitted radio frequency signals. The received pulses may be processed by a motion channel and/or a gesture channel. The gesture channel may produce signals for further processing for identification of one or more different motion gestures such as by calculating and evaluating features from one or more of the amplitude, phase and frequency of the output signals of the gesture channel. The sensing apparatus may optionally serve as a monitor for evaluating user activities, such as by counting certain activities. The sensor may optionally serve as a user (Continued)

control interface for many different devices by generating control signal(s) based on the identification of one or more different motion gestures.

76 Claims, 47 Drawing Sheets

(51) Int. Cl.
| | |
|---|---|
| G01S 13/87 | (2006.01) |
| G01S 13/88 | (2006.01) |
| A61B 5/11 | (2006.01) |
| G06F 3/01 | (2006.01) |
| A61B 5/113 | (2006.01) |
| A61B 5/00 | (2006.01) |
| G01S 13/62 | (2006.01) |
| A61B 5/05 | (2006.01) |
| A61B 5/08 | (2006.01) |

(52) U.S. Cl.
CPC .......... *A61B 5/1123* (2013.01); *A61B 5/1128* (2013.01); *A61B 5/725* (2013.01); *A61B 5/7267* (2013.01); *G01S 7/417* (2013.01); *G01S 13/56* (2013.01); *G01S 13/62* (2013.01); *G01S 13/87* (2013.01); *G01S 13/88* (2013.01); *G06F 3/017* (2013.01); *A61B 5/0507* (2013.01); *A61B 5/0816* (2013.01); *A61B 5/1116* (2013.01)

(56) References Cited

U.S. PATENT DOCUMENTS

| | | | |
|---|---|---|---|
| 5,682,164 | A | 10/1997 | McEwan |
| 5,966,090 | A | 10/1999 | McEwan |
| 6,426,716 | B1 | 7/2002 | McEwan |
| 7,952,515 | B2 | 5/2011 | McEwan |
| 2010/0214158 | A1 | 8/2010 | McEwan |
| 2011/0181509 | A1 | 7/2011 | Tuulikki |
| 2012/0245479 | A1 | 9/2012 | Meena et al. |
| 2014/0024917 | A1 | 1/2014 | McMahon et al. |
| 2014/0088373 | A1* | 3/2014 | Phillips .................. A61B 5/113 600/301 |
| 2014/0163343 | A1 | 6/2014 | Heneghan et al. |
| 2015/0223733 | A1* | 8/2015 | Al-Alusi ............... A61B 5/1112 600/479 |
| 2016/0054804 | A1* | 2/2016 | Gollakata ............... G06F 3/017 345/156 |
| 2016/0259421 | A1* | 9/2016 | Gollakota ......... H04M 1/72558 |

FOREIGN PATENT DOCUMENTS

| | | |
|---|---|---|
| WO | 2013152403 | 10/2013 |
| WO | 2014055755 A1 | 4/2014 |
| WO | 2014137838 A1 | 9/2014 |
| WO | 2014165476 A1 | 10/2014 |
| WO | 2015009958 A1 | 1/2015 |
| WO | 2015054419 A1 | 4/2015 |

OTHER PUBLICATIONS

Li, Yiran, et al., "Wireless Radar Devices for Smart Human-Computer Interaction", IEEE, 2014, 65-68.
Mercuri, et al., "Analysis of an Indoor Biomedical Radar-Based System for Health Monitoring", IEEE, May 2013.
Wan, Qian, et al., "Gesture Recognition for Smart Home Applications using Portable Radar Sensors", IEEE, 2014, 6414-6417.
JP Office Action dated Jun. 12, 2020 for JP Application No. P2017-554454.
Singh, Aditya, et al., "Activity Monitoring and Motion Classification of the Lizard *Chamaeleo jacksonii* Using Multiple Doppler Radars", 34th Annual International Conference of the IEEE Engineering in Medicine and Biology Society, 2012, pp. 4525-4528, DOI:10.1109/EMBC.2012.6346973.
Chinese Office Action dated Mar. 3, 2020, CN Application No. 2016800233314.

\* cited by examiner

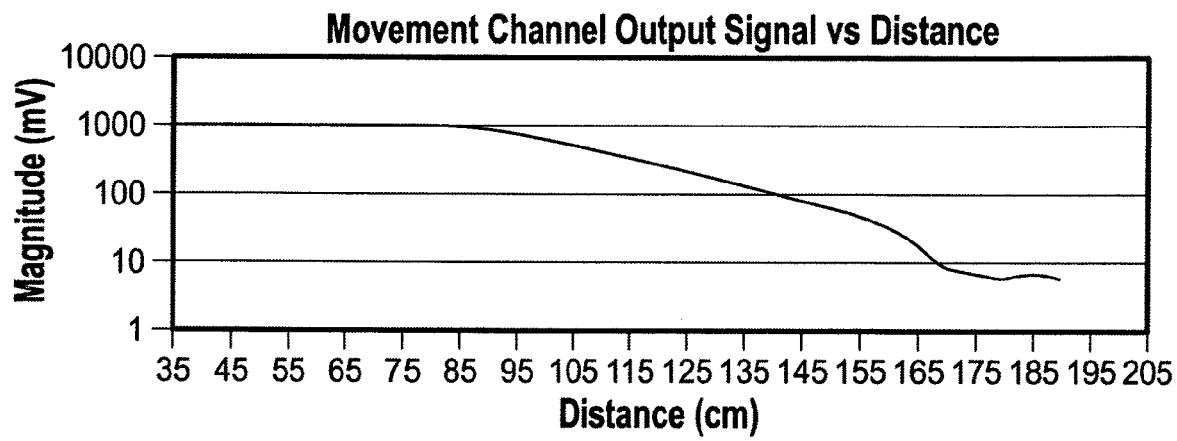
FIG. 5A
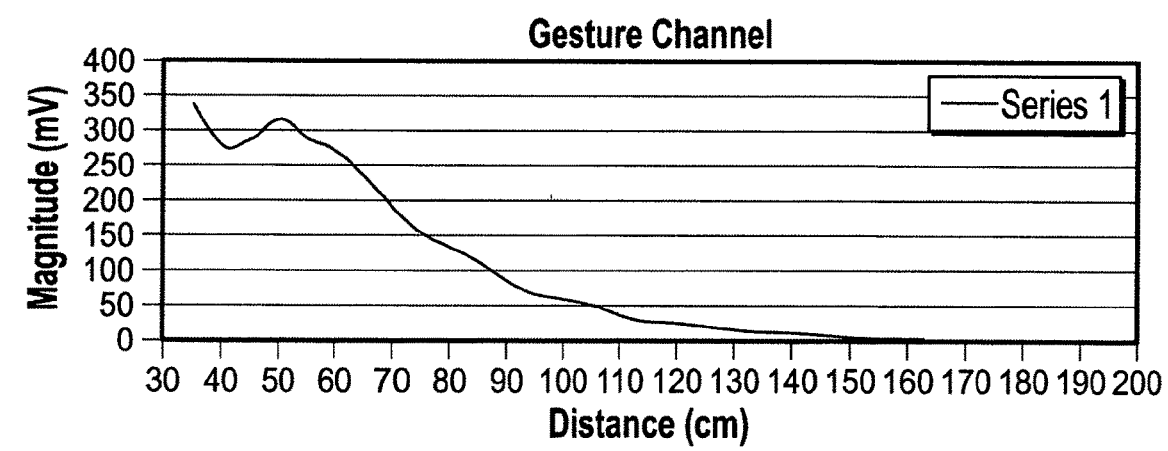
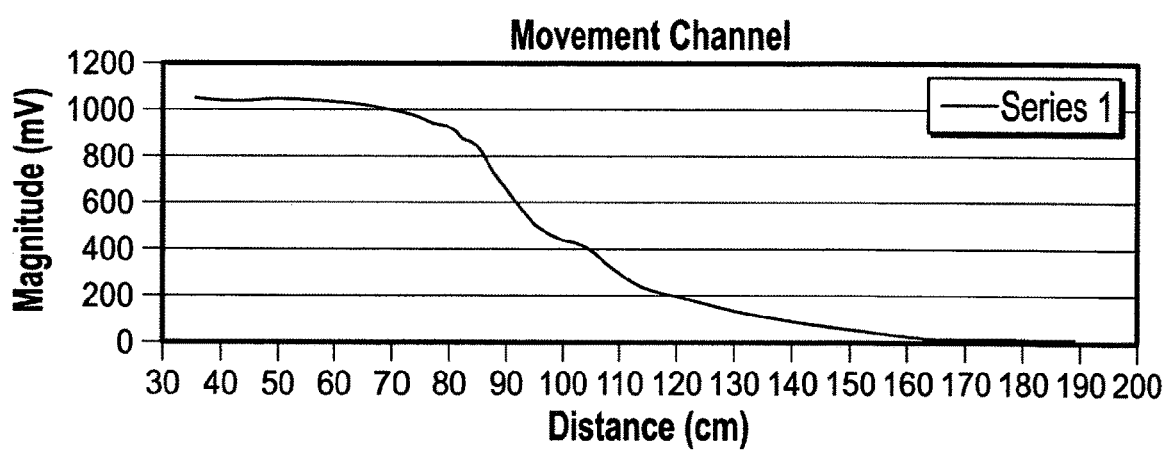
FIG. 5B

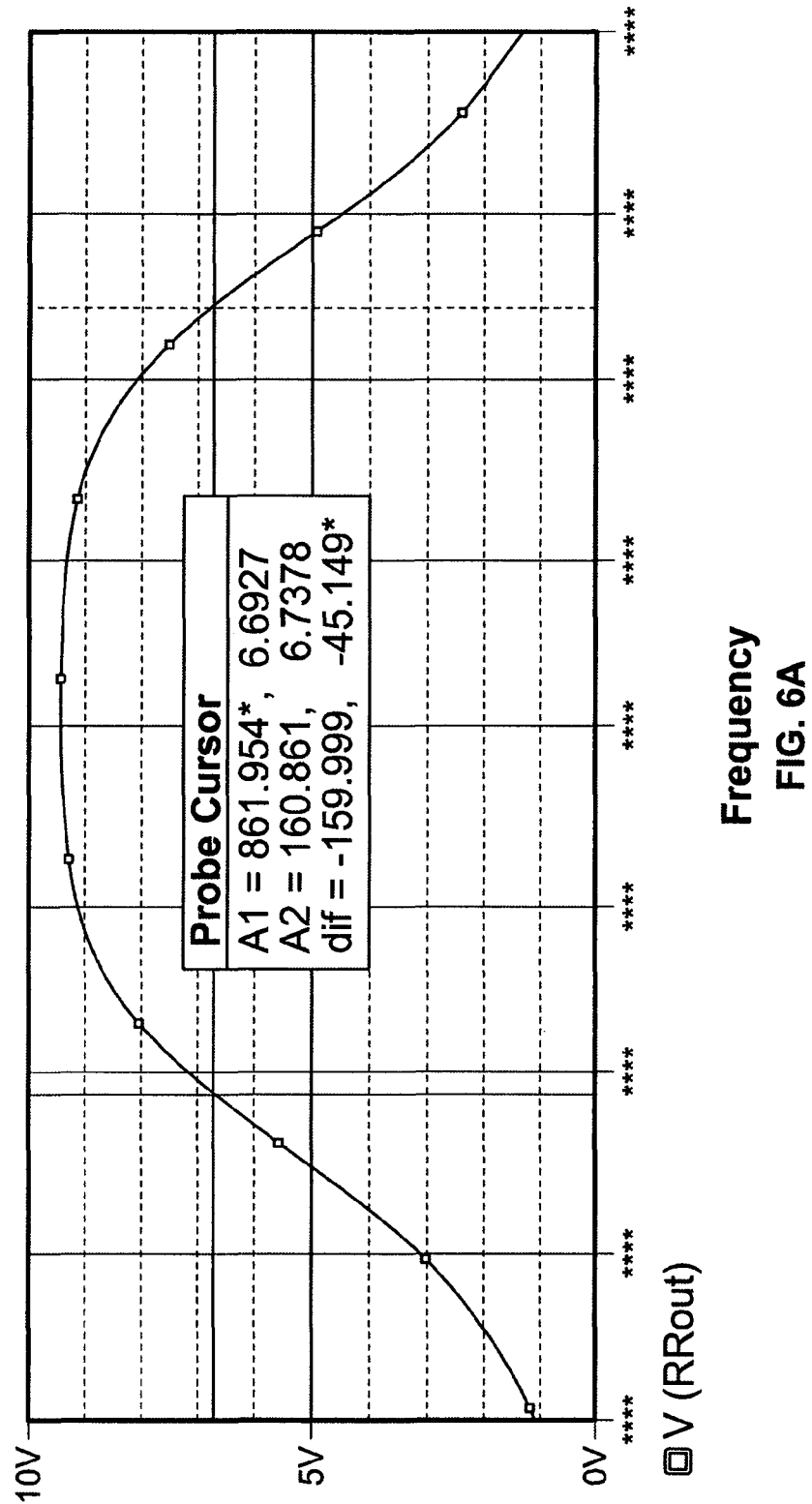

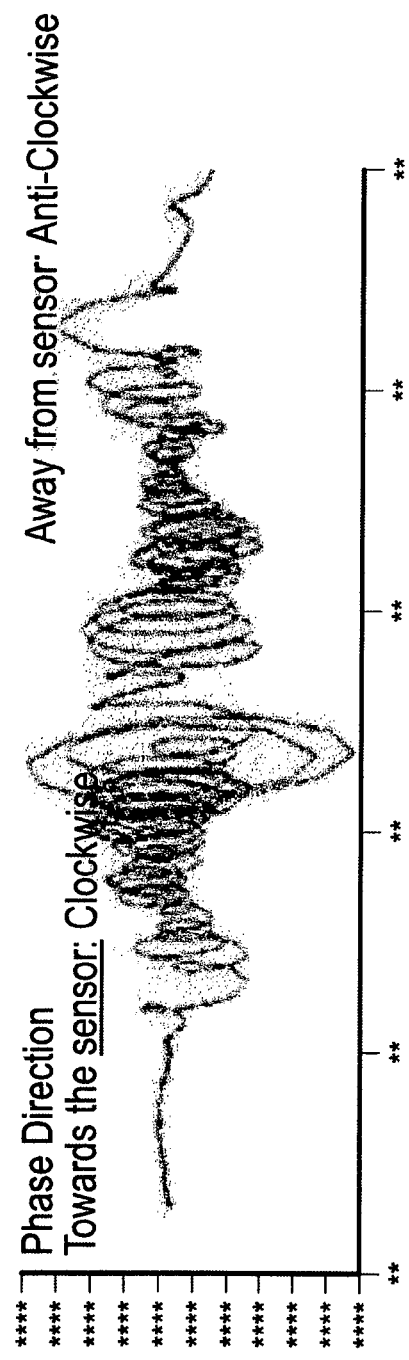
FIG. 9

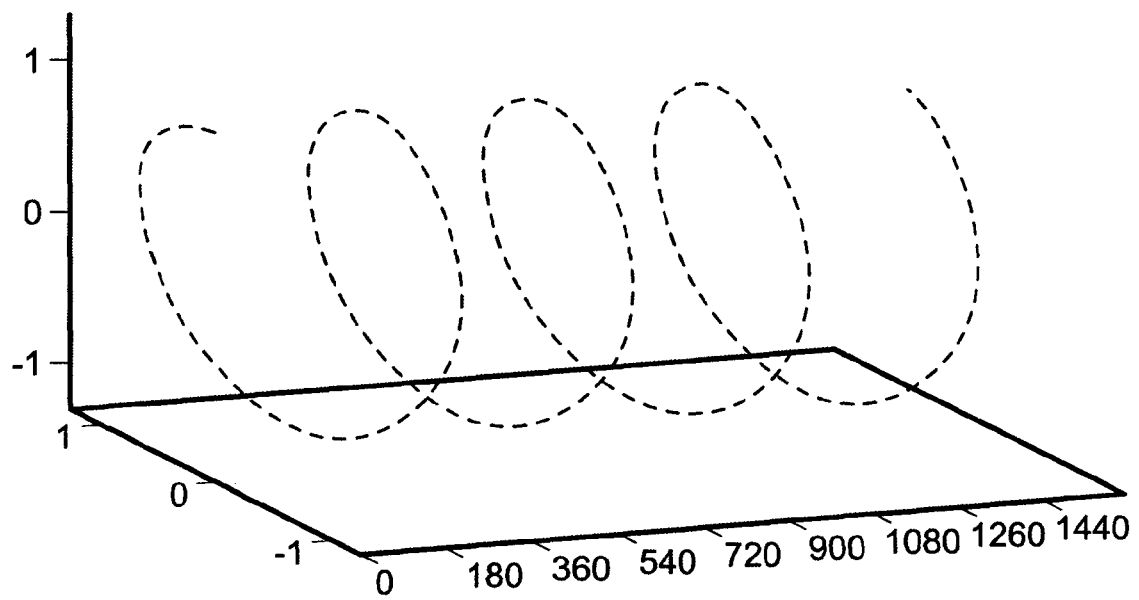
FIG. 10
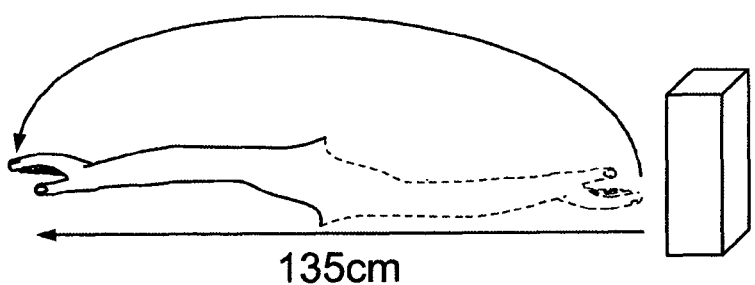
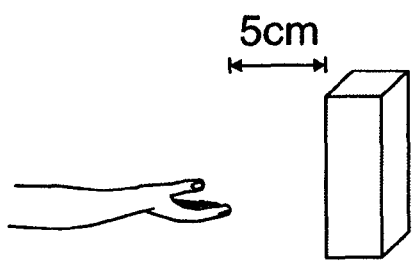
FIG. 11

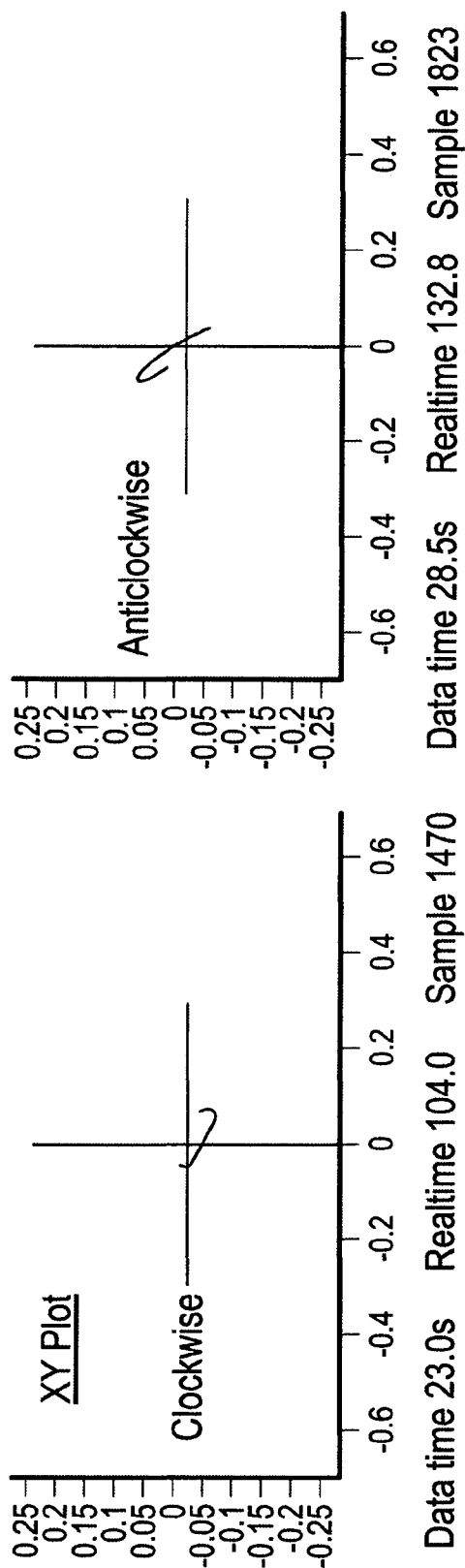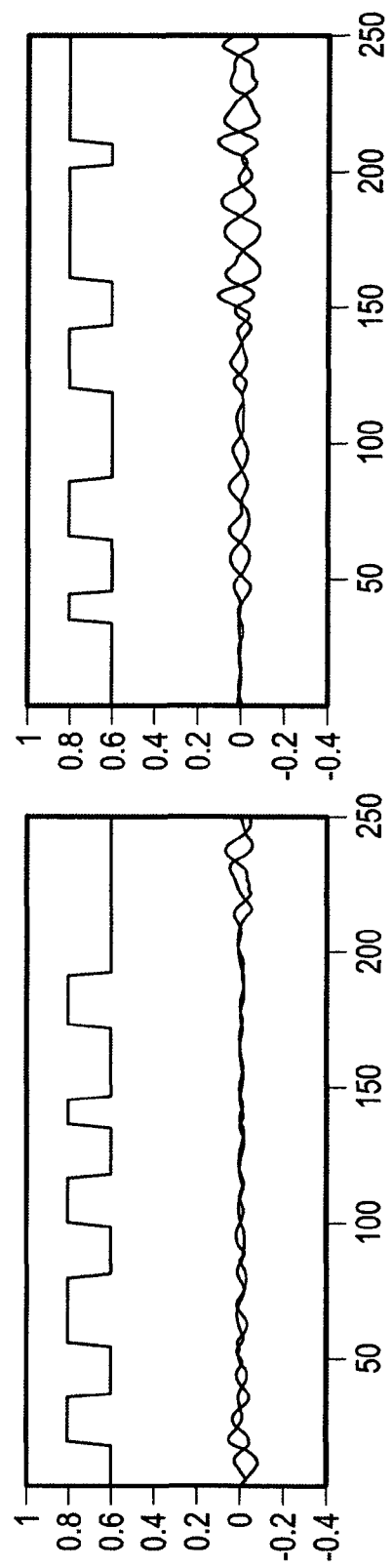
FIG. 13

Gesture 1

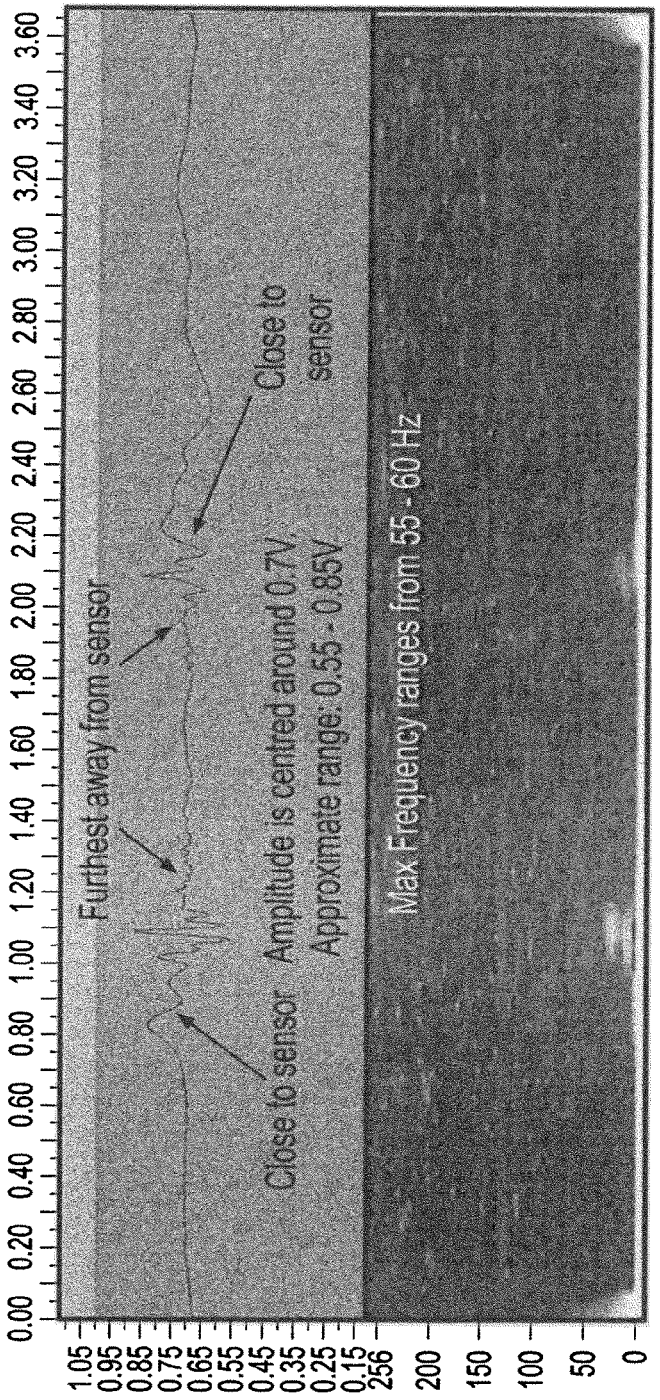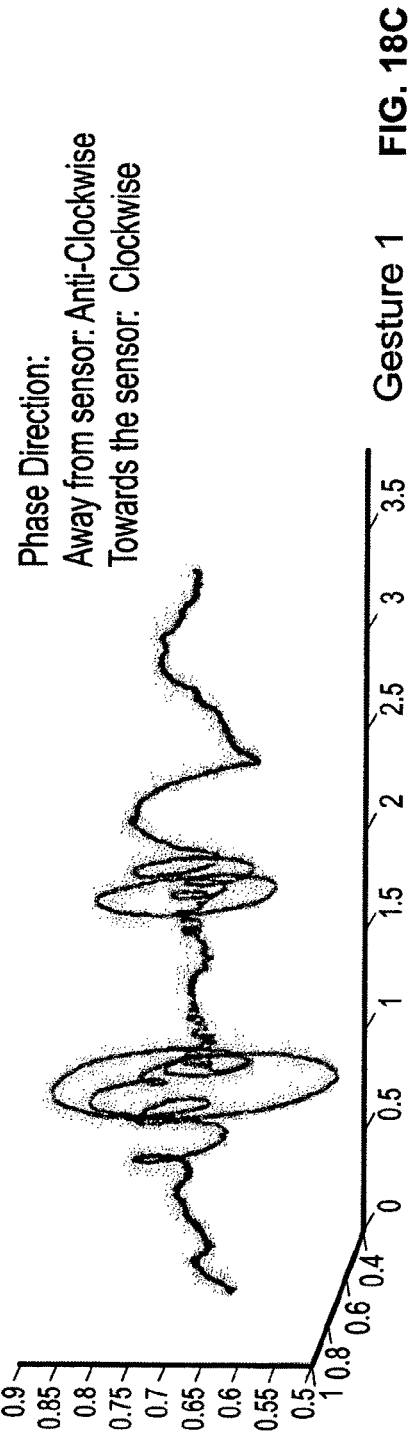
FIG. 18C

Gesture 2

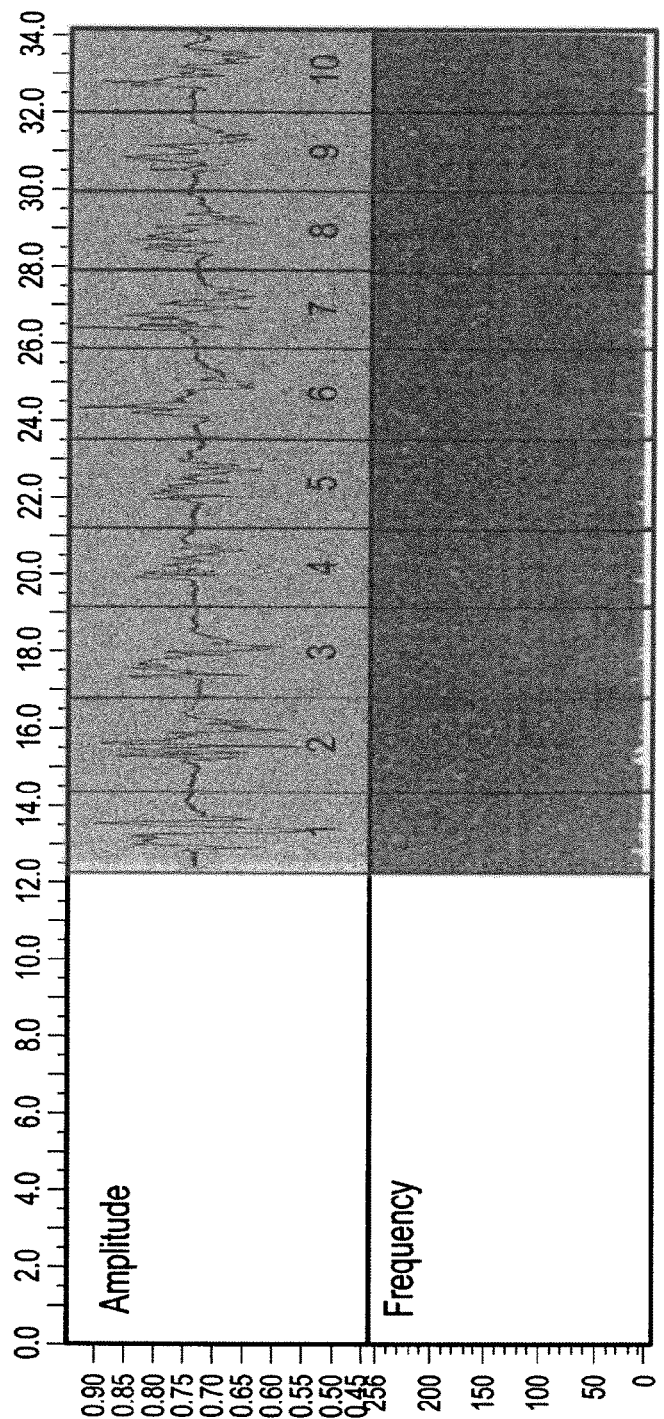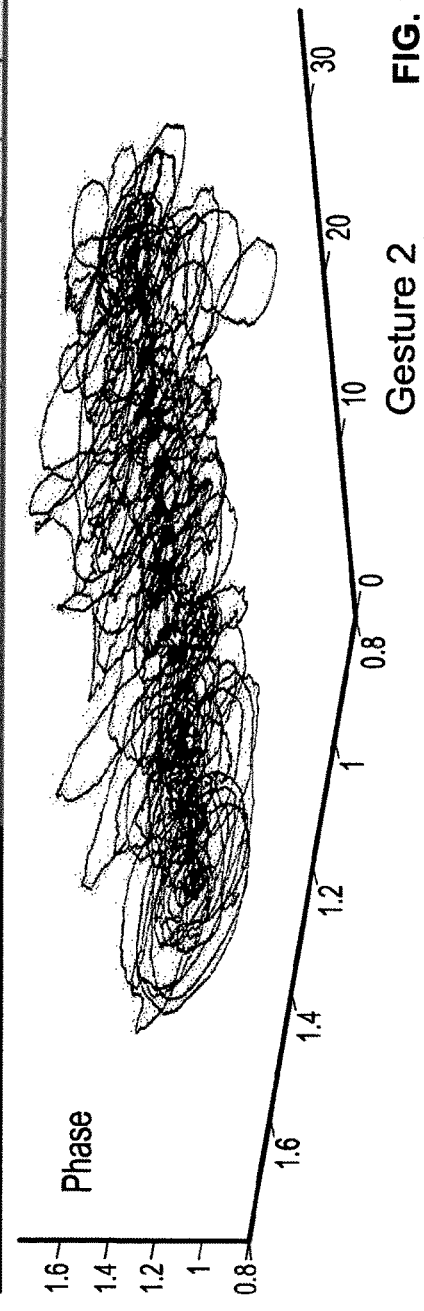
FIG. 19B

Gesture 3

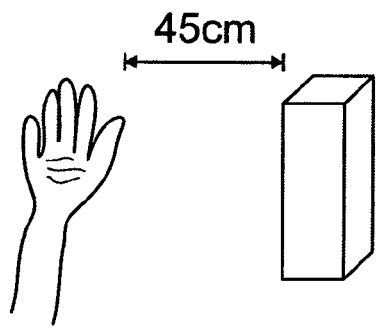
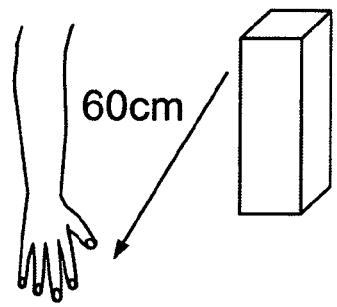
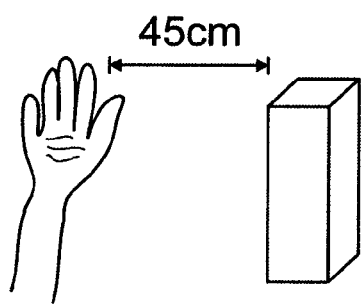
Gesture 4
FIG. 21A

Gesture 5

Gesture 6

Gesture 7

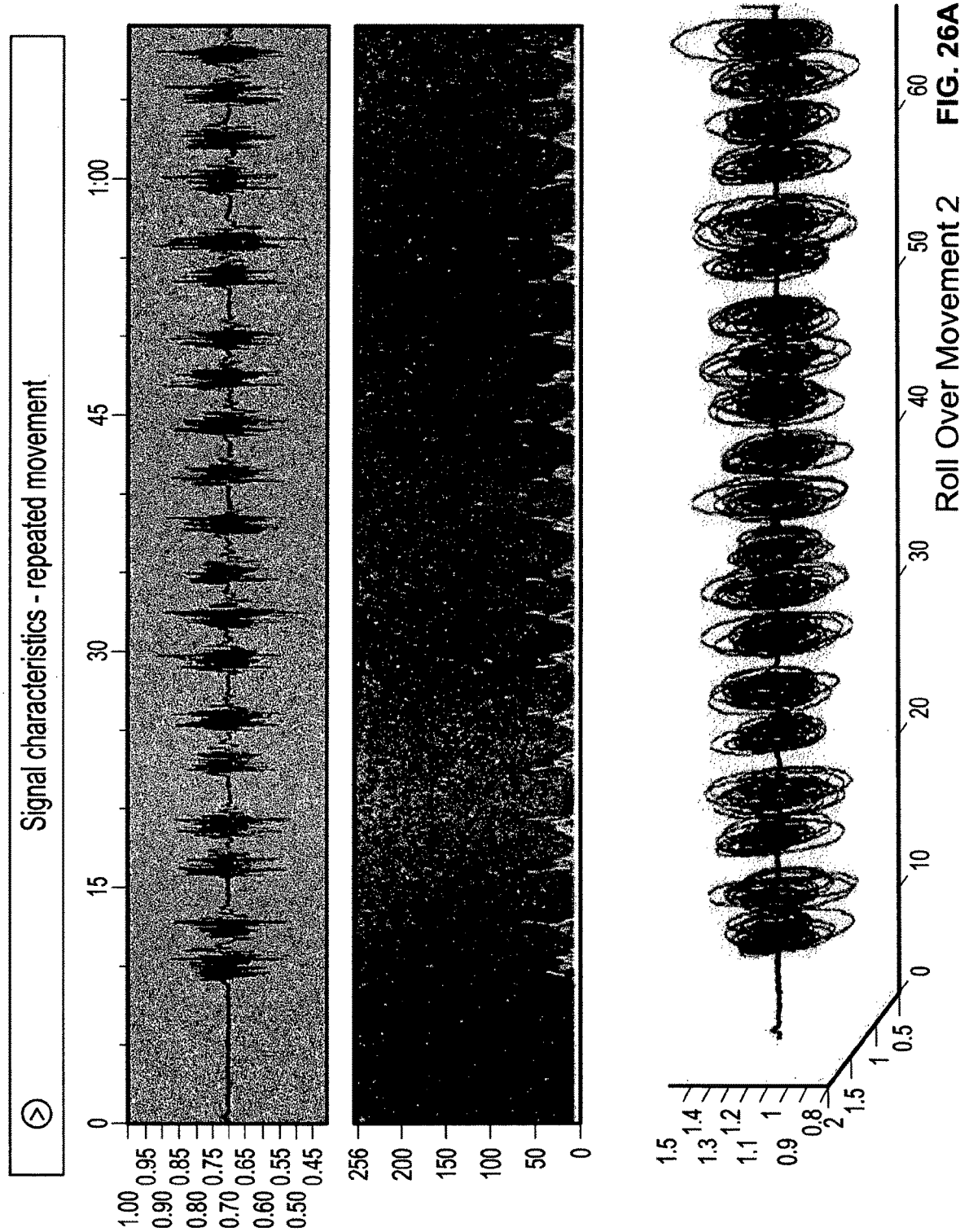

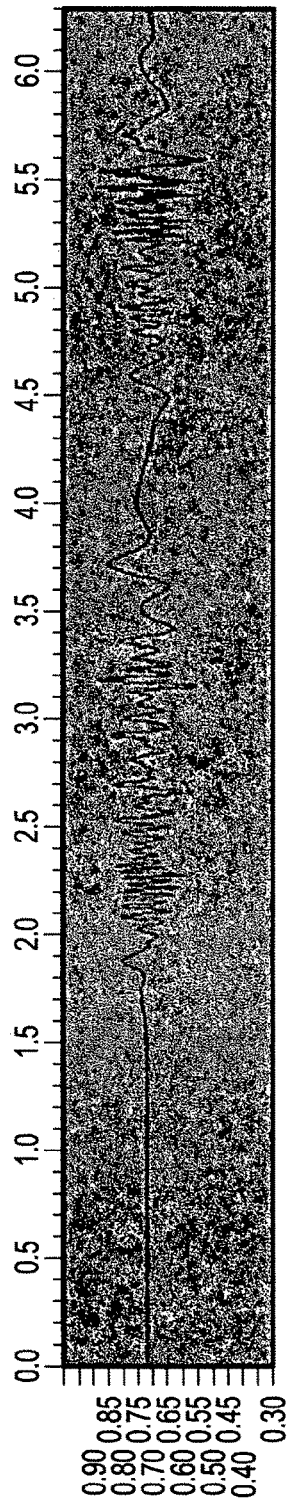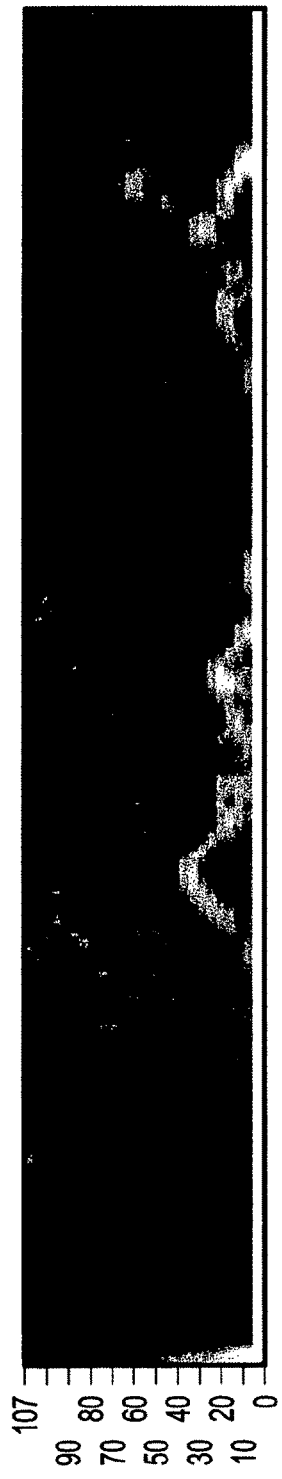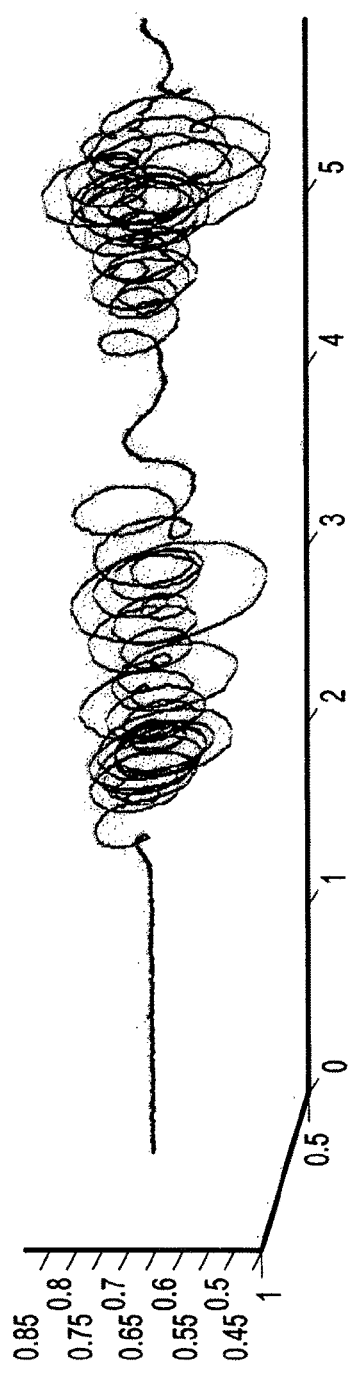
FIG. 26B

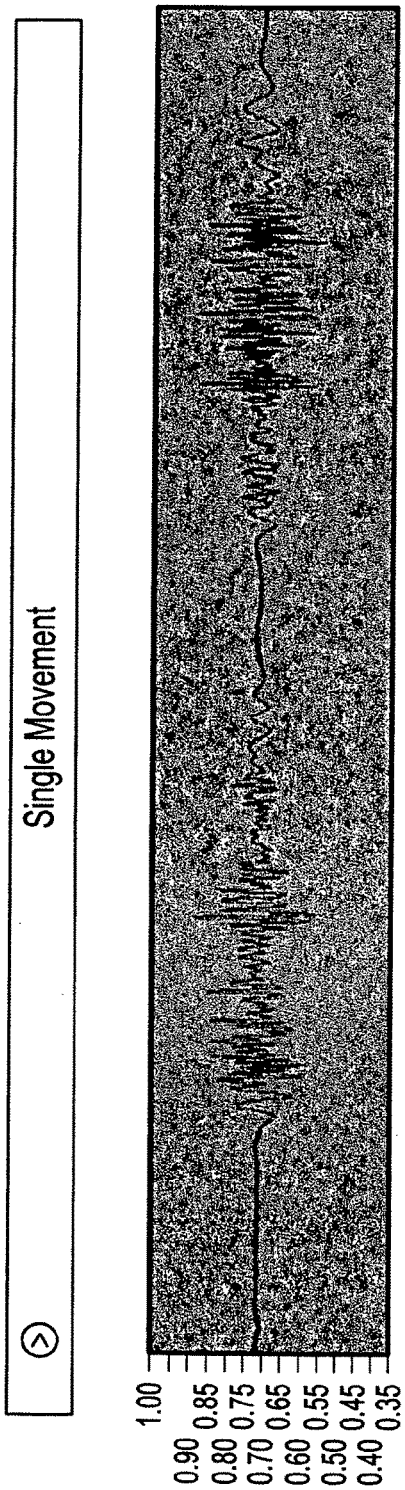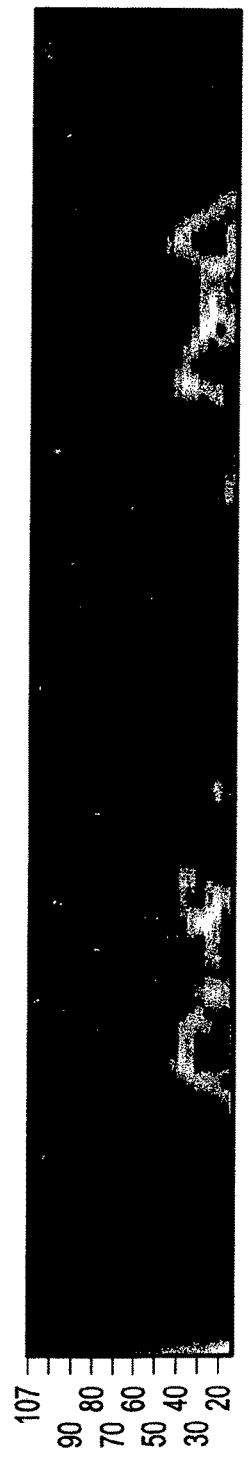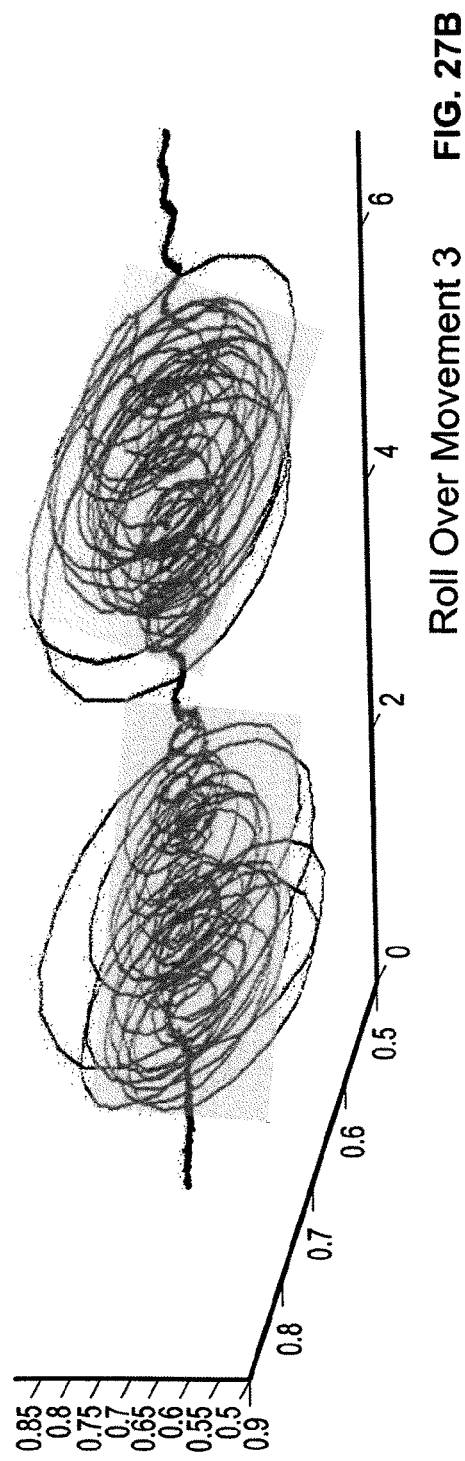
FIG. 27B

GESTURE RECOGNITION WITH SENSORS

CROSS-REFERENCE TO RELATED APPLICATIONS

The present application is a national phase entry under 35 U.S.C. § 371 of International Application No. PCT/EP2016/058806 filed Apr. 20, 2016, published in English, which claims priority from U.S. Provisional Patent Application No. 62/150,086 filed Apr. 20, 2015, all of which are incorporated herein by reference.

FIELD OF THE TECHNOLOGY

The present technology relates to methods and apparatus for detection of characteristics of moving objects and living subjects. More particularly, it relates to sensing or recognizing gestures or other bodily motions such as with radio frequency sensors.

BACKGROUND OF THE TECHNOLOGY

Continuous wave (CW) Doppler radar motion sensors emit a continuous wave radio frequency (RF) carrier and mix the transmitted RF with the return echoes to produce a difference frequency equal to the Doppler shift produced by a moving target. These sensors do not have a definite range limit (i.e., they can receive signals for both near and far objects, with the received signal being a function of radar cross section). This can lead to false triggers i.e., motion artefact interference. They may also have an undesirably high sensitivity at close range that leads to false triggering.

A pulse Doppler motion sensor is described in U.S. Pat. No. 4,197,537 to Follen et al. A short pulse is transmitted and its echo is self-mixed with the transmitted pulse. The pulse width defines the range-gated region. When the transmit pulse ends, mixing ends and target returns arriving after the end of the transmit pulse are not mixed and are thereby gated out.

A Differential pulse Doppler motion sensor disclosed in U.S. Pat. No. 5,966,090, "Differential Pulse Radar Motion Sensor," to McEwan, alternately transmits two pulse widths. It then subtracts the Doppler responses from each width to produce a range gated Doppler sensing region having a fairly constant response versus range.

Impulse radar, such as that described in U.S. Pat. No. 5,361,070, "Ultra-Wideband Radar Motion Sensor," to McEwan produces a very narrow sensing region that is related to the transmitted impulse width. A two-pulse Doppler radar motion sensor, as described in U.S. Pat. No. 5,682,164, "Pulse Homodyne Field Disturbance Sensor," to McEwan, transmits a first pulse and after a delay generates a second pulse that mixes with echoes from the first pulse. Thus a range gated sensing band is formed with defined minimum and maximum ranges. UWB radar motion sensors have the disadvantage of not having global RF regulatory acceptance as an intentional radiator. They also have difficulty sensing objects at medium ranges and in some embodiments can be prone to RF interference.

A modulated pulse Doppler sensor is described in U.S. Pat. No. 6,426,716 to McEwan. The range gated microwave motion sensor includes adjustable minimum and maximum detection ranges. The apparatus includes an RF oscillator with associated pulse generating and delay elements to produce the transmit and mixer pulses, a single transmit (TX)/receive (RX) antenna or a pair of separate TX and RX antennas, and an RF receiver, including a detector/mixer with associated filtering, amplifying and demodulating elements to produce a range gated Doppler signal from the mixer and echo pulses.

In U.S. Pat. No. 7,952,515, McEwan discloses a particular holographic radar. It adds a range gate to holographic radar to limit response to a specific downrange region. McEwan states that cleaner, more clutter-free radar holograms of an imaged surface can be obtained, particularly when penetrating materials to image interior image planes, or slices. The range-gating enables stacked hologram technology, where multiple imaged surfaces can be stacked in the downrange direction.

In U.S. Patent Application Publ. no. 2010/0214158, McEwan discloses an RF magnitude sampler for holographic radar. McEwan describes that the RF magnitude sampler can finely resolve interferometric patterns produced by narrowband holographic pulse radar.

In U.S. Patent Application Publication No. 2014/0024917, McMahon et al, describe a sensor for physiology sensing that may be configured to generate oscillation signals for emitting radio frequency pulses for range gated sensing. The sensor may include a radio frequency transmitter configured to emit the pulses and a receiver configured to receive reflected ones of the emitted radio frequency pulses. The received pulses may be processed to detect physiology characteristics such as motion, sleep, respiration and/or heartbeat.

There may be a need to improve sensors and processing for radio frequency sensing such as for detection or recognition of particular motions or gestures.

SUMMARY OF THE TECHNOLOGY

One aspect of some embodiments of the present technology relates to a sensor for detecting gestures or particular bodily motions.

An aspect of some embodiments of the present technology relates to a sensor for detecting a gesture or bodily motion with radio frequency signals.

Another aspect of some embodiments of the technology relates to such a sensor with a circuit configured to generate pulsed radio frequency (RF) signals such as for gesture recognition or bodily movement type recognition.

Some versions of the present technology may include a radio frequency motion sensing apparatus. The apparatus may include a radio frequency transmitter configured to emit radio frequency signals. The apparatus may include a receiver configured to receive reflected ones of the emitted radio frequency signals. The apparatus may include a motion channel circuit configured to process the received reflected ones of the emitted radio frequency signals and produce motion output signals. The apparatus may include a processor configured to evaluate the motion output signals and identify a motion based on any one or more of amplitude, phase and frequency of the motion output signals.

In some cases, the identified motion may include at least one of hand gesture, an arm gesture or a combined hand and arm gesture. The identified motion may include a rollover motion. The identified motion may include an activity. The identified motion may include a shaving activity.

In some cases, the motion output signals may include in phase and quadrature phase signals. The emitted radio frequency signals may include pulsed radio frequency oscillating signals. The motion channel circuit may include a bandpass filter. The apparatus, or the processing circuits thereof, may be configured to demodulate the received reflected ones of the emitted radio frequency signals with signals representing the emitted radio frequency signals. The apparatus, or the processing circuits thereof, may be configured to calculate time difference and/or phase difference between the emitted radio frequency signals and the received reflected ones of the emitted radio frequency signals and to identify the motion based on the calculated time difference and/or phase difference.

In some cases, the motion channel may include an antialiasing filter. The processor may be configured to classify a motion based on a plurality of features calculated from any two of the amplitude, phase and frequency of the motion output signals. The processor may be configured to classify or identify a motion based on a duration calculated with any one or more of the amplitude, phase and frequency of the motion output signals. The processor may be configured to calculate the plurality of features from each of the amplitude, phase and frequency of the motion output signals. The plurality of features may include a determined duration derived from analysis of any one or more of the amplitude, phase and frequency of the motion outputs signals.

In some cases, the calculated plurality of features may include one or more of:

(a) a frequency characteristic derived from stopped frequency through a gesture in motion up to some maximum frequency, then back to stopped again;

(b) a time and frequency analysis of the signal comprising any of short time Fourier transform, peak and harmonic tracking and/or channel processing of an I and/or Q channel(s);

(b) a phase characteristic comprising any of: a phase difference between I and Q signals and an evaluation of a repetitive signal within a certain number of standard deviations of a mean of characteristic change;

(c) an amplitude characteristic comprising any of: peak and trough detection, zero crossing detection, and envelope of signal detection; and (d) a learn skewness, kurtosis, spread in frequency, phase, amplitude, mean, and/or standard deviation.

Optionally, the processor may be configured to compare the calculated plurality of features to one or more thresholds. The processor may be configured to identify the motion by selecting one from a plurality of predetermined motions. The processor may be configured to count a number of occurrences of the identified motion. The processor may be further configured to generate a control signal for operation of a device based on the identified motion. The processor may be further configured to generate different control signals for different operations of a device based on different identified motions. The processor may be configured to evaluate the motion output signals and identify a motion based on motion output signals from a plurality of sensors. The plurality of sensors may include a first sensor and a second sensor, wherein the processor evaluates I and Q signals from the first sensor and the second sensor to identify the motion. The processor may determine an I differential and a Q differential of the I and Q signals from the first sensor and the second sensor. The plurality of sensors may include a first sensor, second sensor and a third sensor, wherein the processor evaluates I and Q signals from the first sensor, the second sensor and the third sensor to identify the motion. In some cases of the apparatus, at least two of the three sensors may be positioned to be orthogonal to each other. The evaluated I and Q signals may be used by the processor to identify movement characteristics in more than one dimension. The processor may be configured to extract one or more of the following parameters of the moving object: velocity, change in velocity, distance, change in distance, direction and change in direction.

Some versions of the present technology may involve a method for radio frequency motion sensing. The method may include, with a radio frequency transmitter, emitting radio frequency signals. The method may include, with a receiver, receiving reflected ones of the emitted radio frequency signals. The method may include processing the received reflected ones of the emitted radio frequency signals to produce motion output signals with a motion channel circuit. The method may include, in a processor, evaluating the motion output signals and identifying a motion based on any one or more of amplitude, phase and frequency of the motion output signals.

In some cases, the identified motion may include any one of hand gesture, an arm gesture and a combined hand and arm gesture. The identified motion may include a rollover motion. The identified motion may include an activity. The identified motion may include a shaving activity. The motion output signals of the method may include in phase and quadrature phase signals. The emitted radio frequency signals may include pulsed radio frequency oscillating signals. The motion channel circuit may include a bandpass filter.

In some cases, the method may involve demodulating the received reflected ones of the emitted radio frequency signals with signals representing the emitted radio frequency signals. The method may include calculating time difference and/or phase difference between the emitted radio frequency signals and the received reflected ones of the radio frequency signals and identifying the motion based on the calculated time difference and/or phase difference. The motion channel may include an antialiasing filter.

In some cases, the method may include, with or in the processor, classifying a motion based on a plurality of features calculated from any two of the amplitude, phase and frequency of the motion output signals. The processor may classify or identify a motion based on a duration calculated with any one or more of the amplitude, phase and frequency of the motion output signals. The method may involve calculating, in the processor, the plurality of features from each of the amplitude, phase and frequency of the motion output signals. The plurality of features may include a determined duration derived from analysis of any one or more of the amplitude, phase and frequency of the motion outputs signals.

In some cases, the calculated plurality of features may include one or more of:

(a) a frequency characteristic derived from stopped frequency through a gesture in motion up to some maximum frequency, then back to stopped again;

(b) a time and frequency analysis of the signal including any of a short time Fourier transform, peak and harmonic tracking, and processing of I and/or Q channel(s);

(b) a phase characteristic including any of a phase difference between I and Q signals or an evaluation of a repetitive signal within a certain number of standard deviations of a mean of characteristic change;

(c) an amplitude characteristic including any of a peak and trough detection, a zero crossing detection, an envelope of signal detection; and (d) a learn skewness, kurtosis, spread in frequency, phase, amplitude, mean, and/or standard deviation.

Optionally, the method may involve, in the processor, comparing the calculated features to one or more thresholds. The method may involve, in the processor, identifying the motion by selecting one from a plurality of predetermined motions. The method may involve, in the processor, counting a number of occurrences of the identified motion. The method may involve, with the processor, generating a control signal for operation of a device based on the identified motion. The method may involve, with the processor, generating different control signals for different operations of a device based on different identified motions.

In some cases, the processor may evaluate the motion output signals from a plurality of sensors and identifies a motion based on the evaluated motion output signals. The plurality of sensors may include a first sensor and a second sensor, and the processor may evaluate I and Q signals from the first sensor and the second sensor to identify the motion. The processor may determine an I differential and a Q differential of the I and Q signals from the first sensor and the second sensor. Optionally, the plurality of sensors may include a first sensor, a second sensor and a third sensor, and the processor may evaluate I and Q signals from the first sensor, the second sensor and the third sensor to identify the motion. In some cases, at least two of the three sensors may be positioned to be orthogonal to each other. The evaluated I and Q signals may be used by the processor to identify movement characteristics in more than one dimension.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

FIG. 5A is a graph showing a movement channel output magnitude over distance for a sensor;

FIG. 5B contains graphs comparing a movement channel and gesture channel with respect to output magnitude over distance for another sensor;

FIG. 6A illustrates a frequency response of a gesture channels for a version of the sensor;

FIGS. 8 and 9 illustrate amplitude, frequency and phases responses for a single motion gesture of FIG. 7 and the repeated motion gesture respectively;

FIG. 10 is another plot of the phase response associated with the motion gesture of FIG. 7;

FIG. 11 illustrates another motion gesture with respect to an example sensor;

FIG. 13 illustrates detection of change in motion direction from I and Q signal difference;

FIGS. 18A-C illustrate a motion gesture and the amplitude, phase and frequency response by a suitable sensor to its repetition and the single movement;

FIGS. 19A-C illustrate another motion gesture and the amplitude, phase and frequency response by a suitable sensor to its repetition and the single movement;

FIGS. 21A-C illustrate a still different motion gesture and the amplitude, phase and frequency response by a suitable sensor to its repetition and the single movement;

FIGS. 26A-B illustrate another rollover motion and the amplitude, phase and frequency response by a suitable sensor to its repetition and the single movement;

FIGS. 27A-B illustrate a further rollover motion and the amplitude, phase and frequency response by a suitable sensor to its repetition and the single movement;

DETAILED DESCRIPTION

Figure 1:
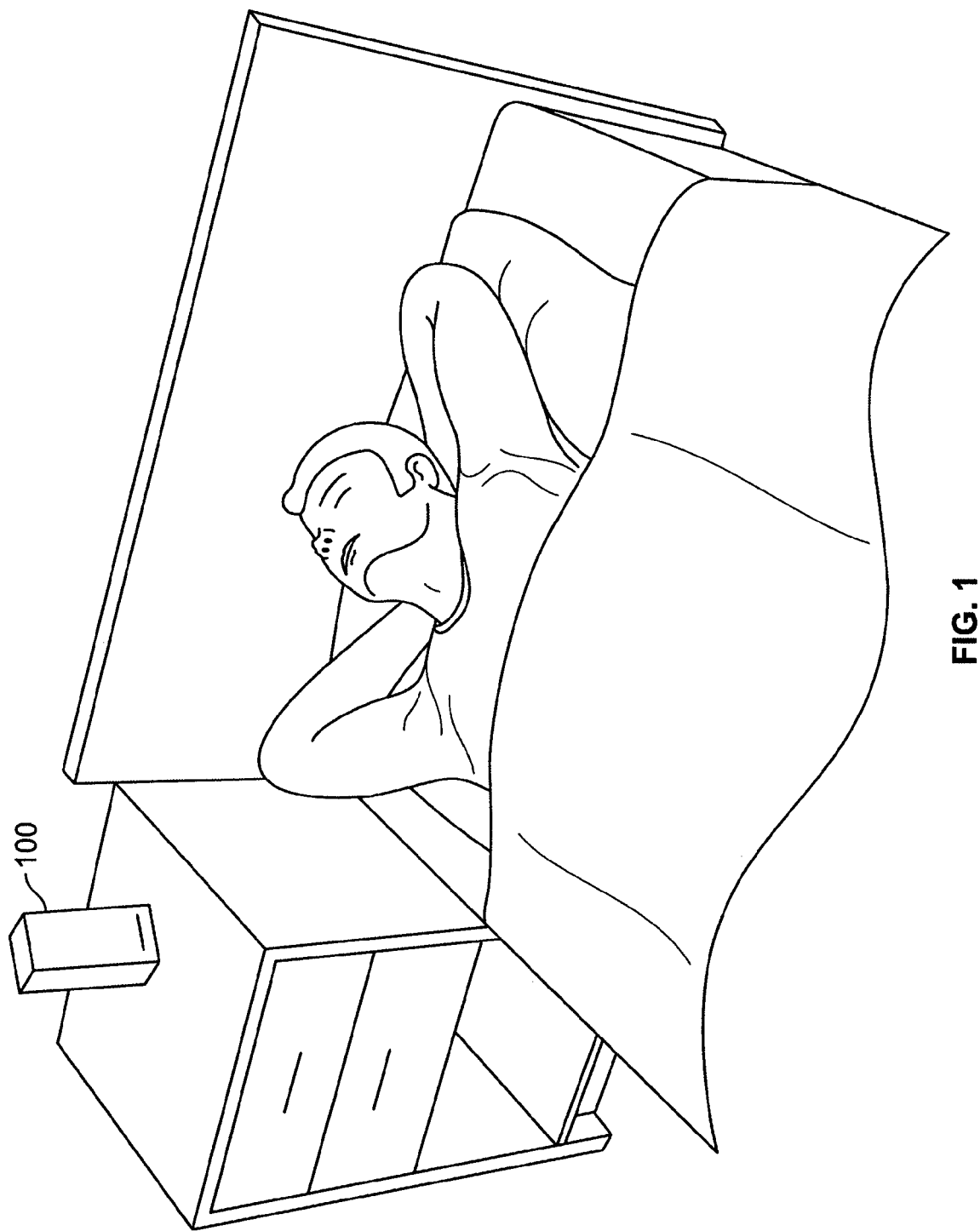
FIG. 1 is an illustration of an example detection apparatus suitable for implementation with a radio frequency physiology sensor of the present technology.

As illustrated in FIG. 1, some embodiments of the present technology may implement a sensing or detection apparatus 100, such as one configured with particular processing methodologies, useful for detecting particular motions of a user or a patient (the patient may be identical or a different person from the user of the detection apparatus 100) in the vicinity of the apparatus. The sensor may be a standalone sensor or may be coupled with other apparatus, such as a respiratory treatment apparatus or sleep assessment apparatus. For example, it may optionally provide an automated treatment response based on an analysis of the gestures or motion detected by the sensor of the apparatus. For example, a respiratory treatment apparatus with a controller and a flow generator may be configured with such a sensor and may be configured to adjust a pressure treatment generated at a patient interface (e.g., mask) in response to particular motions or gestures detected by the sensor. The respiratory treatment apparatus may be for example, a respiratory therapy or PAP apparatus, such as any one described in International Patent Application Publication No. WO 2013/152403, the entire disclosure of which is incorporated herein by reference.

In general, such motions or gestures may be understood to be any that are intentionally or subconsciously made by a person rather than those physiological characteristics that are involuntarily periodic in nature, (i.e., chest movement due to respiration or cardiac activity.) In this regard, movement signals sensed by a sensor that are generated by particular human gestures may be processed to identify or characterize the particular movement or gesture. For example, a hand movement, or particular hand movement, could be detected.

Larger movements such as the movement made by a person turning over in bed (a turnover) can also be recognized. Particularized detection of such movement events may then permit them to be counted or serve as a control for an apparatus (e.g., implemented to turn on or off a system, or to provide other control signals). The technology may also be implemented to classify physiological movement such as sway, breathing, and faster motion such as shaving or scratching. It could be implemented to improve the robustness of breathing rate detection when a subject is standing or sitting, such as by identifying and eliminating such sway and gesture motion for respiratory rate detection. The technology may be even be implemented to monitor subjects with persistent itch, irritation or discomfort, e.g., in a clinical trial of a dermatological cream for quantification of such itch related or discomfort related motion. In some cases, it could even be implemented to assess the efficacy of consumer products dependent on motion such as a shaving blade or cream/gel, and understand shaving motions, etc.

A sensor with suitable processing circuit(s) (e.g., one or more processors) may be configured as a gesture detection apparatus that may be implemented as a component (e.g., a control component) for many different types of apparatus. For example, a television or television receiver may include such a sensor for controlling the operations of the television or television receiver with different gestures (e.g., on/off, volume changes, channel changes etc.). Similarly, the gesture detection apparatus may be configured as part of a user interface for a gaming apparatus or computer, such as to control operations of the game or computer. Such a gesture detection apparatus may be implemented for many other apparatus that employ a user interface such that the user interface may be implemented as a gesture-controlled user interface. For example, a processor or controller may evaluate signals from one or more sensors to identify in the processor or controller a particular movement or gesture, and in response, activate generation of a visual (or audio) change to a displayed user interface (such as one displayed on a display device such as an LCD or LED screen). The identified gesture or the activated change may be used to issue one or more control signals to control a device (e.g., a computer, television, computer game console, user appliance, automated machine, robot, etc., that is coupled to, or communicates, with the processor or controller.

A typical sensor, such as a radar sensor, of such an apparatus may employ a transmitter to emit radio frequency waves, such as radio frequency pulses for range gated sensing. A receiver, which may optionally be included in a combined device with the transmitter, may be configured to receive and process reflected versions of the waves. Signal processing may be employed, such as with a processor of the apparatus that activates the sensor, for gesture or motion recognition based on the received reflected signals.

Figure 2:
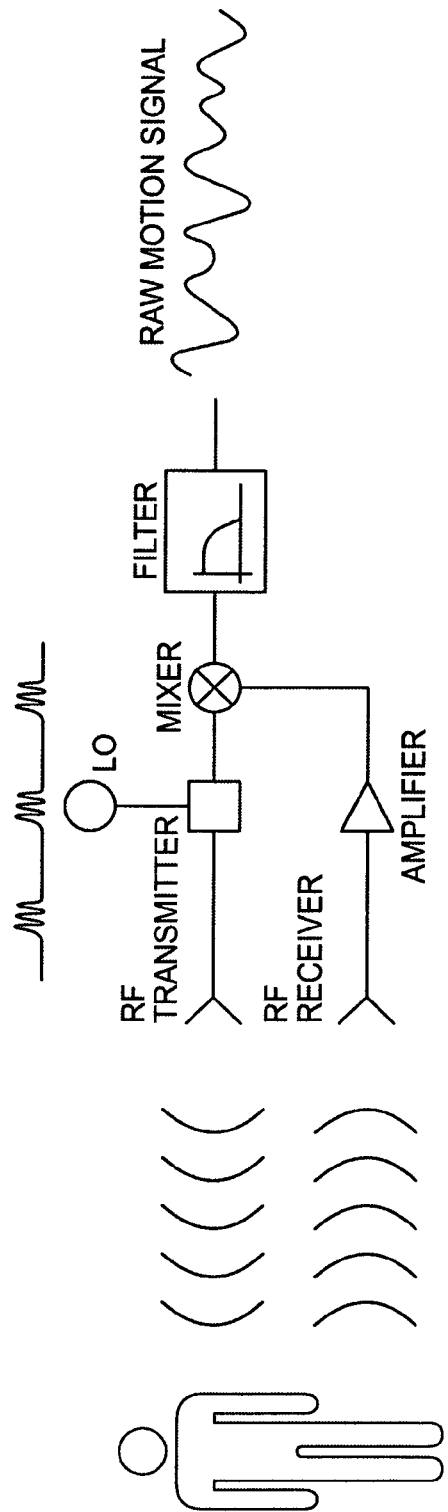
FIG. 2 is a diagram illustrating a conceptual structure and process flow for evaluation of sensor signals suitable for some embodiments of the technology.

For example, as illustrated in FIG. 2, the transmitter transmits a radio-frequency signal towards a subject, e.g., a human. Generally, the source of the RF signal is a local oscillator (LO). The reflected signal is then received, amplified and mixed with a portion of the original signal, and the output of this mixer may then be filtered. In some cases, the received/reflected signal may be demodulated by the transmitted signal, or the phase or time difference between them may be determined, for example, as described in US-2014-0163343-A1, the entire disclosure of which is incorporated herein by reference.

The resulting signal may contain information about the movement (e.g., gestures), respiration and cardiac activity of the person, and is referred to as the raw motion sensor signal. In some cases, the signal may be processed to exclude involuntary periodic activity (e.g., respiration and/or cardiac activity) so that movement information in the signal may be classified for its particular gesture or movement type. In some cases, the sensor may be a sensor described in U.S. Patent Application Publication No. 2014/0024917, the entire disclosure of which is incorporated herein by reference.

Figure 3:
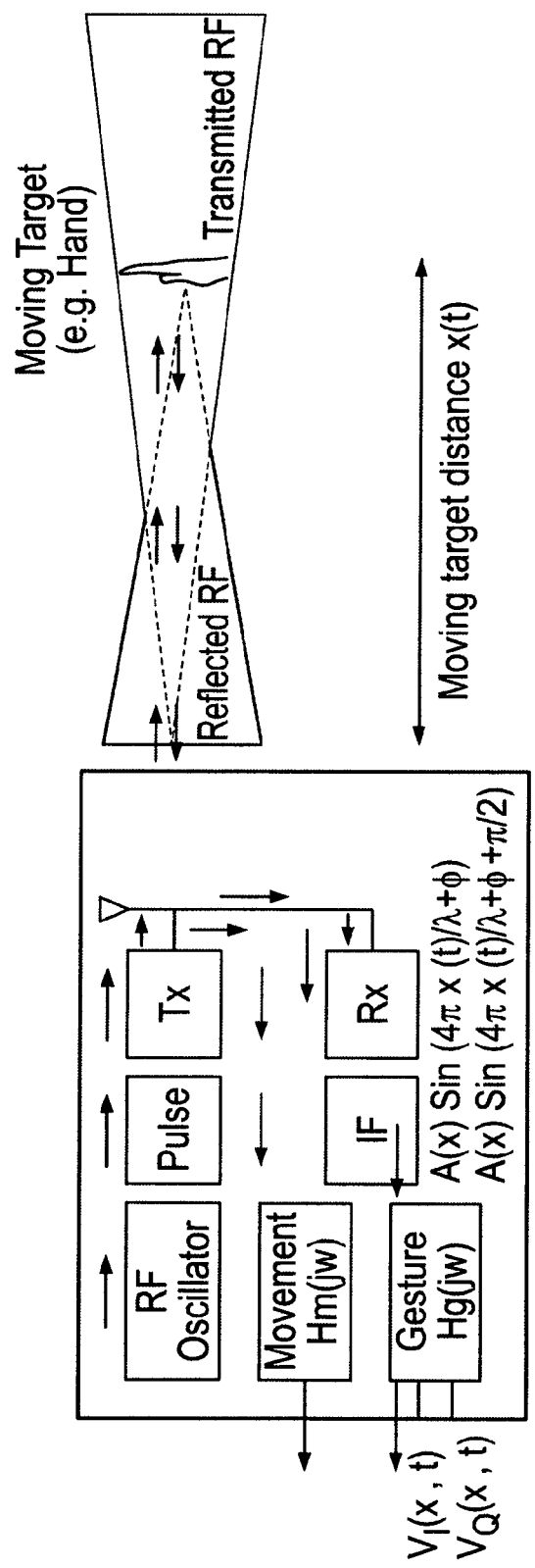
FIG. 3 is a block diagram with processing for a sensor apparatus in some versions of the technology.

The sensor may include various motion channels for processing of detected signals, for example, such a sensor may be implemented with a gesture processor to provide a gesture channel output signal. This may be distinct from a movement processor that provides a movement channel output signal. Having multiple processors can permit output of signals with different characteristics (e.g., different bandwidths, different sampling rates, etc.) for different motion evaluations. For example, there may be more information in a gesture signal rather than a breathing or cardiac signal. For example, the gesture signal can include information representing detection of a wider range of motion speeds. For example, a 1 metre per second movement might cause a 70 Hz baseband signal in a 10.525 GHz receiver. A typical sensing scenario might be able to detect speeds of between 1 mm/s to 5 m/s. For gesture detection, frequencies greater than 10 Hz (1 cm/s up to 5 m/sec) may be evaluated. For breathing, detection may involve evaluation of frequencies corresponding to velocities in range of 1 mm/sec to approximately 1 m/s. Thus, a movement processor may generate a signal focused on slower movements, and a gesture processor may generate a signal with a much wider band that may include both slow movements as well as faster movements. Thus, the sensor may implement analog and/or digital circuit components, for signal processing of the received sensor signal. This may optionally be implemented, at least in part, in one or more digital signal processors or other application specific integrated chips. Thus, as illustrated in FIG. 3, the sensor may be implemented with the gesture processor to implement a particular transfer function (Hg), as well as an additional movement processor to implement a particular transfer function (Hm), either of which may be considered a motion processor or channel circuit for producing motion output signals.

For example, in some cases, the sensor may have a gesture channel that provides quadrature output signals (I and Q) whose amplitude, frequency and phase is given by:

$$VI(x,t) = Hg(j\omega)A(x)\operatorname{Sin}(4\pi x(t)/\lambda + \phi)$$

$$VQ(x,t) = Hg(j\omega)A(x)\operatorname{Sin}(4\pi x(t)/\lambda + \phi + \pi/2)$$

Where:

Hg(jω) is the transfer function of the sensor gesture channel such as in a baseband circuit or baseband processor;

A(x) is the demodulated received signal strength and hence dependent on target radar cross section (size) and target distance (x);

x(t) is the displacement of the target with time

λ is the wavelength of the RF signal (e.g., a wavelength in free space corresponding to a 10.525 GHz frequency signal (e.g., a wavelength of 28.5 mm); and Jω—Is the frequency response of the system where co is the angular velocity and j is the complex number (0+√−1), which provides the phase information).

The gesture channel will have a frequency response to movement. For an in-band movement signal with a linear velocity v which moves a distance dx from position x0 to position x1 towards or away from the sensor in a time interval dt starting at t0 and ending at t1 the gesture channel output signal frequency f is given by $$2\pi f(t1-t0) = 4\pi(x1-x0)/\lambda,$$

$$2\pi f dt = 4\pi dx/\lambda.$$

For a 10.525 GHz, 28.5 mm λ sensor f~70.17 v where f (Hz) and v(m/s)) Here, taking λ into account, the units match on both sides such that wf (1/s), v (m/s) and 2/λ, =70.175 (m^−1). The constant value of 70 is actually 1/(2λ) and has the dimension of m−1.

In general:

$$f(t) = 2v(t)/\lambda$$

Typically, the amplitude of the output signal at any particular frequency will depend on the gesture channel transfer function frequency response.

Figure 4:
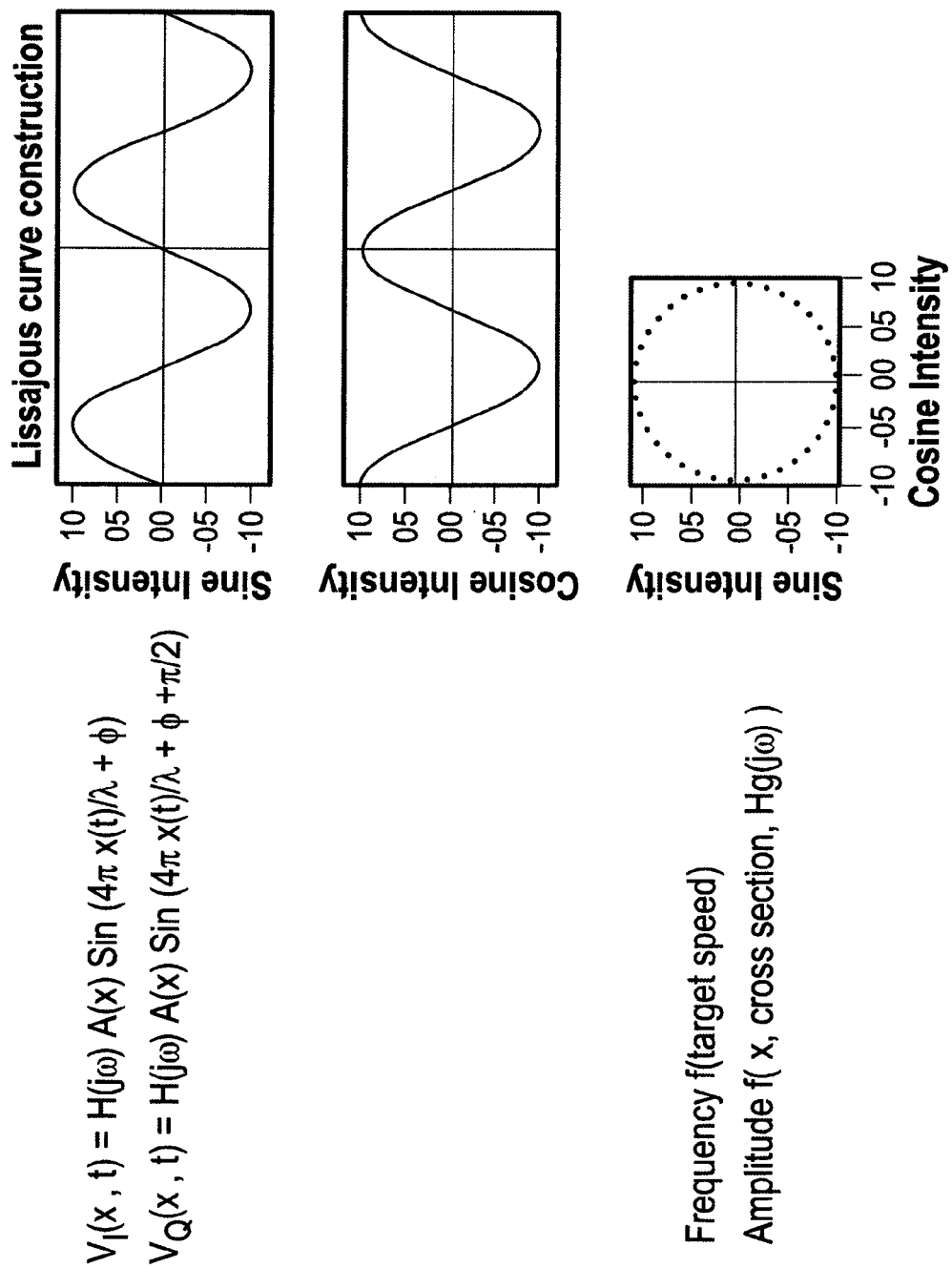
FIG. 4 illustrates phase response of an example gesture transfer function suitable for the present technology.
Figure 7:
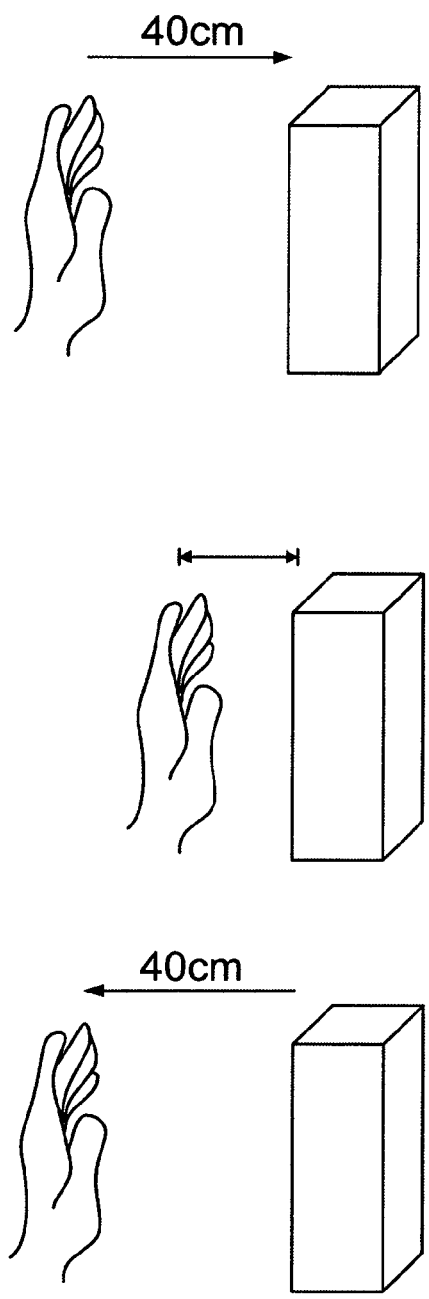
FIG. 7 illustrates a motion gesture with respect to an example sensor.

The gesture channel will also have a phase response to movement of the target (e.g., a person's hand etc.). The phase difference between the I and Q channels is 90 degrees. As a result the Lissajous curve for the I and Q signal is a circle, as shown in FIG. 4. The frequency (cycle time) is determined by the target speed. The amplitude is determined by the target distance, target cross section and by the gesture channel transfer function. The direction of the phasor, clockwise or anti-clockwise, is dependent on the direction of the motion towards or away from the sensor.

The gesture channel or another, general movement dedicated, channel may also have an amplitude response to non-gesture related movement. The amplitude of its I and Q corresponding channels is determined by the target distance, target cross section and by the movement channel transfer function. By way of example, a logarithmic plot of the movement channel signal amplitude versus target distance for a fixed target and in band target speed is as shown in FIG. 5A.

FIG. 5B compares the magnitude response of two channels (movement channel and gesture channel) in response to a specific movement over distance of a different sensor from that of FIG. 5A. The gesture channel has a similar characteristic to the movement channel. FIG. 5B illustrates channel amplitude response of a version of the sensor, such as with different antialiasing filtering compared to that of FIG. 5A. Because of the radar equation and associated antenna gain transfer function, as well as a non-linear scattering of the reflected signal, the receive signal level declines as function of the distance. (e.g., 1/xn, 1.5<n<3).

Accordingly, by processing of the gesture output signal(s) from the gesture channel and/or the movement signals from the movement channel (which may or may not be the same as the gesture channel), particular gestures or movements may be detected in one or more processors. This may be accomplished by calculating features from the signal(s) and comparing the features and/or changes in the features to one or more thresholds, or identifying patterns in the signal(s). Such features of the signals may be, for example, statistical values of parameters associated with the signal(s), such as average or the median values of the signal(s) phase, amplitude and/or frequency, standard deviation of any of these values etc.

Suitable features may be determined by training of a classifier. Classification of calculated features may then serve as a basis for gesture detection with the trained classifier. For example, one or more processors may evaluate any one or more of the gesture signal(s) phase, amplitude and/or frequency characteristics to detect patterns or other indicia in the signal associated with a particular gesture or movement. In some cases, the characteristics may include amplitude cadence (e.g., amplitude and sidebands) and a time during which the gesture persists. In this regard, analysis of the signal(s) will permit identification of signal characteristics that are produced with respect to certain motions (e.g., towards or away from) in relation to the sensor since different motions may produce differently defined amplitude, frequency and/or phase characteristics. Such an analysis may include choosing a pattern for a particular gesture so as to distinguish between several gestures (e.g., select one from a group of different predetermined trained gestures.) In some cases, the system may also process feedback from the user based on a perceived correct or incorrect detection of a movement or gesture signal. The system may optionally update its classification based on this input, and may optionally prompt the user to perform one or more repetitions of a specific gesture in order to optimize performance/recognition. In this manner, the system may be configured to adapt (personalise) to the gestures of a particular user, and identify and separate (distinguish) the gestures of different users.

In this regard, fast or slow and/or long or short hand gestures towards or away from the sensor can produce clearly detectable signals. Motion across the sensor produces a motion component that is also towards and away from the sensor, but this motion component is small. Therefore motion across the sensor produces distinguishing characteristics but at smaller amplitude, lower frequency and a center line based phase change.

Motion towards the sensor always has a specific phase rotation which is reversed when the motion is away from the sensor. Phase can therefore provide gesture directional information. A frequency spectrogram may clearly show the characteristic motion velocity for particular gestures and may be identified by processing features of the spectrogram.

The amplitude characteristic may require signal conditioning before use, as the amplitude is seen to vary with position (distance from the sensor) as well as target cross section/size.

It is possible to extract the radial velocity and direction of a target. Within the sensor range (e.g. 1.8-2 m), it might be a small target near in or a larger target further away. Thus, a processor of the any one or more of velocity, change in velocity, distance, change in distance, direction, change in direction, etc., extracted from the gesture channel may also serve as characteristics for detection of particular gestures.

In general, the frequency and amplitude of the signals output from the gesture and movement channels are dependent on the baseband circuit amplification and filtering. In one version, the circuit implementing the gesture/movement transfer function may be constructed with a band pass filtered amplifier with a gain, (e.g., 9.5) and with a frequency BW (bandwidth) (e.g., approximately 160 Hz) in a desired range (e.g., approximately 0.86 Hz to 161 Hz). Such an example is illustrated in the transfer function simulation graph of FIG. 6A. This may optionally be implemented with both low pass and high pass filters.

In some versions, the gesture channel may include an antialiasing filter. The gesture channel frequency characteristics may include greater or lesser antialiasing filtering. As shown in this particular example, there is less than 10% drop in signal level (6.7 to 6.1 drop in gain) at the band edge of 160 Hz. In some cases, the antialiasing filtering may be implemented by the band pass filter described in the above paragraph.

In some cases, a processor may calculate time difference or phase difference between the emitted and the received signals of the sensor and identify particular motions/gestures based on the calculated time difference and/or phase difference.

In the following, example gesture detection is described in reference to certain gestures/motions, such as hand and/or arm movement that may be trained in a system, such as for detection with a classifier executed by a processor. Other gestures may also be trained.

For example, in some versions, a group of processing methodologies (e.g., algorithm processing steps) and associated digital signal processing may be implemented for determining physiological repetitive and/or varying motion, including that caused by the movement of chest due to respiration, sway detection and cancellation, and gross and fine movement detection (gesture detection) due to a multitude of actions such movement of the hands and arms, shaving (e.g., of the face) or scratching (e.g., due to physical irritation or discomfort). The key input features to such a system are derived from any one or more of amplitude (temporal), frequency and phase characteristics of the detected signal.

In essence, the processing applied allows the unraveling of the direction change information from the in phase (I) and quadrature phase (Q) signals in the presence of significant noise and confounding components (due to the sensor's inherent noise, sensor signal "fold-over" (dependent on frequency), sensor phase imbalance (if present), different type of physiological movement, and other motion sources and background clutter). The processed channel signals (in phase and quadrature) may be recorded by a radio frequency RADAR and may be digitised using a suitable ADC module. These RF signals can be continuous wave, pulsed (e.g., applied to 10.525 GHz sensor or others) or pulsed continuous wave.

The signals may be fed or input into a filter bank, where a series of digital filters including bandpass filtering are applied to detect and remove low frequency sway information.

The phase information in the two channels may be compared to produce a clockwise/anti-clockwise pattern. Hysteresis and glitch detection may be applied to suppress signal fold-over, and the resulting signal represents the relative direction of the movement source to the sensor frame of reference. Peak/trough detection and signal following may be additionally implemented to aid this processing. Therefore, the system can determine if a movement is directed towards or away from the sensor, and if changing direction.

The analog filtering on the sensor can be modified to widen the bandwidth prior to sampling in some versions.

Example Gestures/Movements

Figure 8:
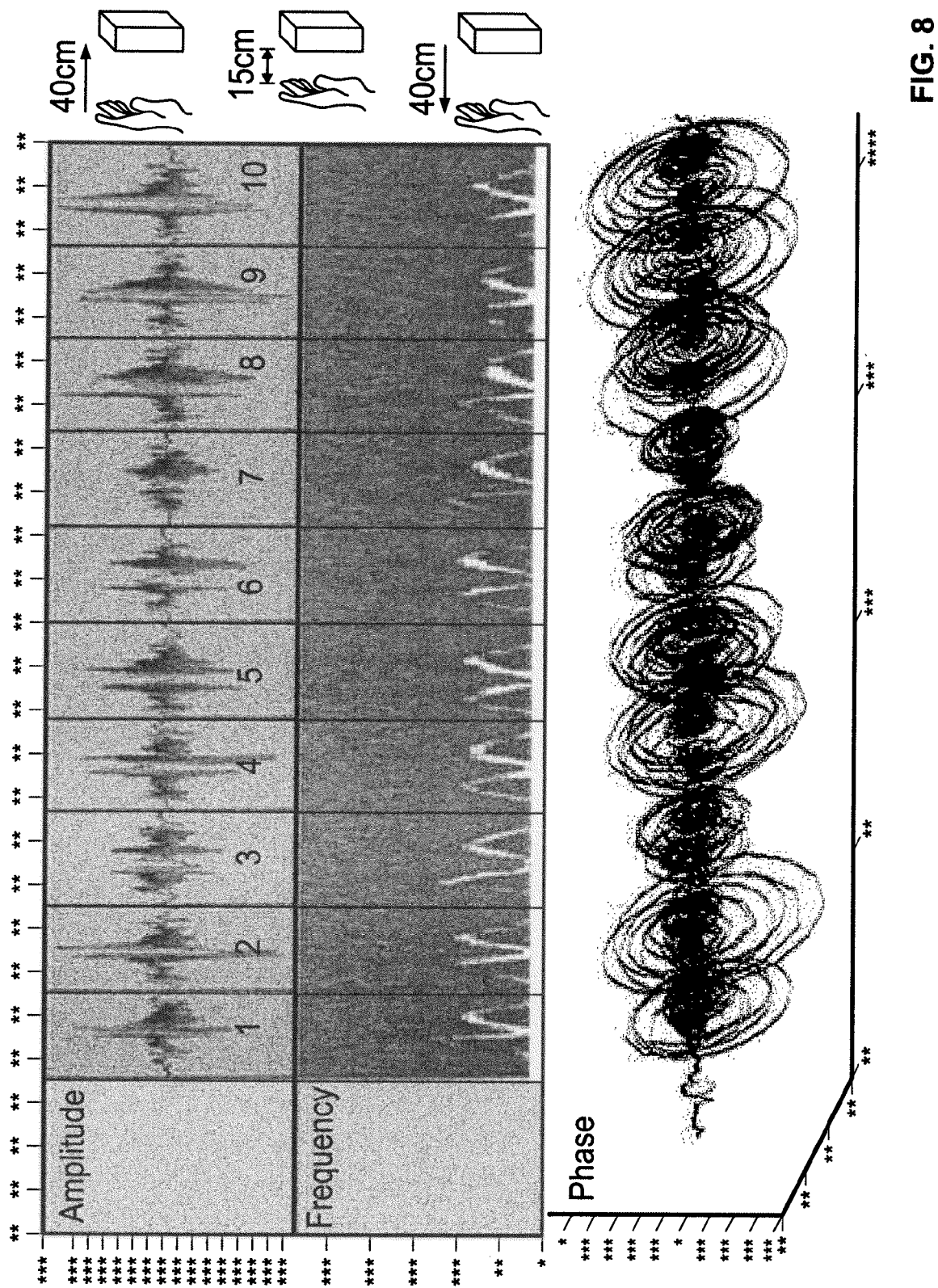

Gesture A:

Detectable Gesture A may be considered in reference to FIGS. 7-10. In example A, the gesture is based on hand movement, such as when a person sits approximately 70 cm in front of the sensor. The movement begins with the palm of the hand (face up or forward facing the sensor) approximately 40 cm from the sensor. This was the furthest point during the gross motion. The closest point may be approximately 15 cm. The hand is extended (moves) towards the sensor (taking 1 second) and after a brief pause is pulled back (taking 1 second). The movement may be considered as a replication of a sine wave. The complete gesture takes approximately 2 seconds. Sensor recordings from the gesture channel are shown with respect to repetition of the single gesture (10 times in FIG. 8 and a single time in FIG. 9). FIG. 8 illustrates a plot of changing amplitude verses time, frequency (spectrogram) and changing phase data with respect to time of the sensor recordings from the gesture channel. The phase direction may be plotted with respect to time by applying the I and Q signal outputs to different axis as illustrated in FIGS. 8, 9 and 10.

FIGS. 8-10 show in reference to the gesture A that motion towards the sensor has a specific phase rotation which is reversed when the motion is away from the sensor. Thus, analysis of this phase can provide gesture directional information.

The frequency spectrogram clearly shows the characteristic motion velocity for the gesture. This frequency "chirp" has a distinct personality (i.e., can be classified in a processor). FIG. 9 depicts a close-up view of the motion/gesture outlined in FIG. 7. FIG. 8 depicts multiple instances of this gesture; the time domain signal amplitude is shown, as well as a spectrogram, and a phase plot. The spectrogram indicates time on the x-axis, frequency on the y-axis, and intensity at a particular time for a particular frequency as a different colour. In this example, the subject sat approximately 70 cm in front of the sensor. The movement begins with the palm of the hand (face up) 40 cm from the sensor, the furthest point during the gross motion. The closest point was 15 cm. The hand is extended towards the sensor (1 second) and after a brief pause is pulled back (1 second). The intention was to replicate a sine wave. The complete gesture took 2 seconds. The complete gesture was repeated 10 times (as per FIG. 8). FIG. 9 indicates where the movement is towards the sensor, close to the sensor, then moving away from the sensor. For this case, the maximum frequency is seen to range from 90-100 Hz. The phase is seen to move clockwise during motion towards the sensor, and anti-clockwise when moving away. In FIG. 10, the I and Q (in phase and quadrature) channels were plotted against time on a 3D figure using MATLAB (The Mathworks, Natick) as the second method of analysis for phase direction.

The amplitude characteristic may employ signal conditioning before use, as the amplitude is seen to vary with position (distance from the sensor) as well as target cross section/size.

The radial velocity and direction of a target may also be extracted. Within the sensor range (e.g., 2 m), it (the target) might be a small target near in or a larger target further away.

Gesture B

Figure 12:
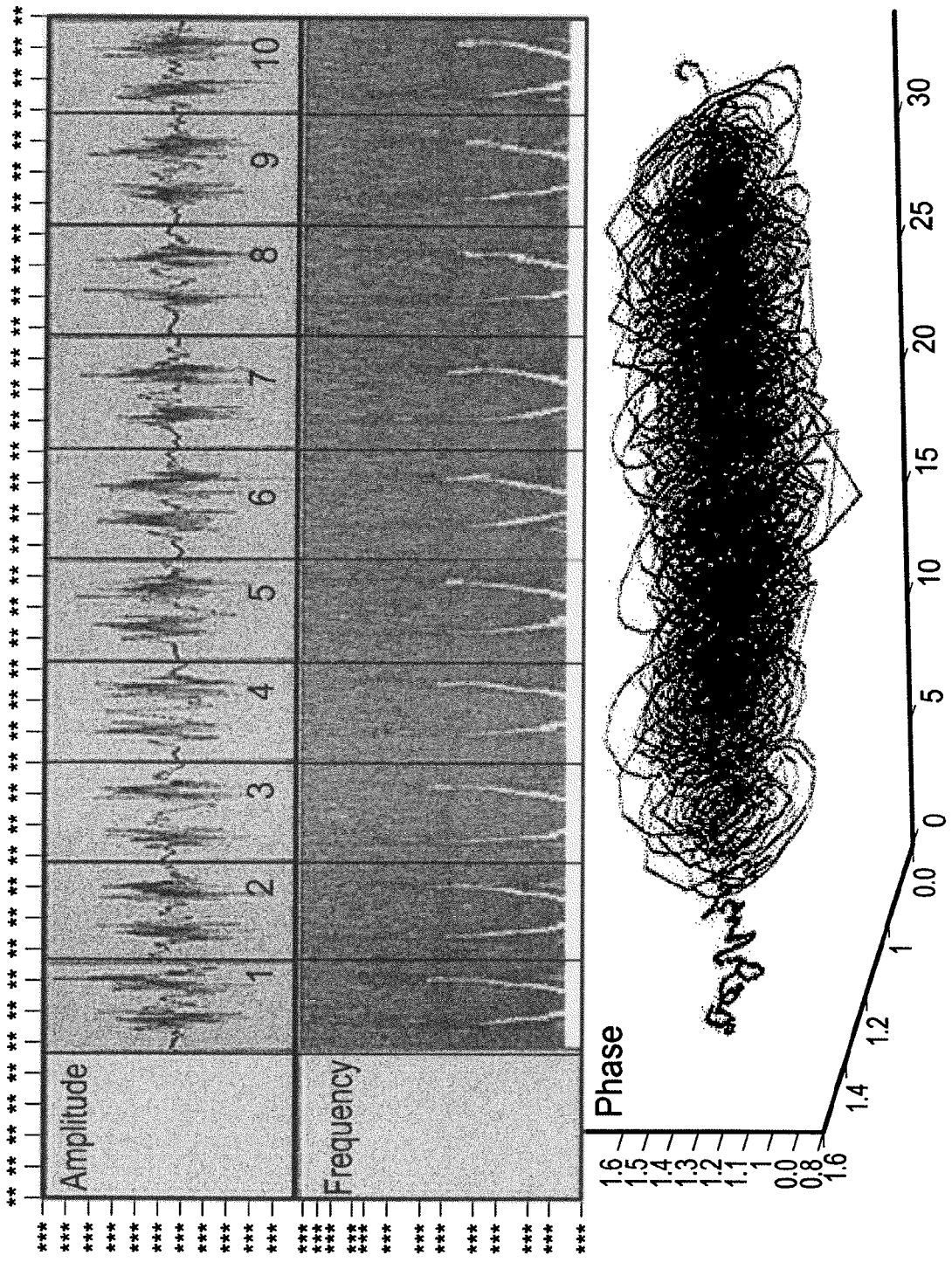
FIG. 12 illustrates amplitude, frequency and phases responses for the repeated motion gesture of FIG. 11.

Another detectable gesture B (arm and hand) may be considered in reference to FIGS. 11-12. Movement begins with the arm fully extended. As shown in FIG. 11, a hand is then swung completely across the body. The palm naturally changes from face up to face down as the arm is moved from close to the sensor (5 cm) to furthest away from the sensor (135 cm). At the midway point of the gesture (at the peak of the arm swing arc over the head) the palm direction will change.

The complete gesture takes less than 4 seconds and may, for example, be performed in a sitting position.

The gesture B with an approximately 2 m/s velocity produces a frequency of 140 Hz. This occurs within a 1 m distance over a 1 second period with a start and end velocity of 0 m/s.

The sensor may be positioned approximately near the person for detection (e.g., 95 cm from the center of the chest). For example, a furthest point during the gross motion of the gesture may be about 135 cm from the sensor and the closest point may be about 5 cm. Such closest and furthest points may be considered in reference to a measurement from the finger tips. FIG. 12 illustrates the amplitude, frequency and phase characteristics that may be processed for detection of the gesture.

Shaving Motions

The system may be applied for many types of activity, preferably associated with repeating motions. Examples can include detecting and classifying activities such as rinsing, combing, brushing (e.g., hair or teeth) or shaving strokes, etc. In some cases, the system may assume that the primary motions recorded contain a particular activity (e.g., shaving information and/or rinsing). Analysis of the gesture channel can permit, for example, estimating total number of strokes, detecting the change in direction of the motion may be determined. Similarly, relative direction of stroke—up/down or down/other, etc. may be determined. The relative direction of the motion source may be detected. Rate of stroke may be determined.

By detecting a likely stroke event, it is possible to calculate and provide an estimate of the rate in strokes per minute. Peak high rate events are marked as possible rinse events.

In some versions of the system an activity type or gesture processor may implement any one or more of the following Processing steps:

Calculate spectral content of gesture signal(s)
apply Fast Fourier transform and find peak (frequency domain) in a rolling window
Calculate the distance between each sinusoidal-like peak
Calculate zero crossings of signal (time domain)
Estimate relative direction of movement and duration
Extract phase shift between the two channels.
Alternative time frequency analysis such as short time Fourier transform or wavelets may also be implemented.

In general, the complex sensor signal is based on arm movement, head movement, torso movement etc. Other movements may also be detected.

In some versions, the clockwise/anti-clockwise direction change information may be clocked to produce an impulse to represent a change in direction. These pulses may be implemented for a counter, and grouped into different rates of occurrence. FIG. 13 illustrates the change in direction for detection as I/Q phase signal difference varies.

Therefore, typical rates consistent with the act of shaving can be noted, and thus the period of shaving deduced. An increase in rate associated with excess high frequency information can be inferred as the arm moving to the face, or the rinsing of a razor blade.

An advantage of using an RF sensor for detecting of shaving or other motions and gestures is the enhanced privacy versus say a video based system that captures or processes pictures/video from a user or group of users.

A reduction in rate and direction change can be used to detect breathing. In addition, time domain and frequency domain processing is applied to the signals to localize specific bands.

Breathing can be further separated from confounding human body sway by detecting a relative change in rate with an unexpected direction change behaviour characteristic. FIG. 13 illustrates change in direction detection as I/Q phase difference varies. In FIG. 13, the IQ plot in the upper left panel represents a trace moving in a clockwise direction, and upper left showing a trace moving in an anti-clockwise direction. A change from a clockwise to anti-clockwise direction (or vice versa) gives rise to the direction change trace shown in the lower left and right panels by the top line therein. The middle and bottom lines represent either the I or Q channels respectively in this example.

In one example version, strokes of the activity, (e.g., shaving strokes) may be counted with application of processing that includes the following Band pass filtering
Calculating the change of state from clockwise/anticlockwise.
Applying hysteresis (avoid flipping state on small blips in signal, e.g., foldover).
Suppressing feature update around the zero point
Differentiating the resulting signal.
Counting the number of transitions (e.g., to identify a return stroke).

Figure 14:
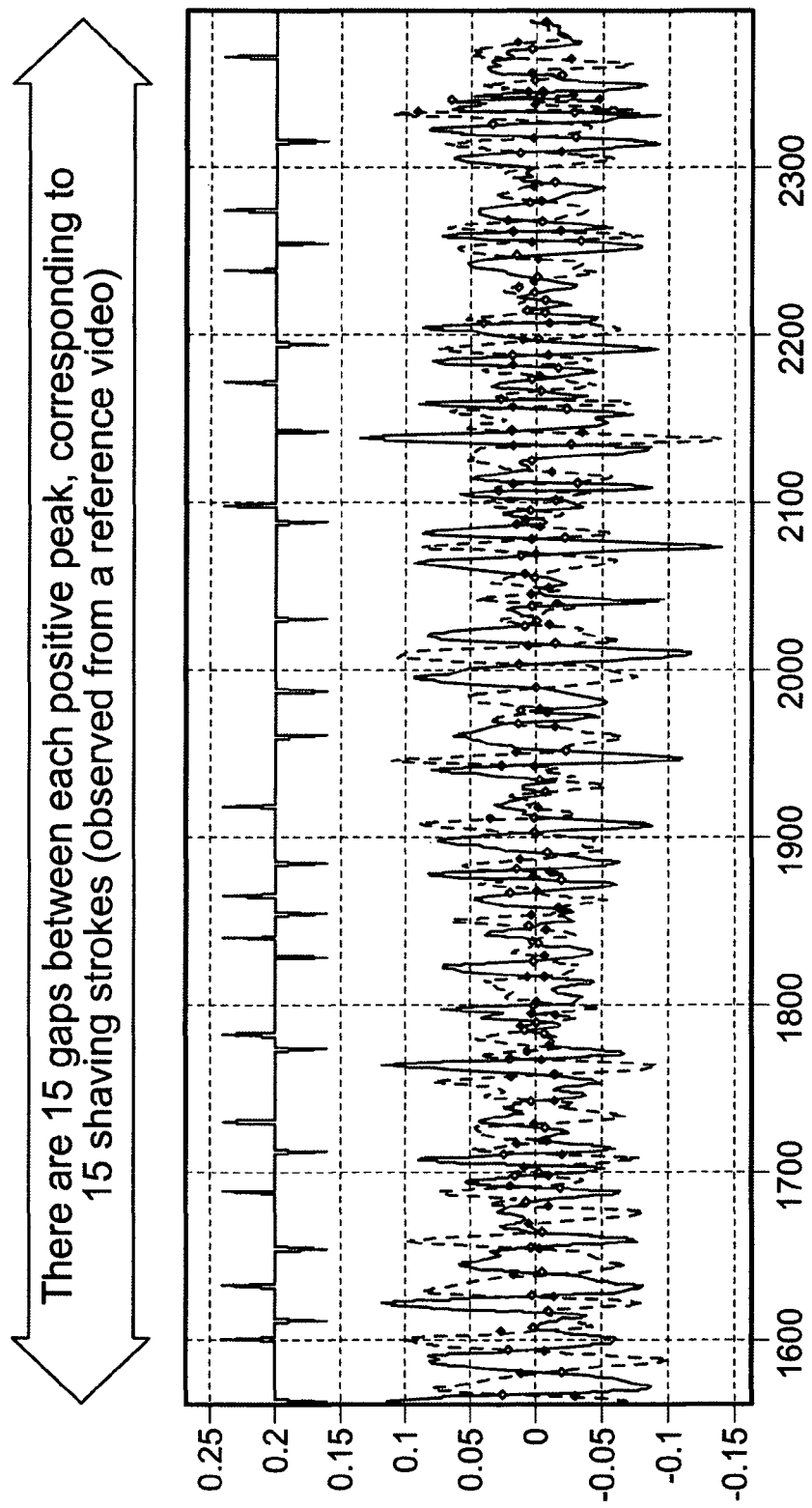
FIG. 14 illustrates a counting activity stroke methodology, such as with zero crossing detection.

A signal graph illustrating such detection processing is shown in FIG. 14.

Figure 15:
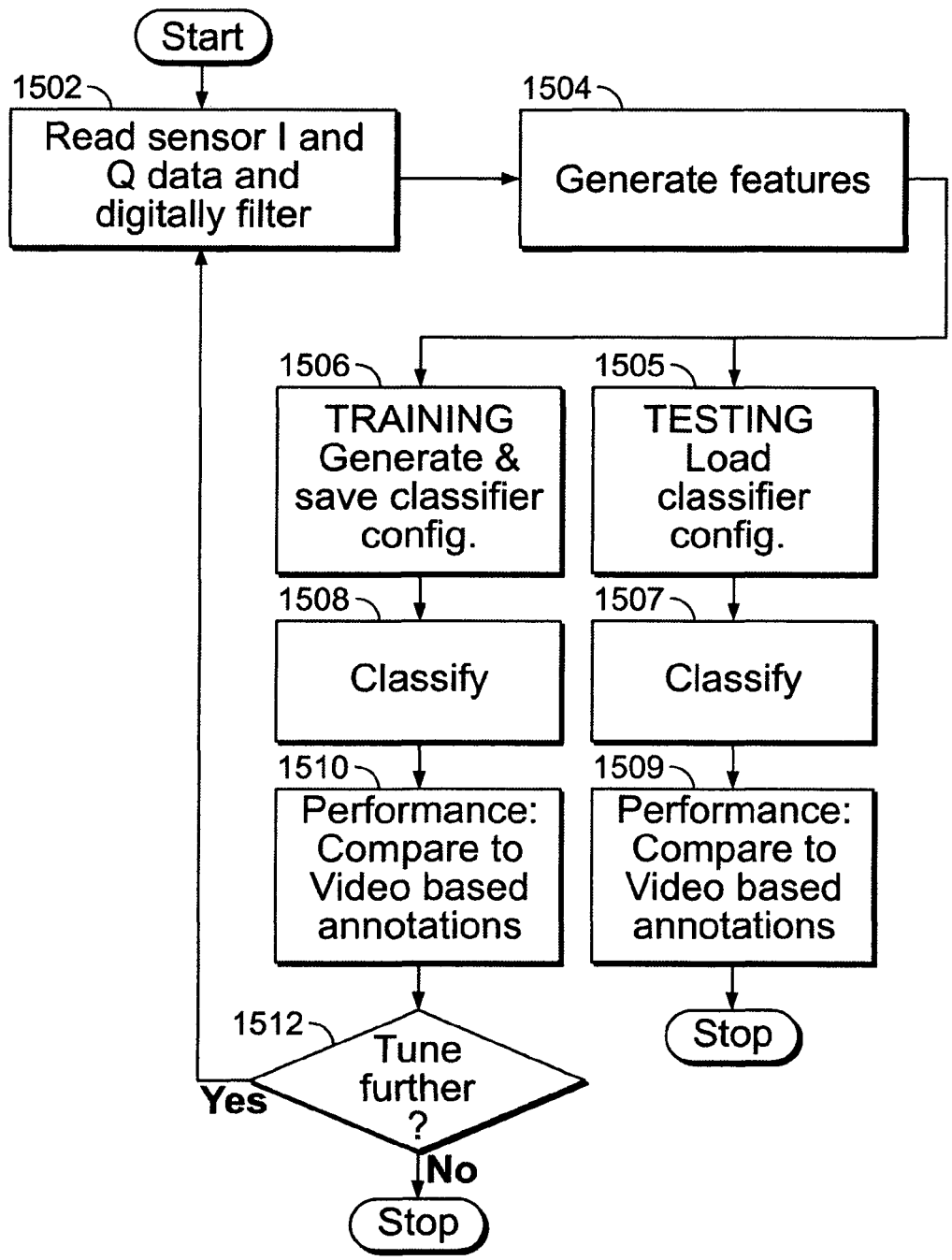
FIG. 15 illustrates a training processing methodology for activity detection involving block based classification.

In executing such gesture/activity detecting training, classification may be performed in the following manner as illustrated in FIG. 15. One set of recordings from the sensor may be accessed in a read step 1502, may be used as a training set. Suitable detection features (with phase, frequency and amplitude) may be produced, such as in a feature generation step 1504. In a training setup step 1506, a classifier configuration may be created for particular motions/gestures. The features may then be processed in a training classify step 1508 to relate a motion to the most relevant of the calculated features. The training classifying may be repeated if further tuning is desired at check step 1512, such as if improved classification training is desired. In a pre-testing setup step 1505, a classifier configuration may be accessed for evaluating features of previously classified motions/gestures. These pre-classified motions may then be compared with newly generated features in a classification step 1507 to identify one of the pre-classified motions based on the features. Optionally, the performance of the classifier from training or testing may be assessed in video performance step 1510, 1509 using the identified features to compare with video based annotations (i.e., where a simultaneous video is recorded during performance of known gestures to act as a timestamp reference for later annotation of the motion signals; this requires human scoring of the signals and/or a separate log of motion/gesture events to be performed) and, based on the result of the comparison, the features may need to be fine-tuned. An independent test set may then be used to test the resulting configuration of features. For this type of supervised learning (unsupervised learning is also possible using other techniques), an independent test set is held back from the training set in order to check the likely real world performance of a system (i.e., the performance on unknown data). During the development process, iteration is carried out on the training set in order to maximise performance, and aims to use the minimum number of features that maximise performance where possible. Principal Component Analysis (PCA) or other dimensionality reduction may be implemented in order to select such features. It will be recognized that steps 1502, 1504, 1505 and 1507 may be implemented by a processor or controller, in or associated with a detection device 100, for the purposes of making motion identification as previously described, when not implementing training and testing.

Figure 16:
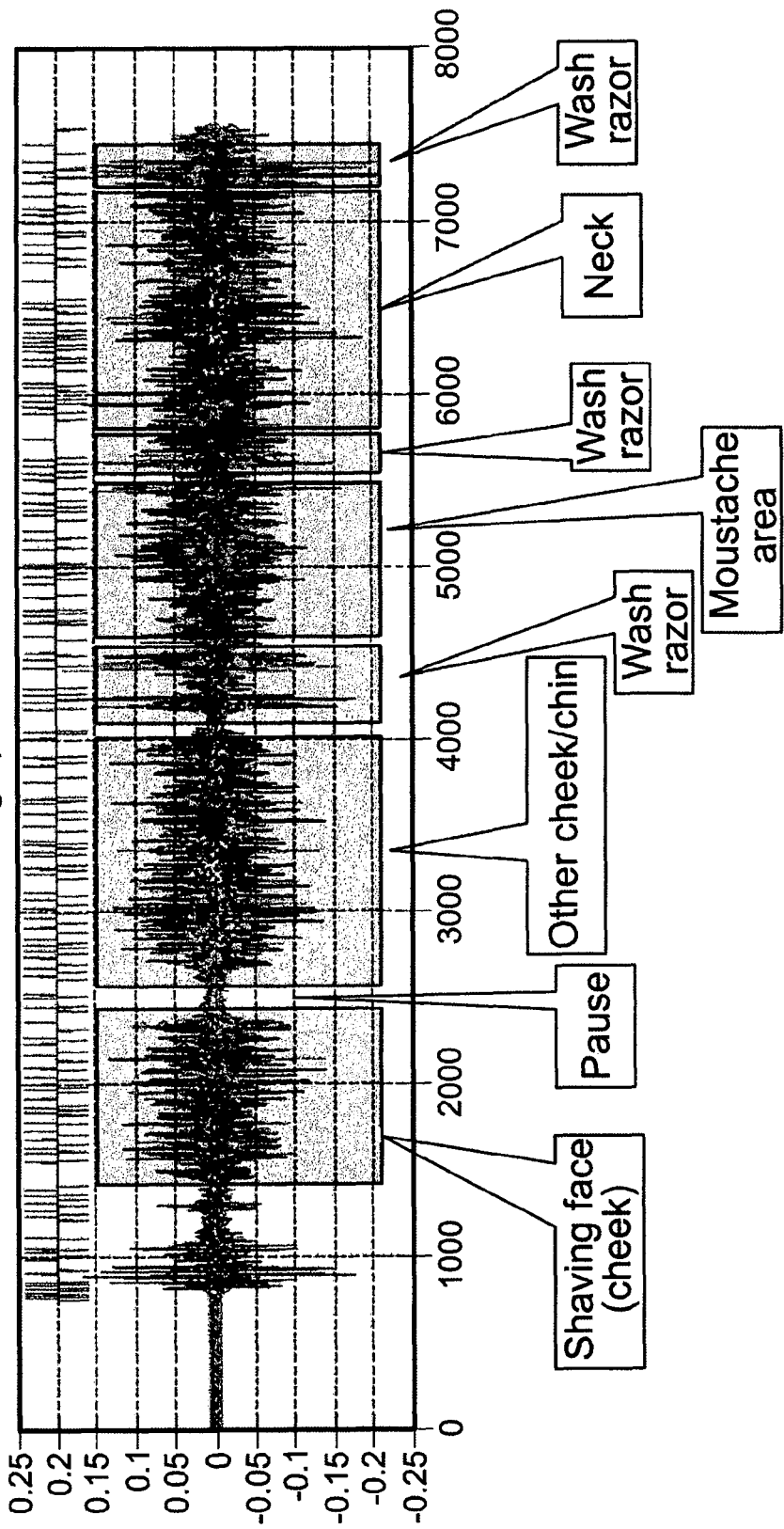
FIG. 16 illustrates block by block classification of an gesture activity signal.

For example, a Kolgomorov-Smirnov (KS) goodness-of-fit hypothesis statistical test may be implemented to compare the cumulative distribution function of the target block of data to the training data. Such a block by block classification is illustrated in the example of FIG. 16. It may be implemented with any one or more of the following processes:

(1) Biomotion Block Division

The I and Q signal data can be split up into either continuous non-overlapping or partially overlapping blocks. For example, a block length of 1*160 samples (1 seconds at 160 Hz) with a 50% overlap could be used or some other combination. Computational complexity can be traded for precision by varying the block length and/or by varying the amount of overlap.

(2) Block Pre-Processing

The block of data may be checked to see if the data falls within a presence or absence section (i.e., is there a user with a breathing rate and/or heartbeat within range of the sensor or sensors; for breathing rate detection, between 15 and 60 seconds plus of data may be required to detect multiple breathing cycles). Furthermore, the block may be checked to see that no possible RF interference signals are detected (i.e., to separate motion/gesture signals from strong sources of RF interference that might be detected by an RF transceiver; also, other non biomotion sources such as fans may be detected and rejected at this stage). If the block under consideration does not meet these criteria, it may optionally not be classified further. The block or blocks may also be cross referenced and/or correlated with other information sources of the user or the room environment, in order to check the likelihood of a user actually being in the vicinity of the sensor; for example, data from a wearable device, location or motion data from a cell phone, room environmental sensors, home automation or other security sensors.

(3) Feature Extraction

For the block under consideration, a number (either all or a subset) of time-domain (temporal) and frequency domain or time/frequency features may be calculated as follows. It is noted that different block lengths may be considered simultaneously.

transformed trimmed mean and median (said transformation being for example, but not limited to, the square root, squared or log) of the I & Q signals (or of derived features)

transformed spread in the signals (said transformation being for example, but not limited to, the square root, squared or log) calculated using interpolation or otherwise, covering a defined range (for example, but not limited to, the range from 5% to 95% or of interquartile range).

The envelope of the signal (I & Q) using a Hilbert transform

The relative amplitude of the signal (I&Q) to surrounding examples of the signal The zero crossings of the signal (I & Q)

The peak frequency in a moving window

The ratios of peak frequency to second and third harmonics

The phase direction (clockwise or anticlockwise)

The phase velocity

The existence (or lack thereof) of a breathing and/or cardiac signal in the signal (i.e., relating the motion to a biomotion, e.g., that motion made by a person)

The presence of a similar or difference in motion signal in I & Q channels (4) Block Classification As an example, for an input feature set with a characteristic distribution, the Kolgomorov Smirnov (KS) two sample non parametric goodness of fit test may be used to compare this reference sample (e.g., features of a shaving motion, particular hand gesture derived from time, frequency, phase etc.) to a new sample distribution that has been captured by the sensor(s) (e.g., quantifying a distance between the empirical distribution function of the new sample detected and the cumulative distribution function of the reference distribution). A multivariate version of the KS may also be implemented, although this may require multiple cumulate density function comparisons to be made.

As another example, a linear discriminant classifier (LDC), based on Fisher's linear discriminant rule, is applied to each non-overlapped or overlapped block. For each block of data fed in, there are multiple predetermined output classes—e.g., different motion or gesture states. The classifier outputs a set of numbers representing the probability estimate of each class, in response to a set of input features. Linear discriminants partition the feature space into different classes using a set of hyper-planes. Optimisation of the model is achieved through direct calculation and is extremely fast relative to other models such as neural networks.

The training of a LDC proceeds as follows. Let x be a dx 1 column vector containing feature values calculated from a data set. We wish to assign x to one of c possible classes (c=2 in our case). A total of N feature vectors are available for training the classifier, with the number of feature vectors representing class k equal to $N_k$, i.e.:

$$N = \sum_k N_k \tag{1}$$

The $n^{th}$ training vector in class k is denoted as $x_{k,n}$. The class-conditional mean vectors $\mu_k$ are defined as:

$$\mu_k = \frac{1}{N} \sum_{n=1}^{N_k} x_{k,n} \tag{2}$$

We now define a common covariance matrix defined over all classes (i.e., we assume that each class only differs in its mean value, and not in its higher order statistics). The common covariance matrix is defined as:

$$\Sigma = \frac{1}{N-c} \sum_{k=1}^{c} \sum_{n=1}^{N_k} (x_{k,n} - \mu_k)(x_{k,n} - \mu_k)^T \tag{3}$$

The $\mu_k$'s and E are calculated using training data. Once these values have been calculated, a discriminant value $y_k$ for an arbitrary data vector x can be calculated using:

$$y_k = -\tfrac{1}{2}\mu_k^T \Sigma^{-1} \mu_k = \mu_k^T \Sigma^{-1} x + \log(\pi_k) \tag{4}$$

Where $\pi_k$ is the a priori probability of the vector x being from class k. It is easy to convert the discriminant values to posterior probabilities using:

$$p(k \mid x) = \frac{\exp(y_k)}{\sum_{k=1}^{c} \exp(y_k)} \quad (5)$$

This formulation provides a mapping from discriminant value to posterior probabilities. The final class assigned to x is the class with the highest posterior probability. This becomes the block output.

However, the system can also employ methods such as neural networks, deep learning analysis etc.—especially where reasonable computing power is available. More complex methods including morphological signal processing (e.g., such as may be used in image processing) can augment feature analysis when using more complex classification methods; these may be more appropriate for detecting patterns seen in complex motions/gestures.

Figure 17:
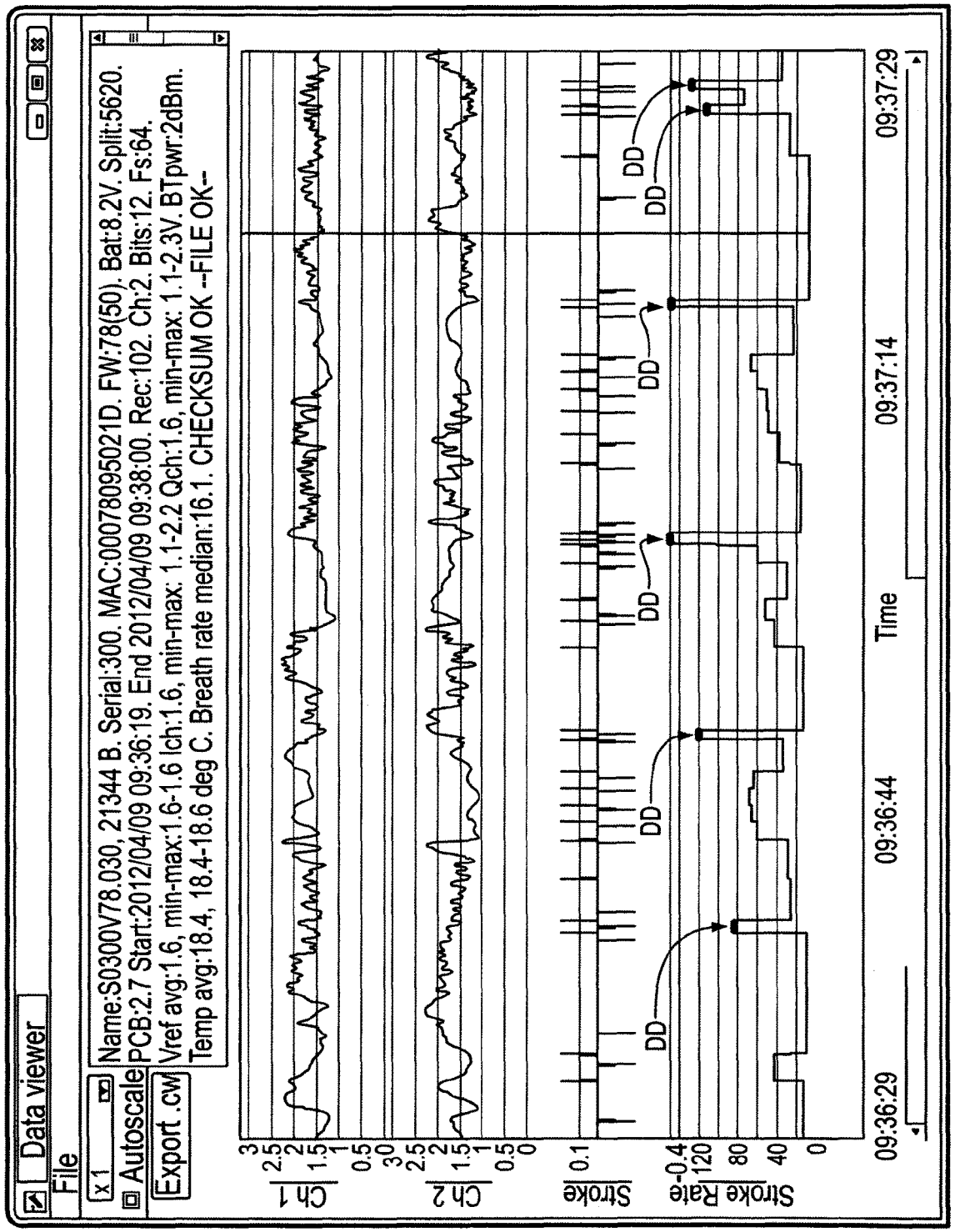
FIG. 17 show signal graphs for stroke detection and stroke rate detection.

The periodic nature of the activity is further illustrated in the signal graph of FIG. 17, showing the I channel, the Q channel, the stroke and stroke rate for the activity. In this example assuming a shaving activity, the fourth (lowest) axis depicts a probable razor rinse period with black dots (labelled "DD" in FIG. 17 in the lowest panel labelled "stroke rate"—the high rate areas indicate these rinse points). This clearly illustrates detection of the periodic nature of the shaving activity.

Further Example Gestures/Movements

As further illustrated in FIGS. 18-25 additional motion gestures may be detected by analysis of the phase, frequency and/or amplitude of the sensor gesture channel signals. Although certain distances from the sensor are provided, it will be recognized that these distances may be altered depending on the configured detection range of the sensor.

Figure 18A:
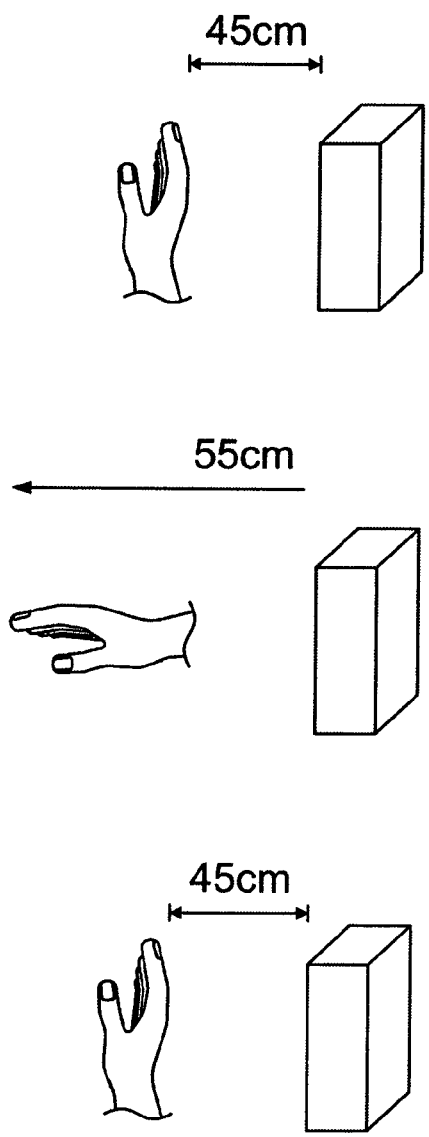
Figure 18B:
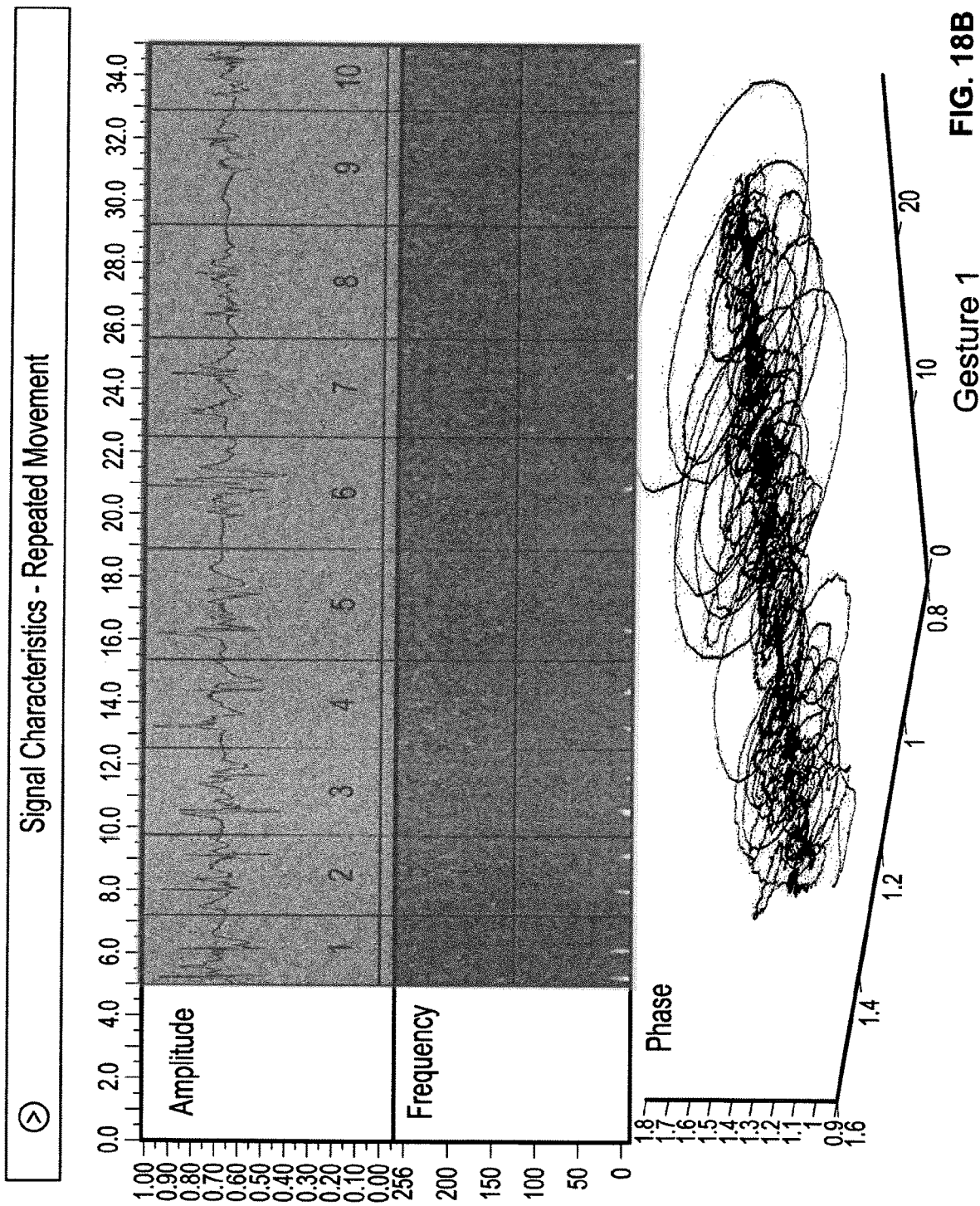

Gesture 1:

Gesture 1 may be considered in reference to FIGS. 18A-C. In this example, the sensor may be positioned a distance (e.g., 70 cm) from the centre of the chest. The sensor is spaced from the gesturing subject in the direction of the viewer of FIG. 18A (this is also the case with the subsequent FIGS. 19A, 20A, 21A, 22A, 23A and 24A). The furthest point during the gross motion may be approximately 55 cm from the sensor and the closest point may be approximately 45 cm. The furthest point may be measured in reference to the finger tips. As shown in FIG. 18A, the hand movement is performed with the arm parallel to the sensor. Only the hand moves back and forth perpendicular to the sensor. The complete gesture 1 takes approximately 2 seconds. The motion may be performed from a sitting or standing position. As illustrated in FIGS. 18B (10 repetitions of gesture) and 18C (single gesture) features of any one or more of the phase, frequency and amplitude may be classified for detection of the gesture or the repeated gesture.

Figure 19A:
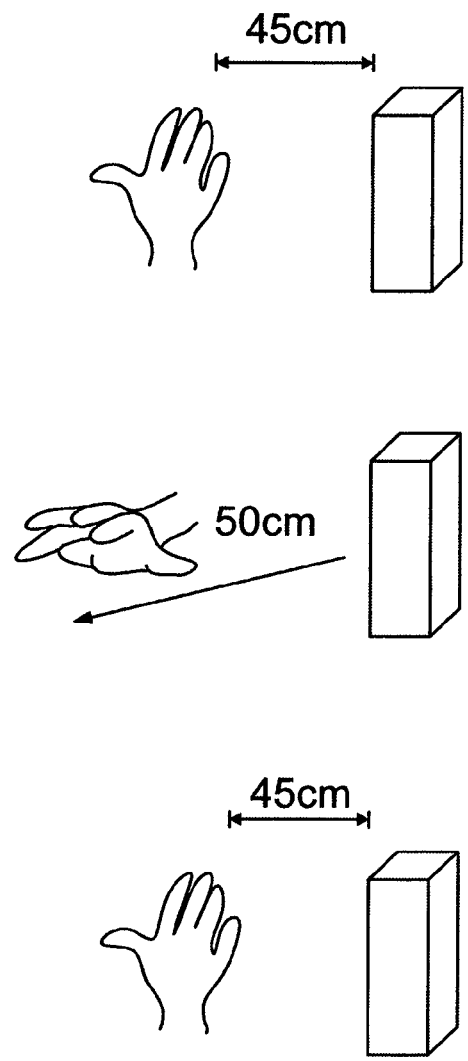
Figure 19C:
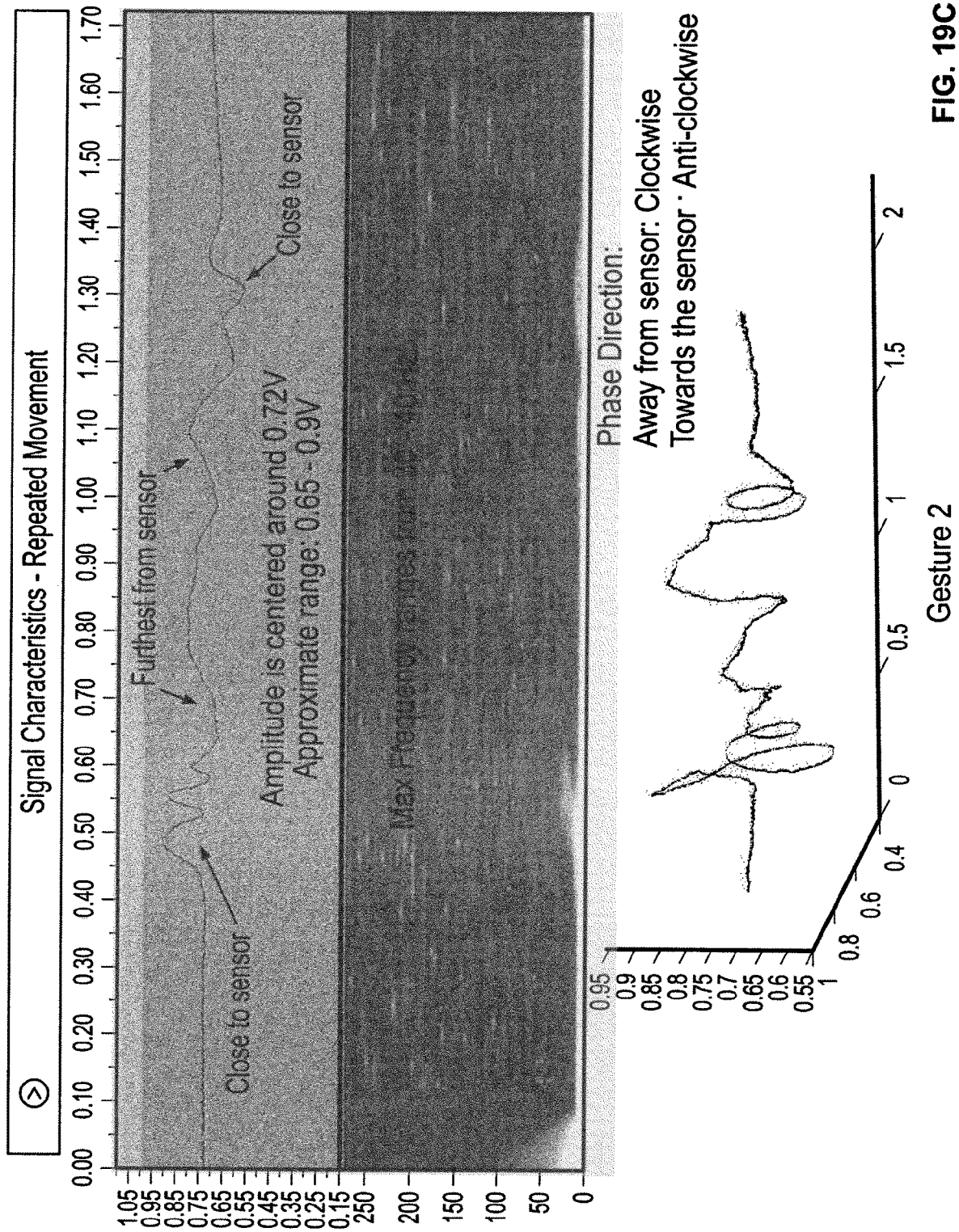

Gesture 2:

Gesture 2 may be considered in reference to FIGS. 19A-C. In this example, the sensor was positioned approximately 70 cm from the centre of the chest. The gesture may be considered waving a hand in front of the sensor. The furthest point during the gross motion was approximately 50 cm from the sensor and the closest point was approximately 45 cm. The furthest point was measured to the finger tips at an angle of approximately 24 degrees from the sensor. As illustrated in FIG. 19A, movement begins with the arm parallel to the sensor. The hand only moves back and forth, parallel to the sensor. The complete Gesture takes less than approximately 2 seconds. The motion may be performed while standing, lying or from in a sitting position.

As illustrated in FIGS. 19B (10 repetitions of gesture) and 19C (single gesture) features of any one or more of the phase, frequency and amplitude may be classified for detection of the gesture or the repeated gesture.

Figure 20A:
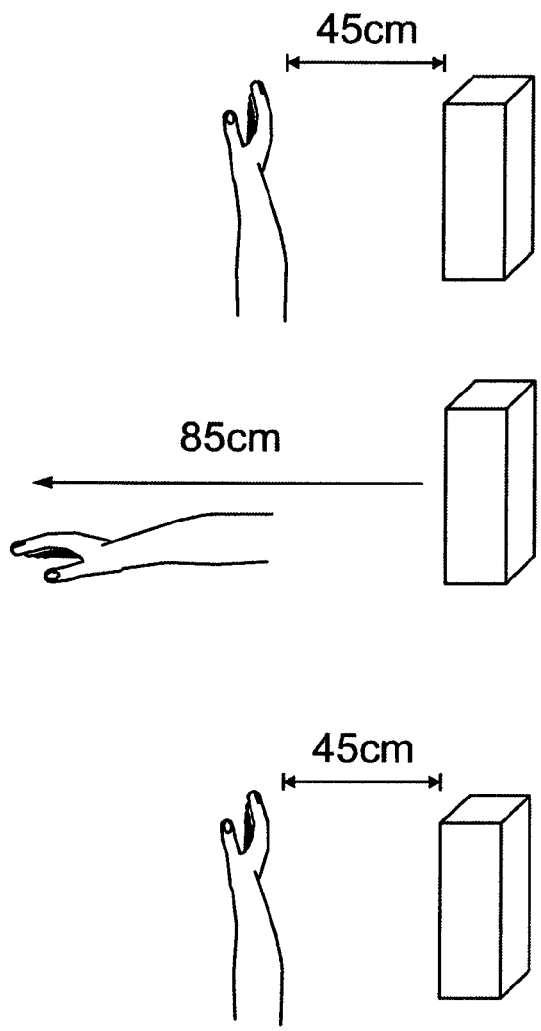
FIGS. 20A-C illustrate a further motion gesture and the amplitude, phase and frequency response by a suitable sensor to its repetition and the single movement.
Figure 20B:
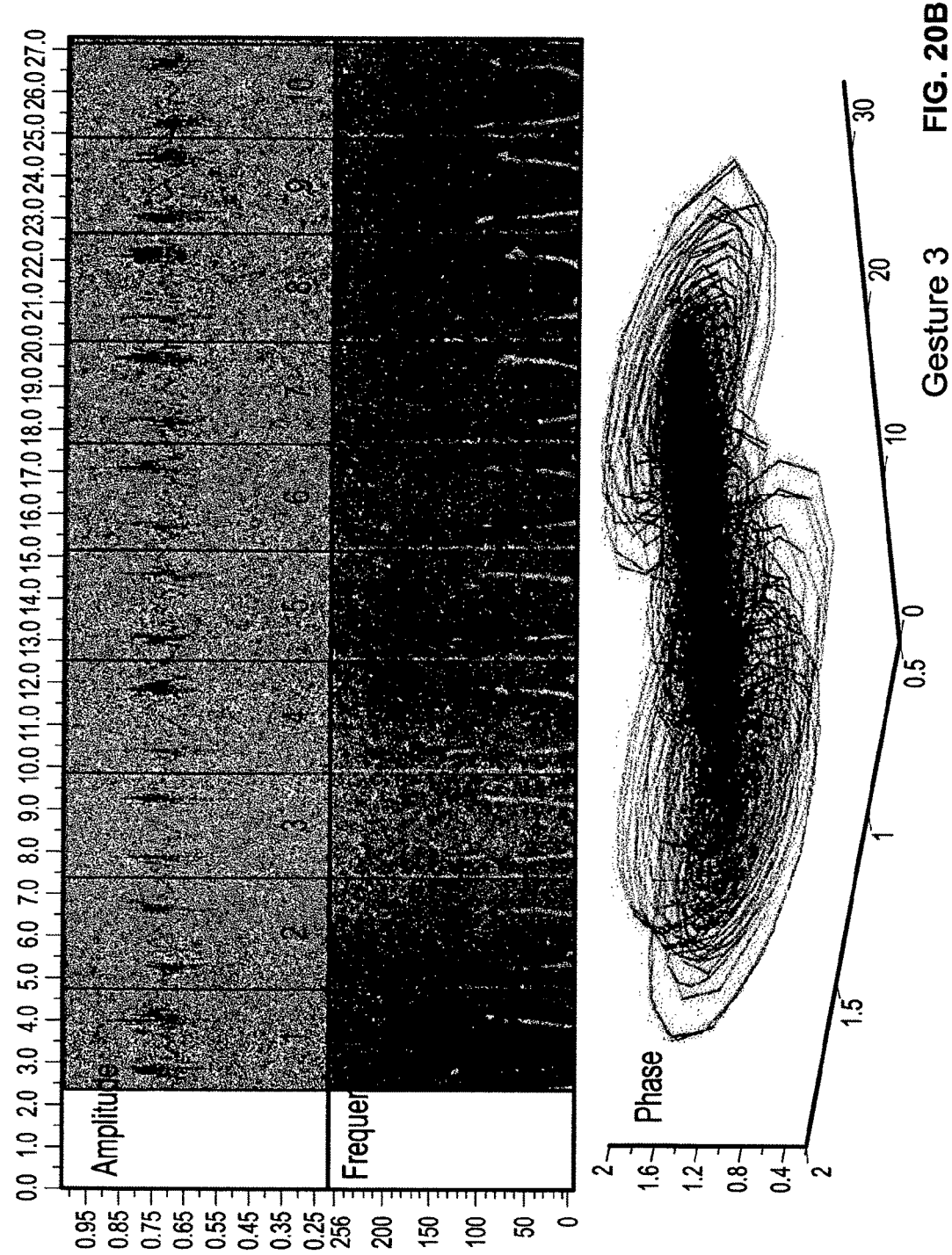
Figure 20C:
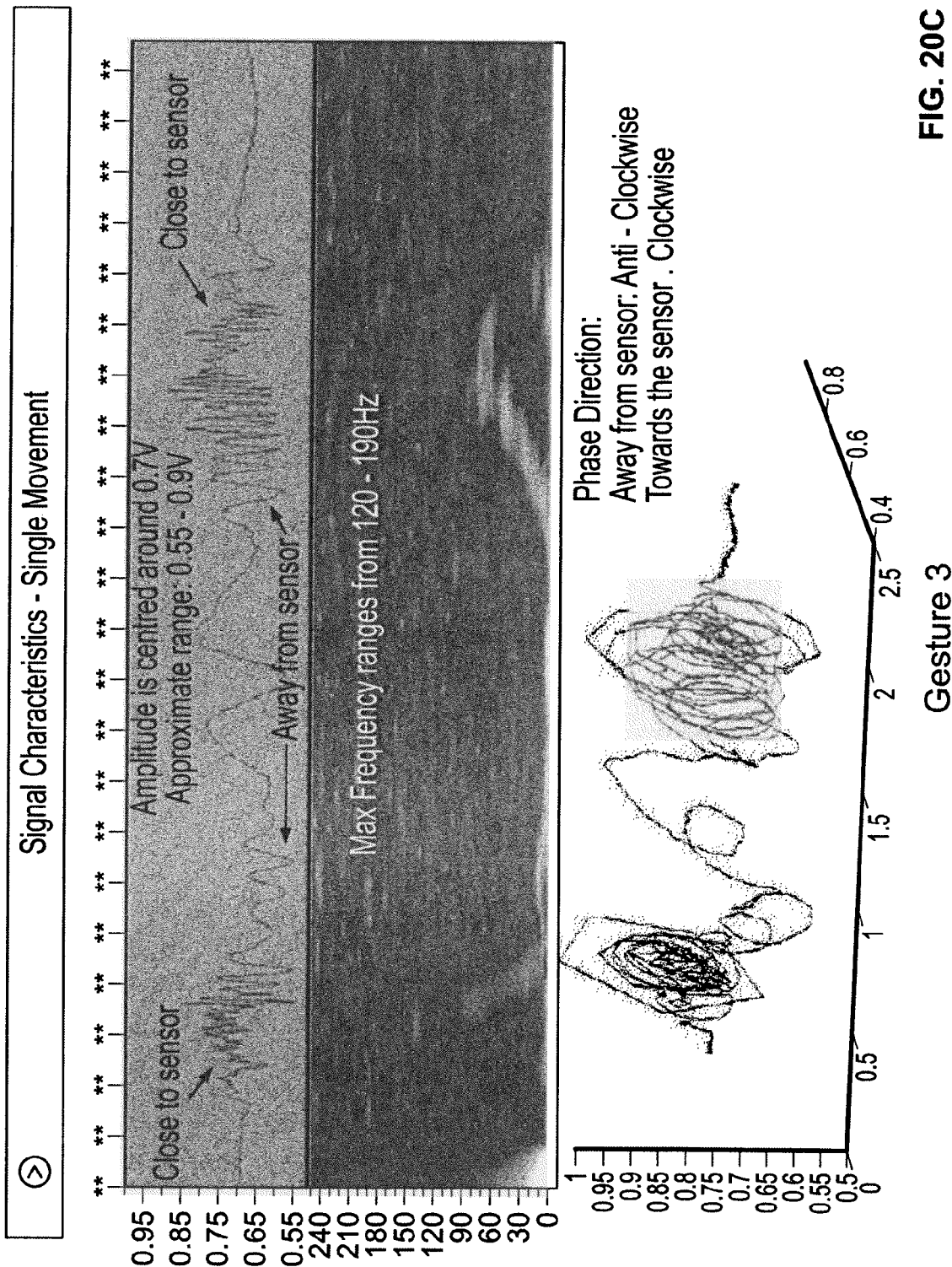

Gesture 3:

Gesture 3 may be considered in reference to FIGS. 20A-C. In this example, the sensor was positioned approximately 70 cm from the centre of the chest. The furthest point during the gross motion was approximately 85 cm from the sensor and the closest point was 45 cm. The furthest point is measured in reference to the finger tips. The closest point is the shortest distance from the sensor to arm, rather than the finger tips. As illustrated in FIG. 20A, the arm and hand movement begins with the arm parallel to the sensor. The arm is then crossed over the body before returning to the original position. The complete gesture takes approximately 2 seconds. The motion may be performed while standing, lying or from in a sitting position.

As illustrated in FIGS. 20B (10 repetitions of gesture) and 20C (single gesture) features of any one or more of the phase, frequency and amplitude may be classified for detection of the gesture or the repeated gesture.

Figure 21B:
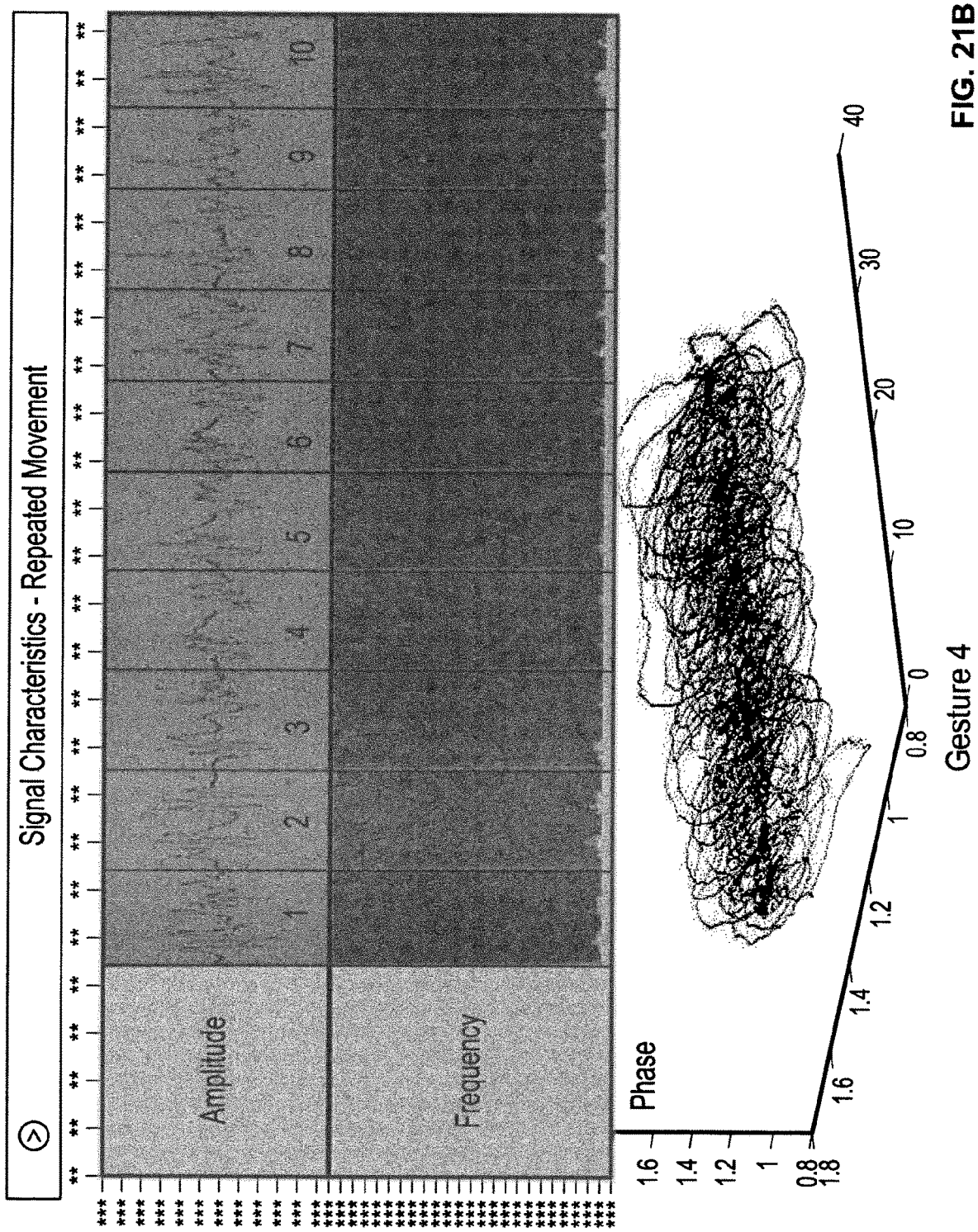
Figure 21C:
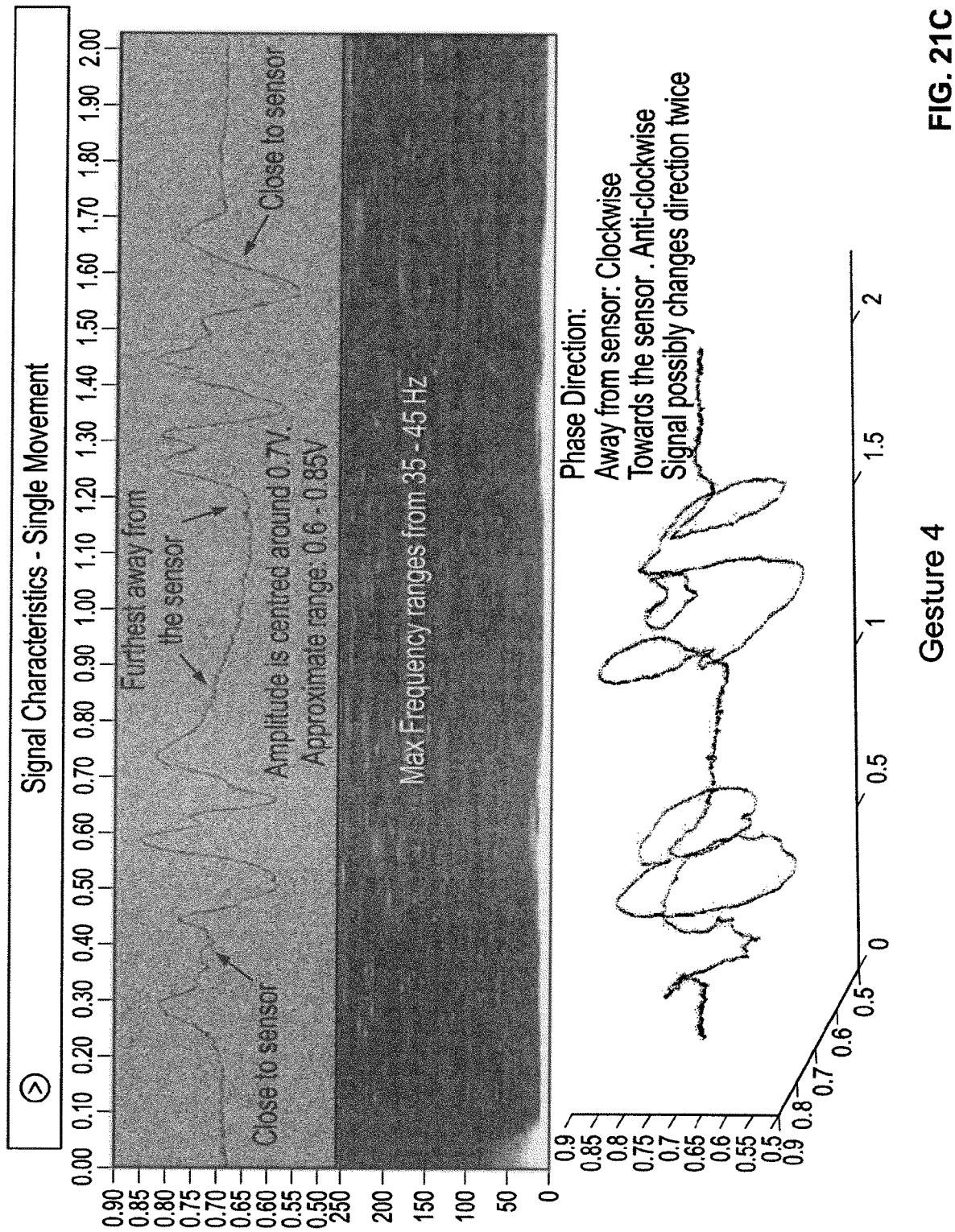

Gesture 4:

Gesture 4 may be considered in reference to FIGS. 21A-C. In this example, the sensor was positioned approximately 70 cm from the centre of the chest. The furthest point during the gross motion was approximately 60 cm from the sensor and the closest point was approximately 45 cm. The furthest point is measured in reference to the finger tips. The closest point is the shortest distance from the sensor to the arm, rather than the finger tips. As shown in FIG. 21A, the arm and hand movement begins with the arm raised, with the finger tips pointing in an upward direction, in parallel to the sensor. The arm moves in parallel to the sensor. The complete gesture takes less than approximately 2 seconds. The motion may be performed while standing, lying or from in a sitting position.

As illustrated in FIGS. 21B (10 repetitions of gesture) and 21C (single gesture) features of any one or more of the phase, frequency and amplitude may be classified for detection of the gesture or the repeated gesture.

Figure 22A:
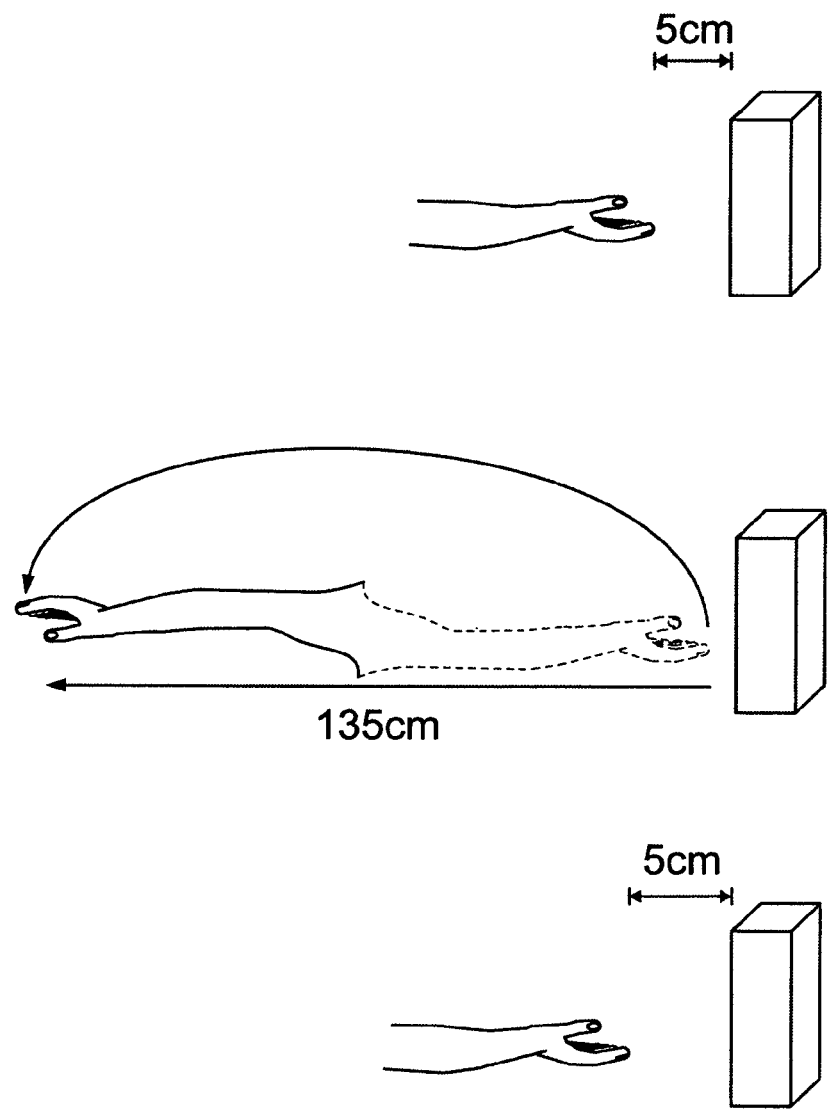
FIGS. 22A-C illustrate yet another different motion gesture and the amplitude, phase and frequency response by a suitable sensor to its repetition and the single movement.
Figure 22B:
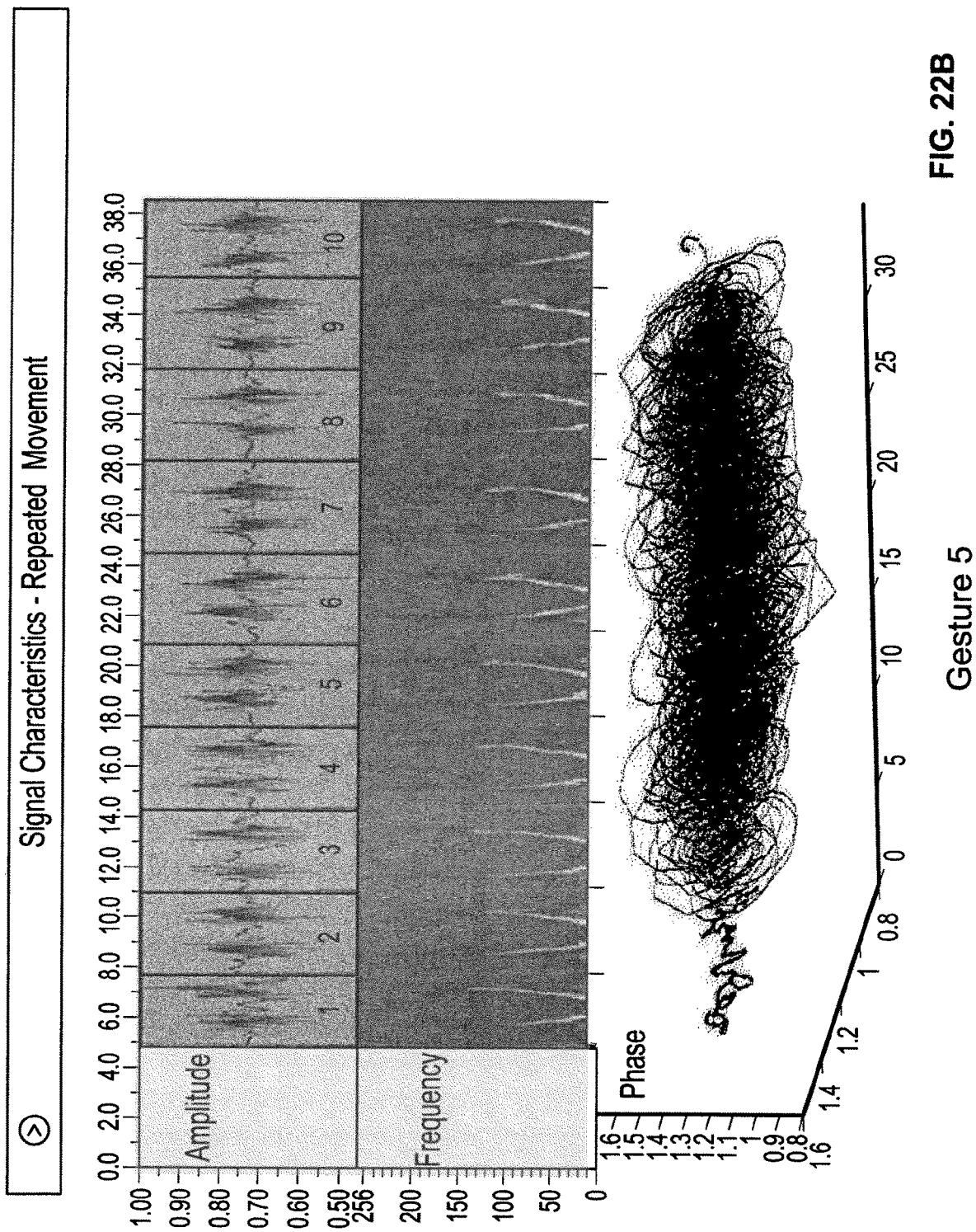
Figure 22C:
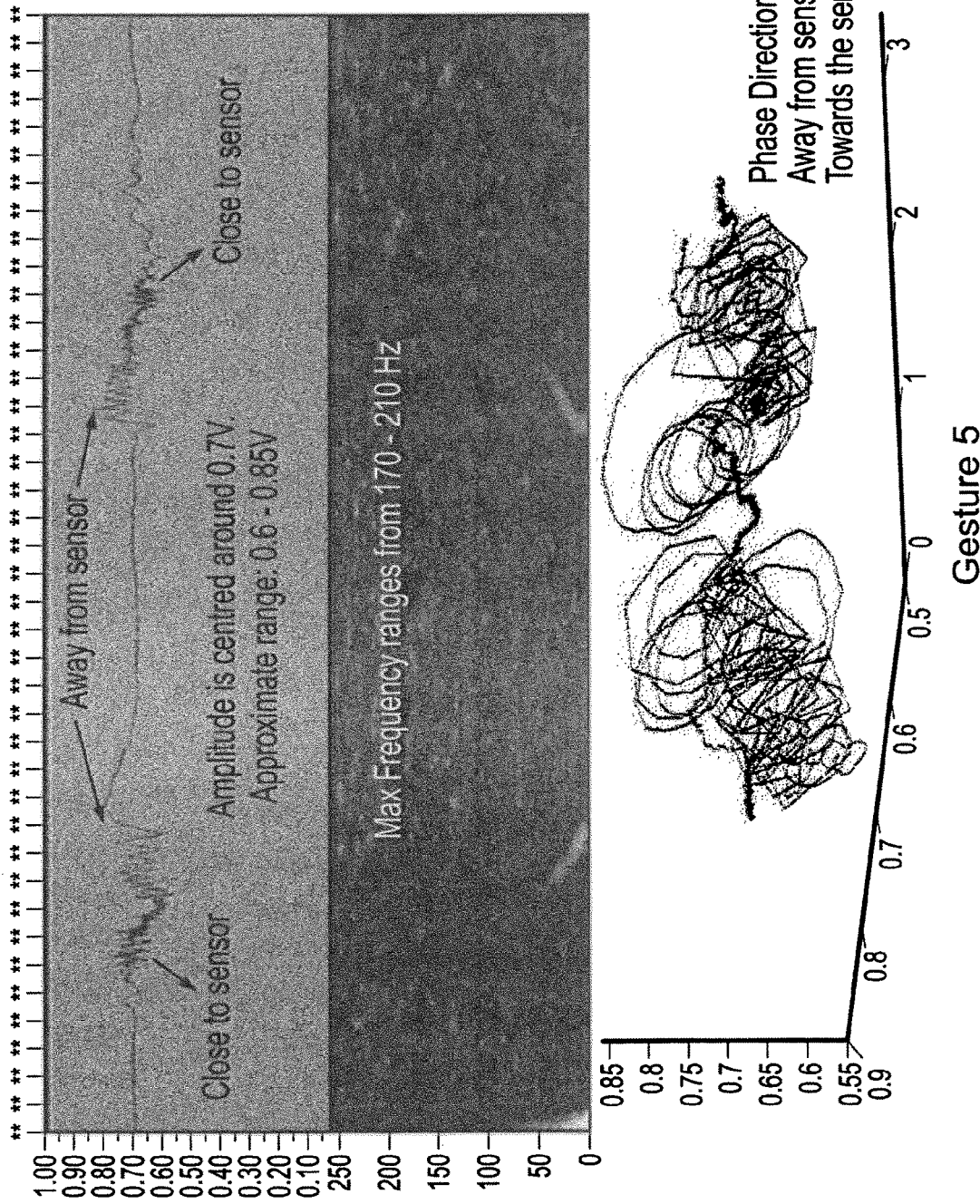

Gesture 5:

Gesture 5 may be considered in reference to FIGS. 22A-C. In this example, the sensor was positioned approximately 95 cm from the centre of the chest. The furthest point during the gross motion was approximately 135 cm from the sensor and the closest point was approximately 5 cm. The closest and furthest points are measured in reference to the finger tips. As shown in FIG. 22A, the movement begins with the arm fully extended. The hand is then swung completely across the body. The complete gesture takes less than approximately 4 seconds. The motion may be performed while standing, lying or from in a sitting position.

As illustrated in FIGS. 22B (10 repetitions of gesture) and 22C (single gesture) features of any one or more of the phase, frequency and amplitude may be classified for detection of the gesture or the repeated gesture or the repeated gesture.

Figure 23A:
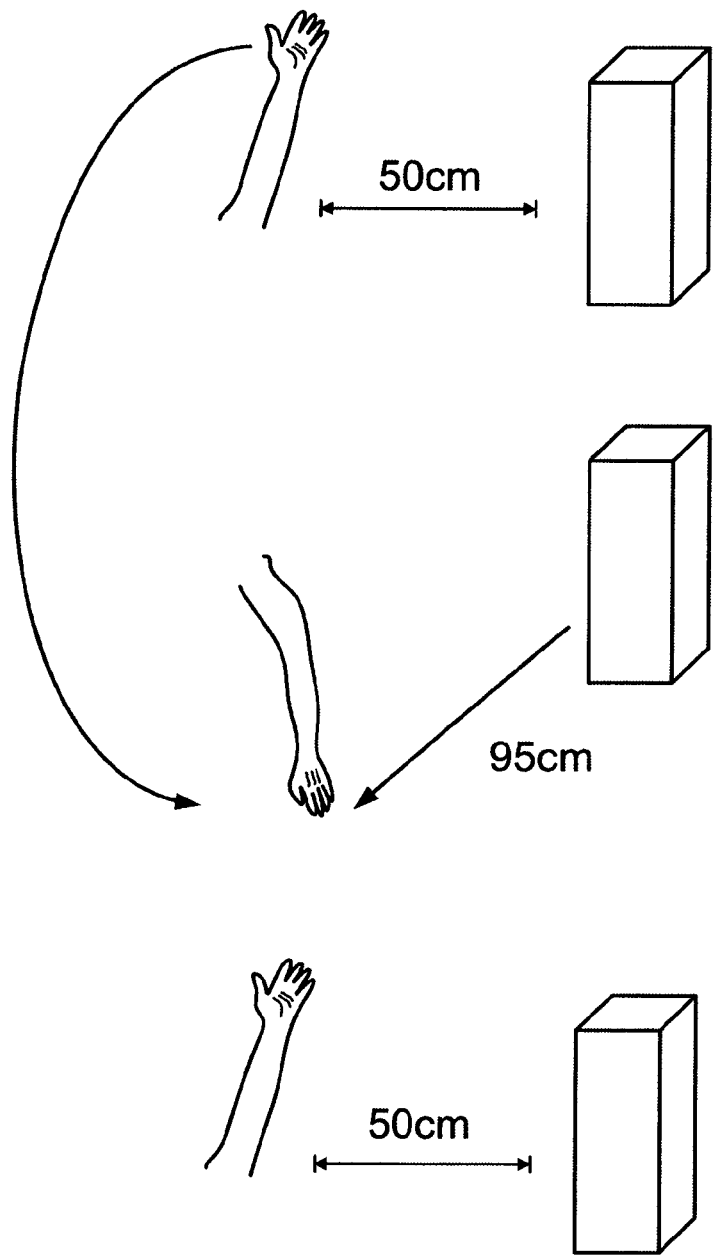
FIGS. 23A-C illustrate another motion gesture and the amplitude, phase and frequency response by a suitable sensor to its repetition and the single movement.
Figure 23B:
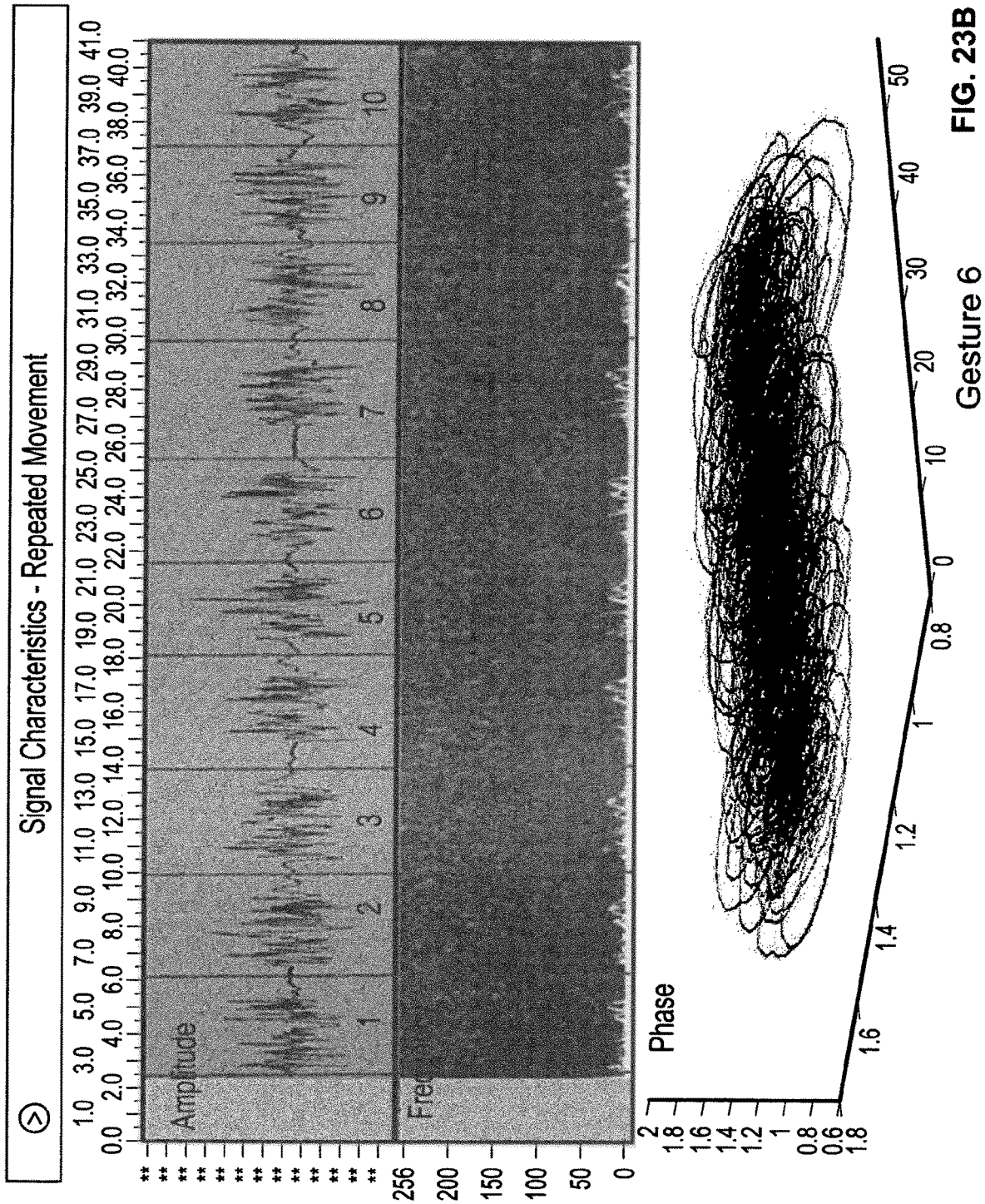
Figure 23C:
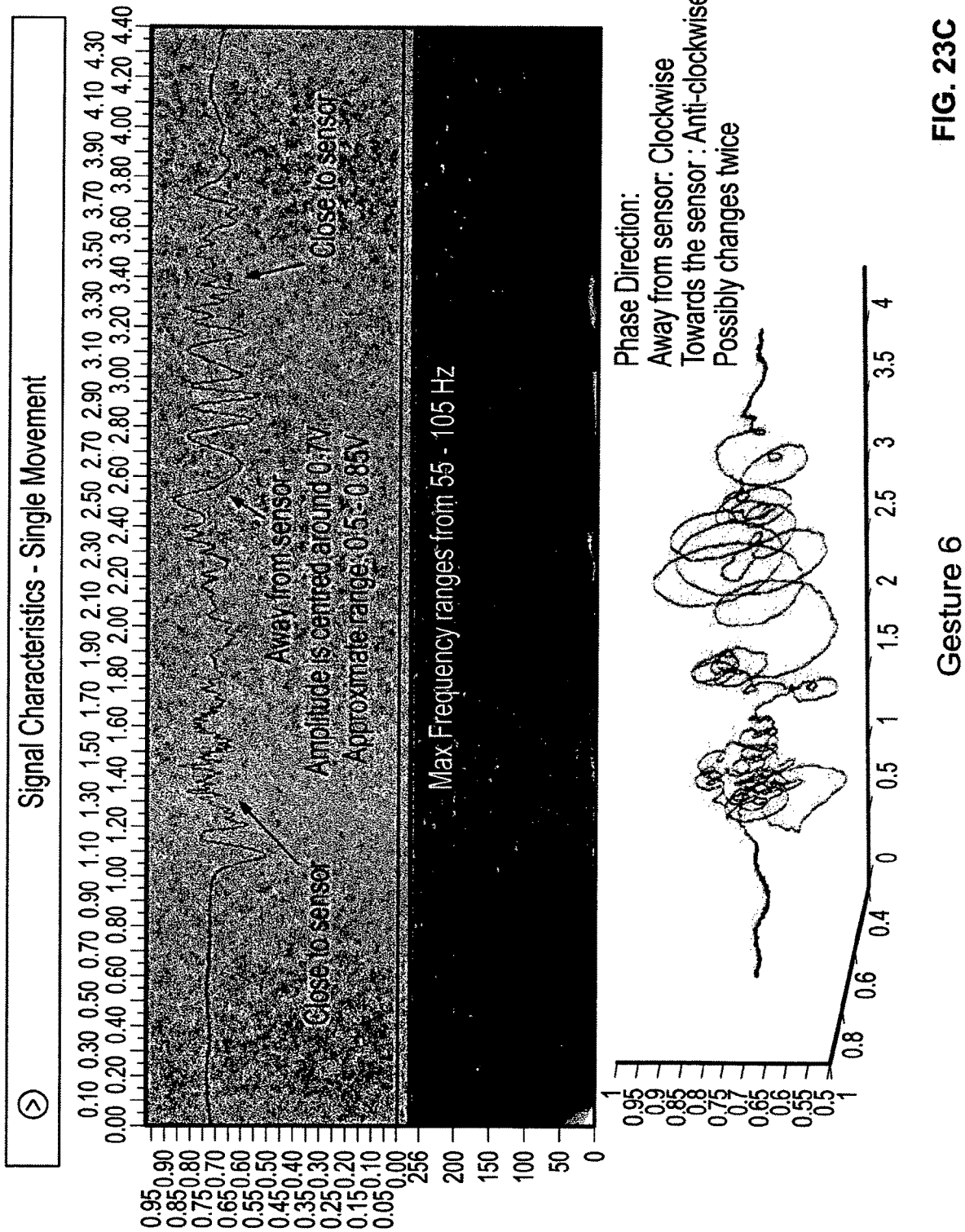

Gesture 6:

Gesture 6 may be considered in reference to FIGS. 23A-C. In this example, the sensor was positioned approximately 70 cm from the centre of the chest. The furthest point during the gross motion was approximately 95 cm from the sensor and the closest point was approximately 50 cm. The furthest point is measured in reference to the finger tips. The closest point is the shortest distance from the sensor to the shoulder, rather than the finger tips. As shown in FIG. 23A, the arm and hand movement begins with the arm fully extended, above the head. The hand is then swung down in a 90 degree angle. The complete Gesture took approximately 3 seconds. The motion may be performed while standing, lying or from in a sitting position.

As illustrated in FIGS. 23B (10 repetitions of gesture) and 23C (single gesture) features of any one or more of the phase, frequency and amplitude may be classified for detection of the gesture or the repeated gesture.

Figure 24A:
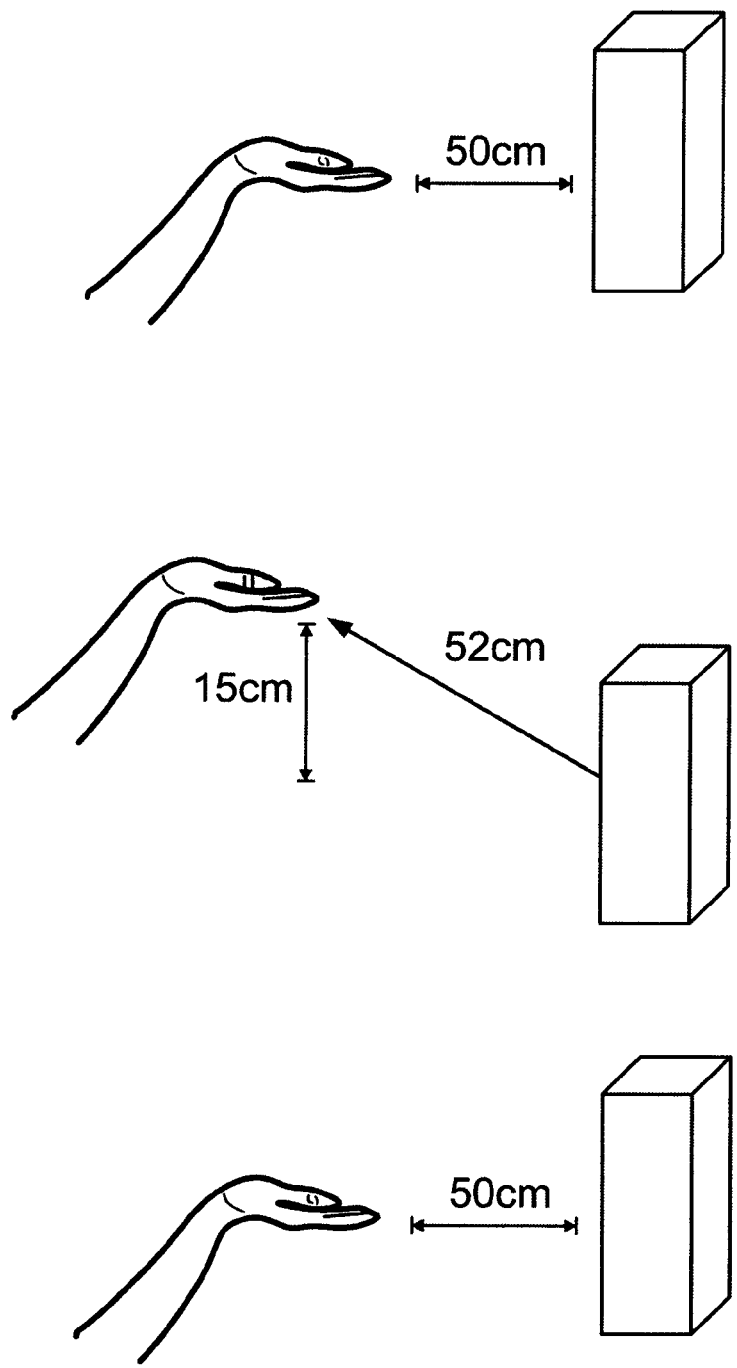
FIGS. 24A-C illustrate a still different motion gesture and the amplitude, phase and frequency response by a suitable sensor to its repetition and the single movement.
Figure 24B:
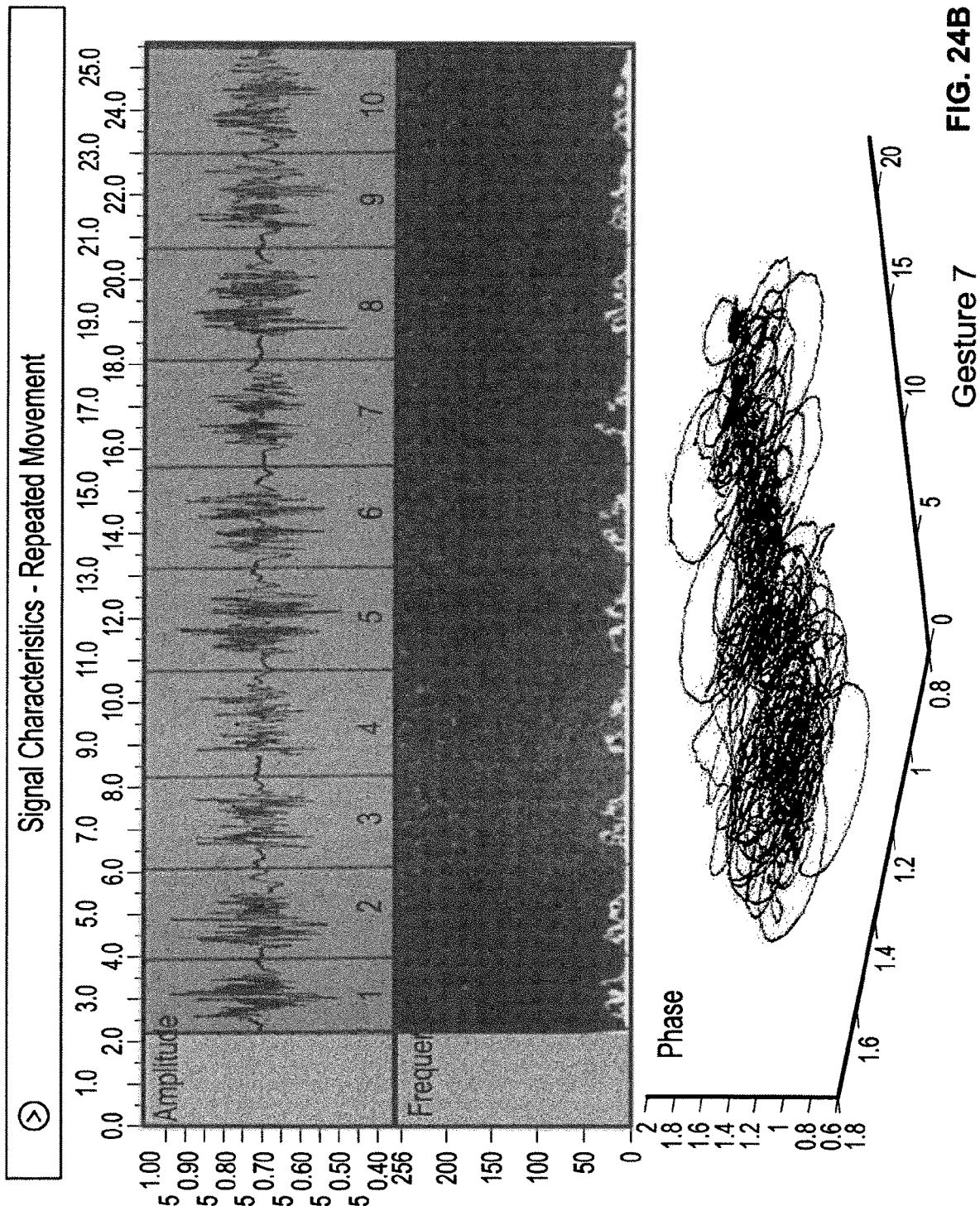
Figure 24C:
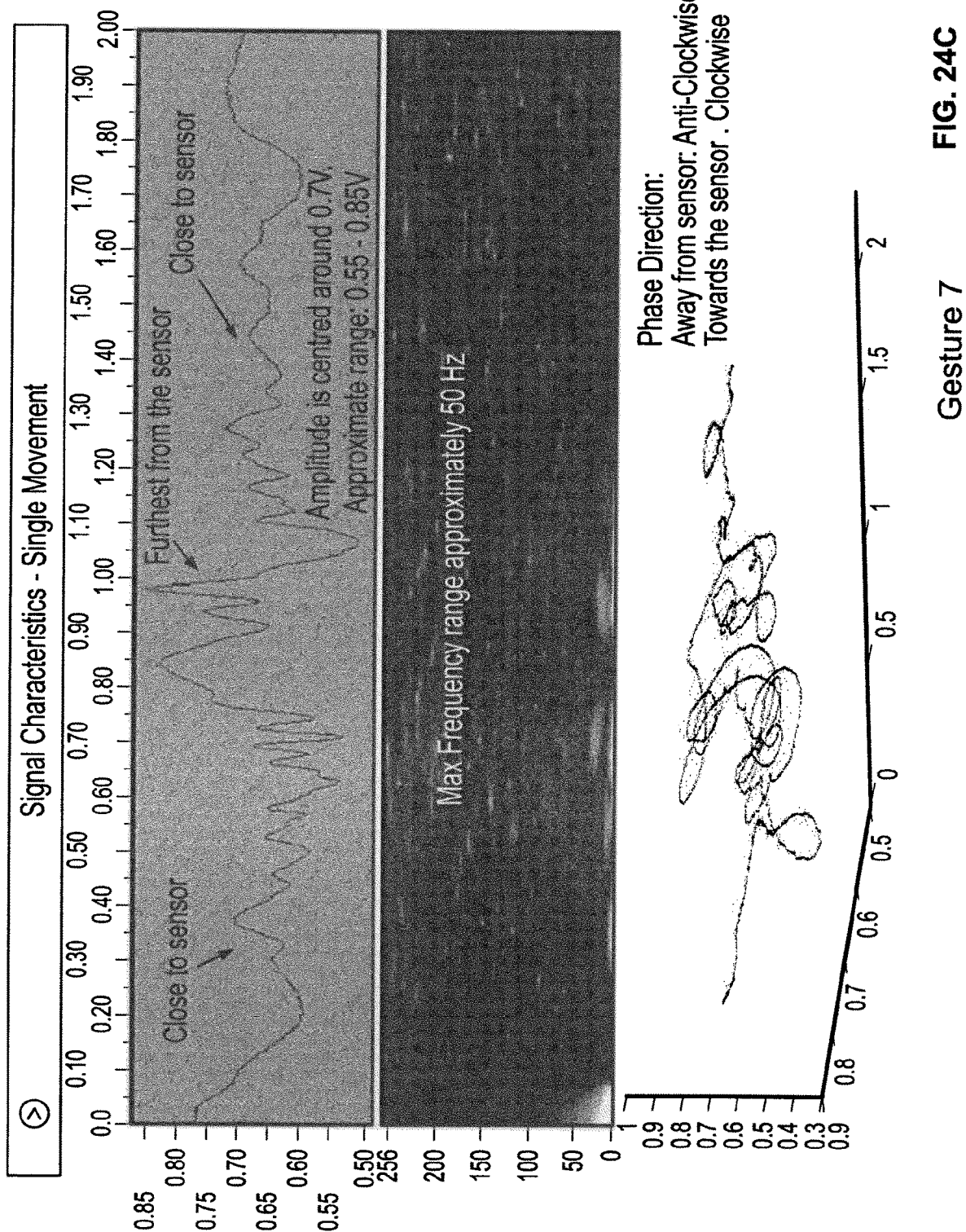

Gesture 7:

Gesture 7 may be considered in reference to FIGS. 24A-C. In this example, the sensor was positioned approximately 70 cm from the centre of the chest. The furthest point during the gross motion was approximately 52 cm from the sensor and the closest point was approximately 50 cm. As shown in FIG. 24A, the arm and hand movement begins with the arm parallel to the sensor and the palm of the hand facing upwards. The hand is then pulsed up approximately 15 cm before returning to the original position. The complete gesture took approximately 2 seconds. The motion may be performed while standing, lying or from in a sitting position.

As illustrated in FIGS. 24B (10 repetitions of gesture) and 24C (single gesture) features of any one or more of the phase, frequency and amplitude may be classified for detection of the gesture or the repeated gesture.

Rollover Movement 1

Figure 25A:
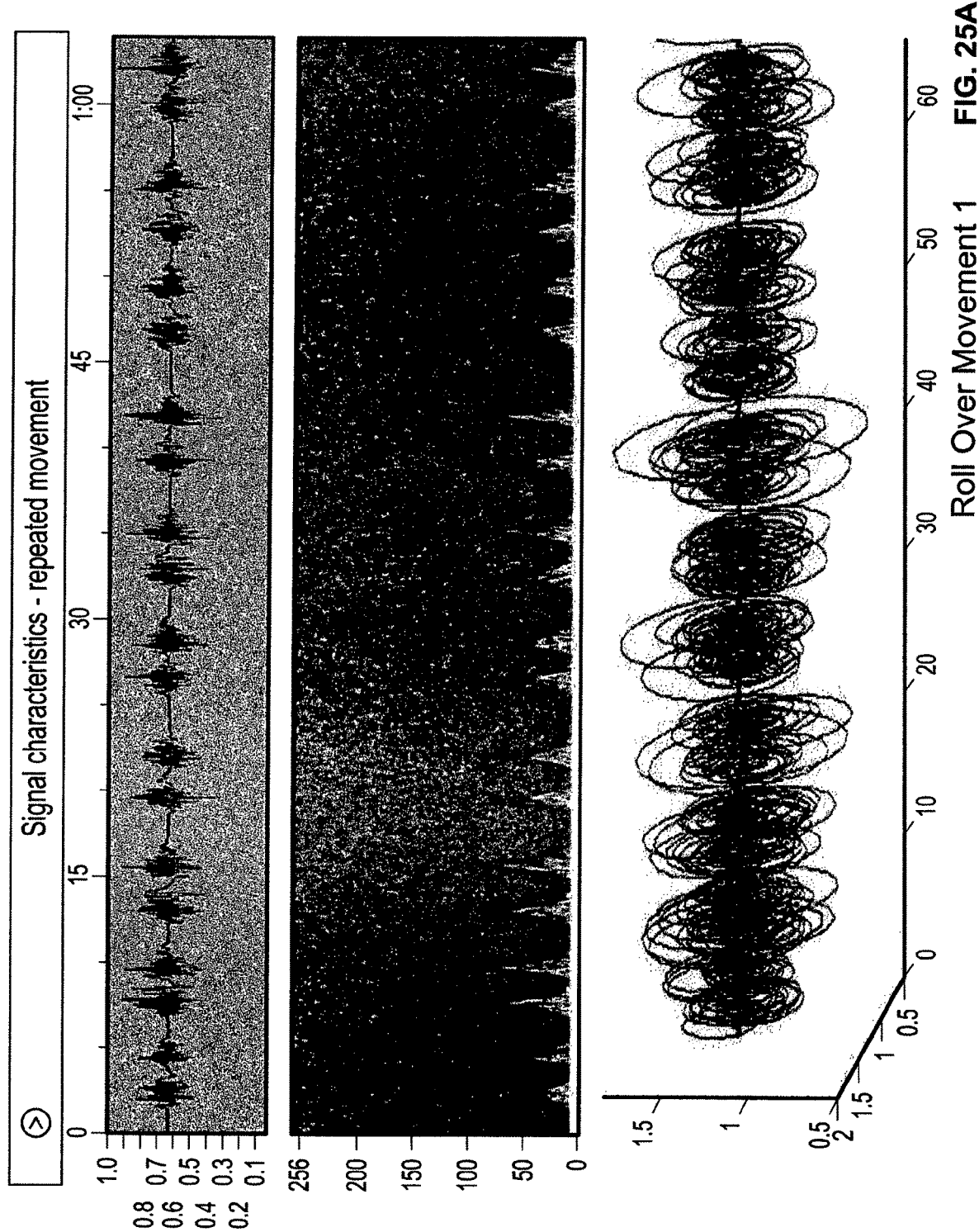
FIGS. 25A-B illustrate a rollover motion and the amplitude, phase and frequency response by a suitable sensor to its repetition and the single movement.
Figure 25B:
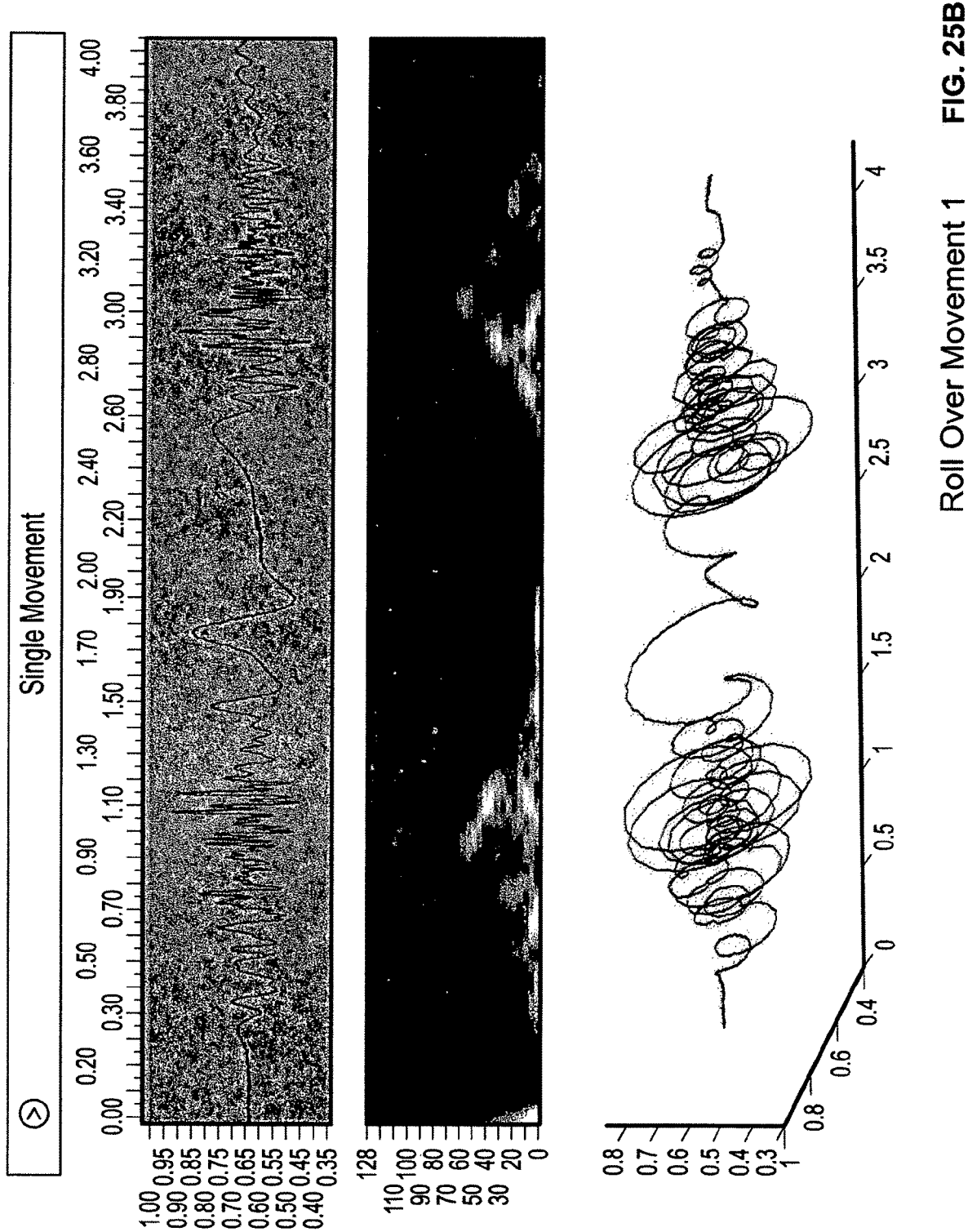

Rollover detection may be considered in reference to FIGS. 25A-B. For sleep information detection, a rollover may be taken as an indication that the person is having difficulty sleeping. In this example, the movement begins with a person on their back, for example. The person rolls onto their side towards the sensor which may take approximately 2 seconds. There may be a pause thereafter (such as about 1 second in the test example). The person then rolls away from the sensor to the initial position, which may take approximately 2 seconds. In the signal data of the figures, the complete movement takes 5 seconds (two rollovers). This is repeated 10 times in the data.

As illustrated in FIGS. 25A (10 repetitions of rollover motion) and 25B (rollover), features of any one or more of the phase, frequency and amplitude may be classified for detection of the motion or the repeated motion.

Rollover Movement 2

Rollover detection may be further considered in reference to FIGS. 26A-B. In this example, the movement begins with the subject on their back, for example. The person will then roll onto their side away from the sensor which may take approximately 2 seconds. There may be a pause thereafter (such as about 1 second in the text example). The person may then roll back towards the sensor to the initial position. This may take approximately 2 seconds. In the signal data of the figures, the complete movement takes 5 seconds (two rollovers). This is repeated 10 times in the data.

As illustrated in FIGS. 26A (10 repetitions of rollover motion) and 26B (rollover), features of any one or more of the phase, frequency and amplitude may be classified for detection of the motion or the repeated motion.

Rollover Movement 3

Figure 27A:
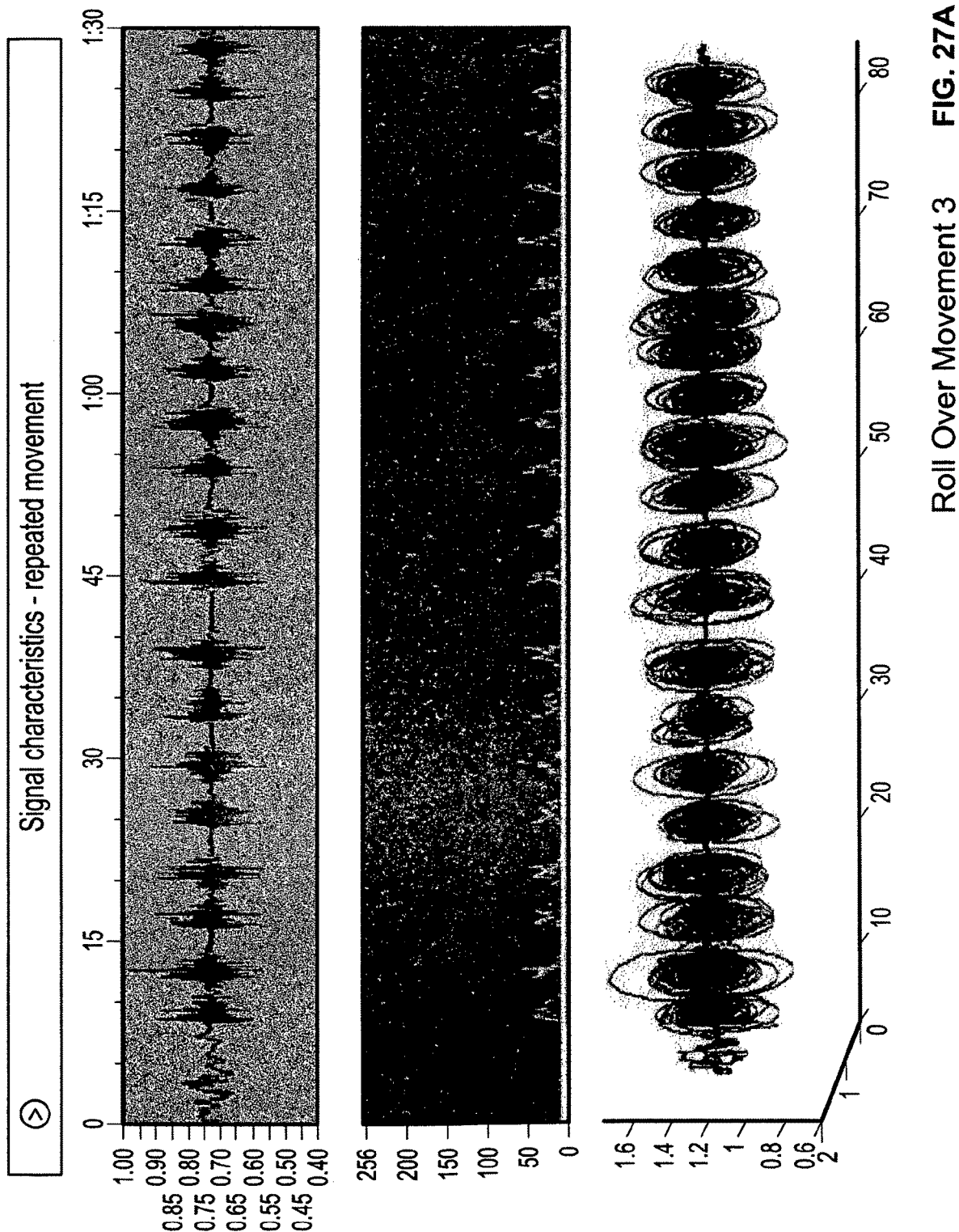

Rollover detection may be further considered in reference to FIGS. 27A-B. In this example, the movement is a little longer than that of the rollover of FIG. 26 (rollover movement 2). The movement begins with the subject on their back, for example. The person will then roll onto their front away from the sensor which may take approximately 3 seconds. There may be a pause thereafter (such as about 1 second in the text example). The person may then roll back towards the sensor to initial position. This may take approximately 3 seconds. In the signal data of the figures, the complete movement takes 7 seconds (two rollovers). This is repeated 10 times in the data.

As illustrated in FIGS. 27A (10 repetitions of rollover motion) and 27B (rollover), features of any one or more of the phase, frequency and amplitude may be classified for detection of the motion or the repeated motion.

Rollover Movement 4

Figure 28A:
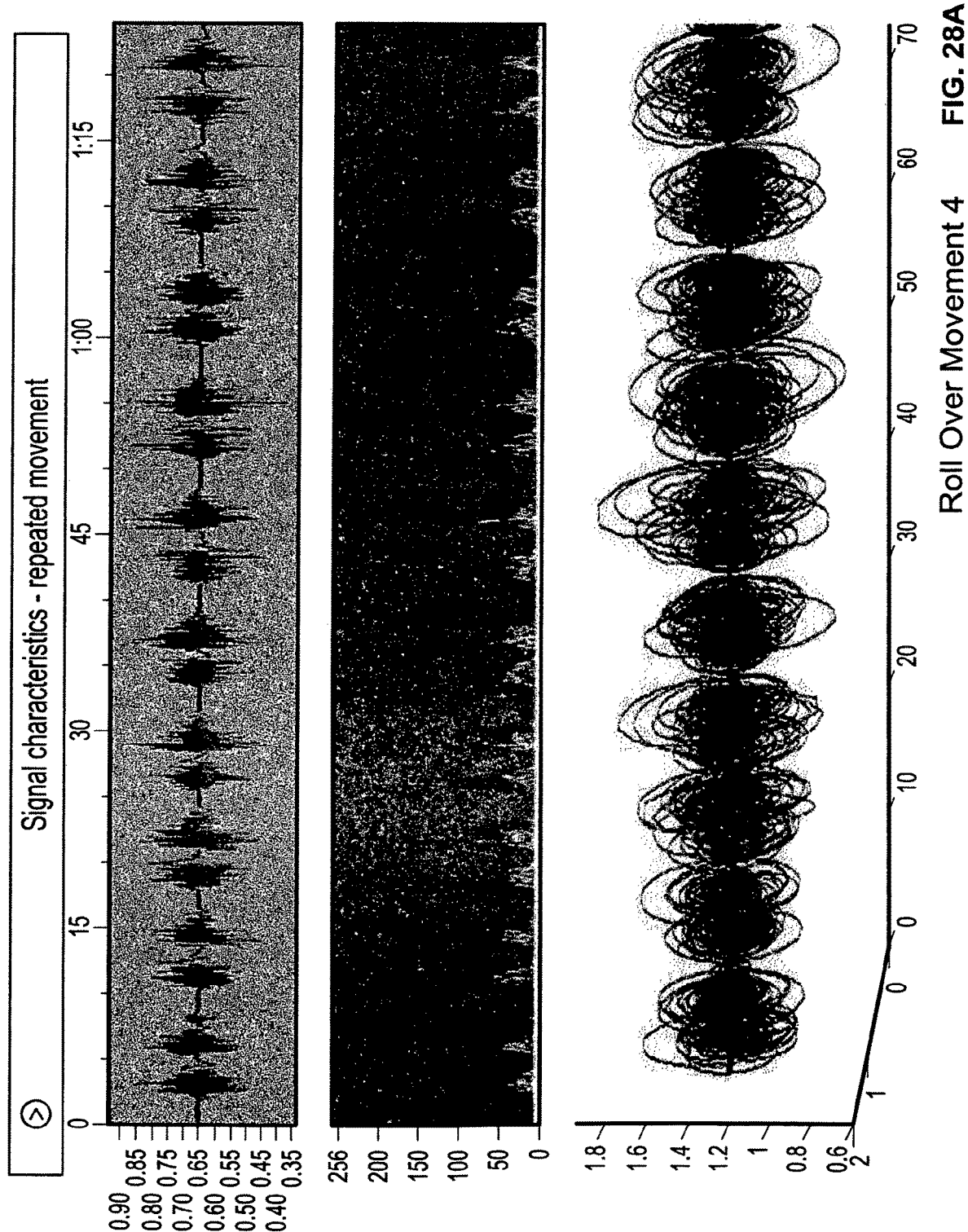
FIGS. 28A-B illustrate yet another rollover motion and the amplitude, phase and frequency response by a suitable sensor to its repetition and the single movement.
Figure 28B:
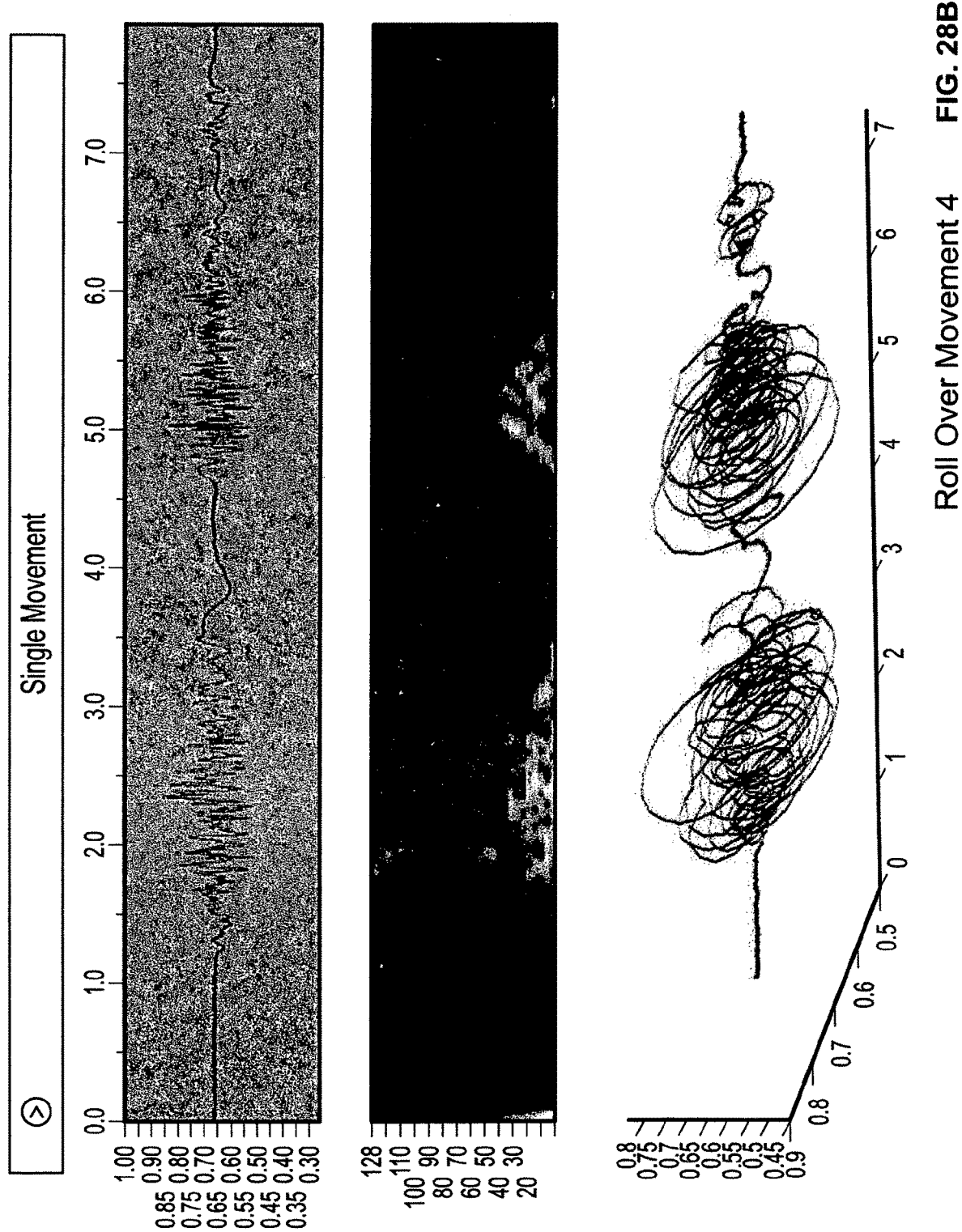
Figure 29A:
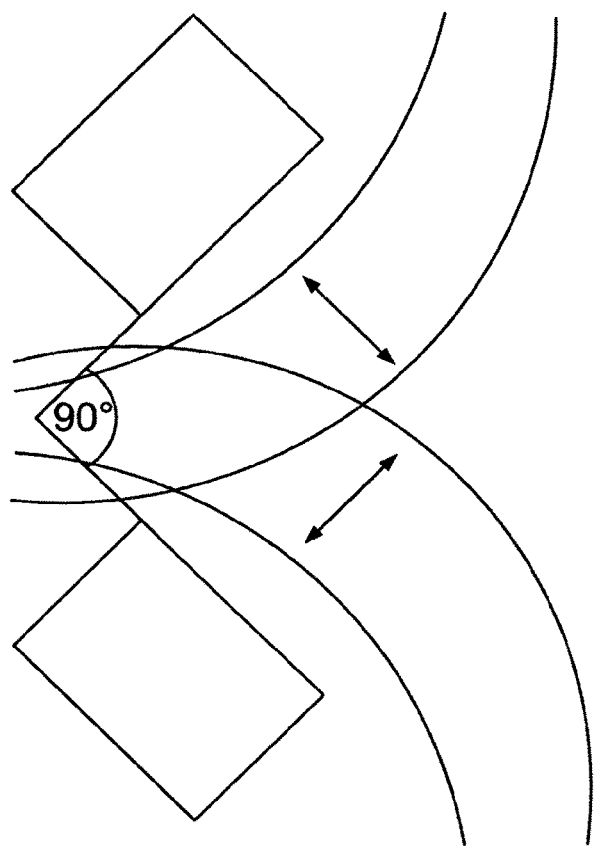
FIG. 29A illustrates maximum quadrature (I/Q) phase detection in a multi-sensor (e.g., stereo sensor system) setup. To always get maximum phase the sensors may be placed orthogonal to each other (unless the motion is in a downwards direction—this direction is not depicted in the figure).
Figure 29B:
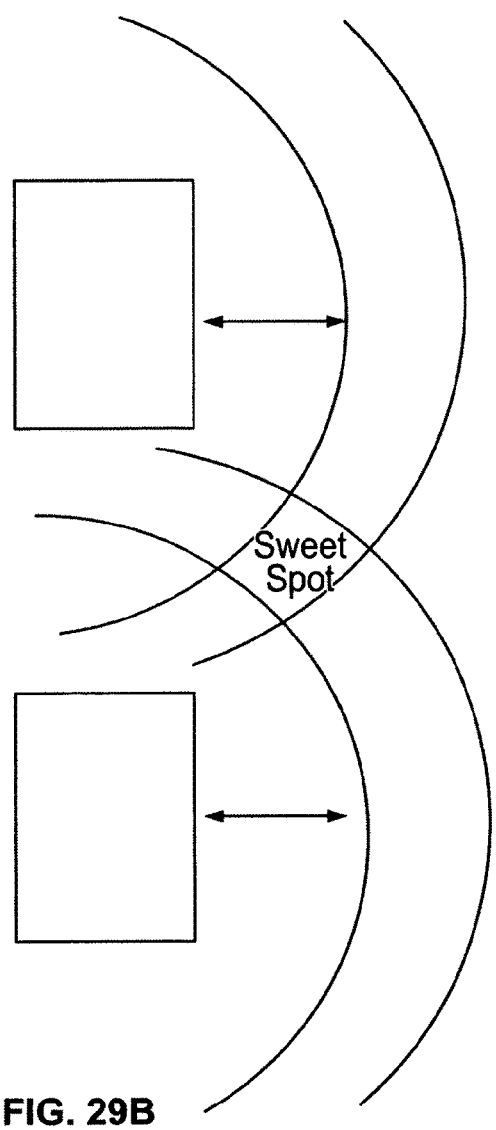
FIG. 29B illustrates another example of a multi-sensor (e.g., stereo sensor system setup). The section labelled 'sweet spot' on the figure depicts the area that is optimum focus for both sensors, due to the curved beam pattern. This shows that the sensors do not need to be orthogonal.

Rollover detection may be further considered in reference to FIGS. 28A-B. In this example, the movement is a little longer than that of the rollover of FIG. 25 (rollover movement 1). The movement begins with the subject on their back, for example. The person will then roll onto their front toward the sensor which may take approximately 3 seconds. There may be a pause thereafter (such as about 1 second in the text example). The person may then roll back away from the sensor to the initial position. This may take approximately 3 seconds. In the signal data of the figures, the complete movement takes 7 seconds (two rollovers). This is repeated 10 times in the data. As illustrated in FIGS. 27A (10 repetitions of rollover motion) and 27B (rollover), features of any one or more of the phase, frequency and amplitude may be classified for detection of the motion or the repeated motion.

In one alternative approach, a global feature may be extracted directly from the spectrogram in order to provide a reference signature. As depicted in the gesture and rollover figures, a characteristic pattern for each gesture can be seen in the colour spectrogram. Such an approach may be performed by processing or analysing the colour information in the spectrogram pixels—e.g., in a block by block or region approach. Optionally, enhancement may be performed, including edge detection and enclosing specific patterns; this can be effective to remove or reduce noise in the surrounding pixels. The colour may be processed in, for example, RBG (red green blue) or CMYK (cyan magenta yellow black) depending on the colour space; each may be treated as a separate channel. Colour intensities can be separated by intensity value (e.g., low, low-medium, medium, medium-high, high or some other combination), and then passed into a classifier, such as a neural network. For example, consider FIG. 22C and the colour spectrogram and the processing images of FIG. 30. Edge enhancement here may be directed at capturing the outline of the red blobs, and rejecting the stippled blue/purple region. The shape of the red region with yellow streaks thus provides an initial signature (template) for this gesture type, and can be used in a supervised learning classifier. The variability of multiple iterations of this gesture (movement) is shown in FIG. 22B, although the same basic shape and colour persists. This pattern can be averaged from this repeated movement, and provide a training input for this target gesture (movement).

Figure 30:
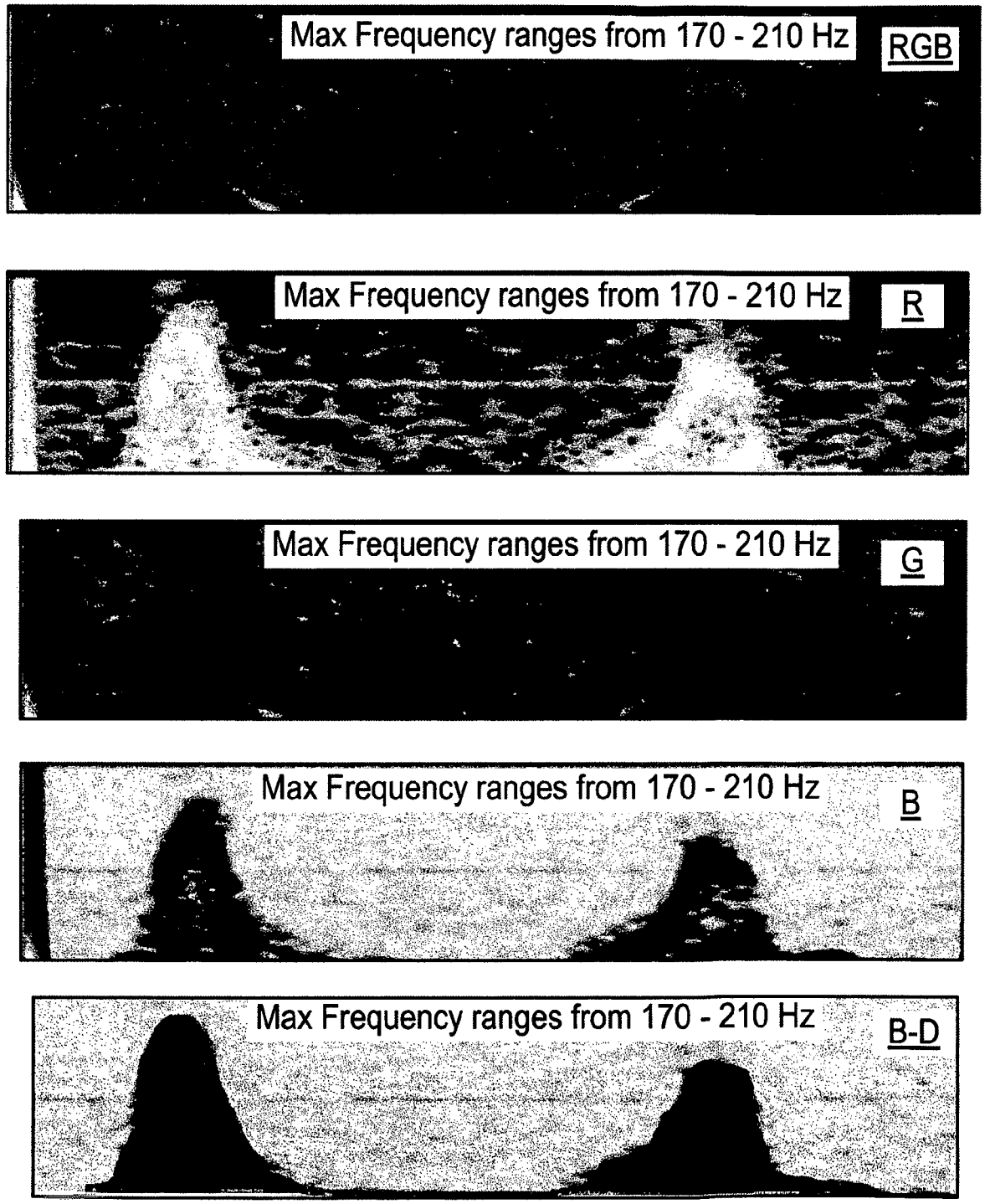
FIG. 30 illustrates processing of image data by splitting the colour data from a spectrogram into RGB channels and selecting main blob areas.

FIG. 30 shows images. From top to bottom panel: the top panel contains RGB colour space channels, the second panel depicts R (red) channel only, the third depicts G (green), the fourth B (blue) and the bottom B-D is the blue channel with blob detection applied to the intensity values, and shifting slightly to the left to remove the frequency component at the very left (shown in panels 1-4). The maximum frequency ranges from 170 Hz (rightmost "blob") to 210 Hz (leftmost "blob") Thus, as illustrated in reference to FIG. 30 (second image up from the bottom), the image data may be processed to split (see FIG. 22[C] from the original (top)) the colour data of the top image RGB into any one or more of the discrete red, green, blue color channels (top-middle image R (red), middle image G (green) and bottom two images B (blue) respectively) channels and selecting main blob areas. To the human eye, clearest signature is evident in the Blue channel (bottom); i.e., consider the black region (ignoring the vertical stripe to the left of the image). The bottom image B-D illustrates overlaid blob detection of the isolated blue channel. Such splitting/color separation and blob detection may be performed by suitable algorithm(s) of one or more processors of the system, such as part of a process involving feature detection and/or classification as described in more detail herein.

Multiple RF Sensors (e.g., Stereo Sensor System):

For an exemplar single RF sensor, the I and Q phase can be detected as the user moves towards or away from it. Movement perpendicular to a single sensor (across the face of the sensor) may have a much smaller relative phase change (e.g., a movement in an arc across the sensor's detection plane will have a very low or no phase change measurable). It is possible that additional sensors (e.g., a system with a second (and subsequent) sensor(s) placed adjacent to the first sensor (e.g., at an angle from each other)) can be employed to also detect signals of objects moving in and out. For example, a second sensor, may be positioned in the arc of the first sensor (e.g., the sensor might be at 45 degrees to the first sensor or orthogonal (at 90 degrees) or other appropriate differentiated angle with respect to first sensor). Thus, the effective stereo sensor system may more efficiently detect and characterise movement across various detection planes corresponding to the sensors (e.g., a movement perpendicular to the first sensor may be more clearly characterized by analysis of the signal of the second sensor). In such a case, the movement/gesture classification may take into account the signal information from both sensors (e.g., features derived from the phase output from both sensors). Such a system may for example return a different control signal based on the direction of motion in this manner. For a shaving analysis, the quadrant of the face (or other part of the body) could be determined. For a gaming implementation, a specific localised movement could be determined.

Thus, two sensors can work cooperatively as a "stereo" system to detect and recognize gestures in two dimensions (2D), and three sensors can be used for identifying three dimensional characteristics (3D) of a gesture movement, using for example, range gated RF sensors. Thus, a single gesture may be characterized by obtaining detection signals from multiple sensors. For the two sensor 2-dimension case (i.e., 2D), the I/Q signals from each of a sensor1 and sensor2 (differential in I1, I2, Q1, Q2 for two sensor case—left and right), can be analyzed by a processor. The resulting difference in amplitude and phase provides an "x", "y" output. In some cases, three sensors may be implemented in a cooperative system to add the "z" axis, in order to provide fine grained three-dimensional gesture recognition data in the resulting sensor field. In such as case, the differentials of I1, I2, I3, Q1, Q2, Q3 may be evaluated by a processor with the signals from the three sensor case to discriminate a single gesture. In some embodiments, a maximum phase may be obtained by placing at least two of the three sensors to be orthogonal to each other.

In some versions, a multi-ray antenna (phase array antenna) may be implemented on one sensor if the antennas are separated. This may eliminate the need for a second sensor.

In some cases, the RF sensor motion signals may, for example, be up-converted to audio frequencies such that a gesture may be detected (recognised) by a specific audio signature (e.g., by producing a sound from a speaker with the upconverted signals). This could allow a human to distinguish different types of gesture, or to utilise known audio recognition approaches to augment the classification and/or device training.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. For example, whilst the disclosure has described the detection of movements such as hand/arm based gestures and roll-overs, the same principal is applicable to other large scale motions, such as user moving between a lying and a sitting position in bed (and vice versa), reaching for a specific target (a table lamp, or a respiratory apparatus) etc.

It will further be understood that any reference herein to subject matter known in the field does not, unless the contrary indication appears, constitute an admission that such subject matter is commonly known by those skilled in the art to which the present technology relates.

PARTS LIST

Detection apparatus 100
Read step 1502
Feature Generation step 1504
Pre-testing setup step 1505
Training setup step 1506
Classification step 1507
Training classify step 1508
Video performance step 1509
Video performance step 1510
Check step 1512

The invention claimed is:

1. A radio frequency motion sensing apparatus comprising:
   a radio frequency transmitter configured to emit radio frequency signals;
   a receiver configured to receive reflected ones of the emitted radio frequency signals,
   a motion channel circuit configured to process the received reflected ones of the emitted radio frequency signals and produce motion output signals; and
   a processor configured to evaluate the motion output signals and identify a motion based on phase of the motion output signals, wherein the processor is configured to evaluate the motion output signals and identify the motion by evaluation of variation in a phase difference between I and Q signals, wherein the processor is configured to generate a direction change signal from the variation, the direction change signal representing a plurality of direction changes from the variation in phase difference.

2. The apparatus of claim 1 wherein the identified motion comprises at least one of hand gesture, an arm gesture or a combined hand and arm gesture.

3. The apparatus of claim 1 wherein the identified motion comprises a rollover motion.

4. The apparatus of claim 1 wherein the identified motion comprises an activity.

5. The apparatus of claim 4 wherein the identified motion comprises a shaving activity.

6. The apparatus of claim 1 wherein the motion output signals comprise in phase and quadrature phase signals.

7. The apparatus of claim 1 wherein the emitted radio frequency signals comprise pulsed radio frequency oscillating signals.

8. The apparatus of claim 1 wherein the motion channel circuit comprises a bandpass filter.

9. The apparatus of claim 1 wherein the apparatus demodulates the received reflected ones of the emitted radio frequency signals with signals representing the emitted radio frequency signals.

10. The apparatus of claim 1 wherein the apparatus calculates time difference between the emitted radio frequency signals and the received reflected ones of the emitted radio frequency signals and identifies the motion based on the calculated time difference.

11. The apparatus of claim 1 wherein the motion channel circuit comprises an antialiasing filter.

12. The apparatus of claim 1 wherein the processor is configured to classify a motion based on a plurality of features calculated from any two of amplitude, phase and frequency of the motion output signals.

13. The apparatus of claim 1 wherein the processor is configured to classify or identify a motion based on a duration calculated with any one or more of amplitude, phase and frequency of the motion output signals.

14. The apparatus of claim 12 wherein the processor is configured to calculate the plurality of features from each of the amplitude, phase and frequency of the motion output signals.

15. The apparatus of claim 12 wherein the plurality of features comprise a determined duration derived from analysis of any one or more of the amplitude, phase and frequency of the motion output signals.

16. The apparatus of claim 15 wherein the calculated plurality of features comprise one or more of:
(a) a frequency characteristic derived from stopped frequency through a gesture in motion up to some maximum frequency, then back to stopped again;
(b) a time and frequency analysis of the motion output signals comprising any of short time Fourier transform, peak and harmonic tracking and/or channel processing of an I and/or Q channel(s);
(c) a phase characteristic comprising any of: a phase difference between I and Q signals and an evaluation of a repetitive signal within a certain number of standard deviations of a mean of characteristic change;
(d) an amplitude characteristic comprising any of: peak and trough detection, zero crossing detection, and envelope of signal detection; and
(e) a skewness, kurtosis, spread in frequency, phase, amplitude, mean, and/or standard deviation.

17. The apparatus of claim 14 wherein the processor is configured to compare the calculated plurality of features to one or more thresholds.

18. The apparatus of claim 1 wherein the processor is configured to identify the motion by selecting one from a plurality of predetermined motions.

19. The apparatus of claim 1 wherein the processor is configured to count a number of occurrences of the identified motion.

20. The apparatus of claim 1 wherein the processor is further configured to generate a control signal for operation of a device based on the identified motion.

21. The apparatus of claim 1 wherein the processor is further configured to generate different control signals for different operations of a device based on different identified motions.

22. The apparatus of claim 1 wherein the processor is configured to evaluate the motion output signals and identify a motion based on motion output signals from a plurality of sensors.

23. The apparatus of claim 22 wherein the plurality of sensors comprises a first sensor and a second sensor, wherein the processor evaluates I and Q signals from the first sensor and the second sensor to identify the motion.

24. The apparatus of claim 23 wherein the processor determines an I differential and a Q differential of the I and Q signals from the first sensor and the second sensor.

25. The apparatus of claim 22 wherein the plurality of sensors comprises a first sensor, second sensor and a third sensor, wherein the processor evaluates I and Q signals from the first sensor, the second sensor and the third sensor to identify the motion.

26. The apparatus of claim 25 wherein at least two of the first sensor, second sensor and third sensor are positioned to be orthogonal to each other.

27. The apparatus of claim 23, wherein the evaluated I and Q signals are used by the processor to identify movement characteristics in more than one dimension.

28. The apparatus of claim 1, wherein the processor is configured to extract one or more of the following: velocity, change in velocity, distance, change in distance, direction and change in direction.

29. A method for radio frequency motion sensing comprising:
with a radio frequency transmitter, emitting radio frequency signals;
with a receiver, receiving reflected ones of the emitted radio frequency signals,
processing the received reflected ones of the emitted radio frequency signals to produce motion output signals with a motion channel circuit; and
in a processor, evaluating the motion output signals and identifying a motion based on phase of the motion output signals, wherein the evaluating the motion output signals and identifying the motion comprises evaluation of variation in a phase difference between I and Q signals, wherein the processor is configured to generate a direction change signal from the variation, the direction change signal representing a plurality of direction changes detected from the variation in phase difference.

30. The method of claim 29 wherein the identified motion comprises any one of hand gesture, an arm gesture and a combined hand and arm gesture.

31. The method of claim 29 wherein the identified motion comprises a rollover motion.

32. The method of claim 29 wherein the identified motion comprises an activity.

33. The method of claim 32 wherein the identified motion comprises a shaving activity.

34. The method of claim 29 wherein the motion output signals comprise in phase and quadrature phase signals.

35. The method of claim 29 wherein the emitted radio frequency signals comprise pulsed radio frequency oscillating signals.

36. The method of claim 29 wherein the motion channel circuit comprises a bandpass filter.

37. The method of claim 29 further comprising demodulating the received reflected ones of the emitted radio frequency signals with signals representing the emitted radio frequency signals.

38. The method of claim 29 further comprising calculating time difference between the emitted radio frequency signals and the received reflected ones of the radio frequency signals and identifying the motion based on the calculated time difference.

39. The method of claim 29 wherein the motion channel circuit comprises an antialiasing filter.

40. The method of claim 29, further comprising, with the processor classifying a motion based on a plurality of features calculated from any two of amplitude, phase and frequency of the motion output signals.

41. The method of claim 29 wherein the processor classifies or identifies a motion based on a duration calculated with any one or more of amplitude, phase and frequency of the motion output signals.

42. The method of claim 40 further comprising calculating in the processor the plurality of features from each of the amplitude, phase and frequency of the motion output signals.

43. The method of claim 40 wherein the plurality of features comprise a determined duration derived from analysis of any one or more of the amplitude, phase and frequency of the motion output signals.

44. The method of claim 42 wherein the calculated plurality of features comprise one or more of:
(a) a frequency characteristic derived from stopped frequency through a gesture in motion up to some maximum frequency, then back to stopped again;
(b) a time and frequency analysis of the motion output signals including any of a short time Fourier transform, peak and harmonic tracking, and processing of I and/or Q channel(s);
(c) a phase characteristic including any of a phase difference between I and Q signals or an evaluation of a repetitive signal within a certain number of standard deviations of a mean of characteristic change;
(d) an amplitude characteristic including any of a peak and trough detection, a zero crossing detection, an envelope of signal detection; and
(e) a skewness, kurtosis, spread in frequency, phase, amplitude, mean, and/or standard deviation.

45. The method of claim 42 further comprising, in the processor, comparing the calculated plurality of features to one or more thresholds.

46. The method of claim 29, further comprising, in the processor, identifying the motion by selecting one from a plurality of predetermined motions.

47. The method of claim 29 further comprising, in the processor, counting a number of occurrences of the identified motion.

48. The method of claim 29 further comprising, with the processor, generating a control signal for operation of a device based on the identified motion.

49. The method of claim 29 further comprising with the processor generating different control signals for different operations of a device based on different identified motions.

50. The method of claim 29 wherein the processor evaluates the motion output signals from a plurality of sensors and identifies a motion based on the evaluated motion output signals.

51. The method of claim 50 wherein the plurality of sensors comprises a first sensor and a second sensor, wherein the processor evaluates I and Q signals from the first sensor and the second sensor to identify the motion.

52. The method of claim 51 wherein the processor determines an I differential and a Q differential of the I and Q signals from the first sensor and the second sensor.

53. The method of claim 50 wherein the plurality of sensors comprises a first sensor, a second sensor and a third sensor, wherein the processor evaluates I and Q signals from the first sensor, the second sensor and the third sensor to identify the motion.

54. The method of claim 53 wherein at least two of the first sensor, the second sensor and the third sensor are positioned to be orthogonal to each other.

55. The method of claim 49, wherein the evaluated I and Q signals are used by the processor to identify movement characteristics in more than one dimension.

56. The method of claim 29, the method comprising extracting, with the processor, one or more of the following: velocity, change in velocity, distance, change in distance, direction and change in direction.

57. The method of claim 29 wherein the evaluating the motion output signals and identifying a motion is based on frequency of the motion output signals.

58. The method of claim 29 wherein the evaluating the motion output signals and identifying a motion is based on amplitude of the motion output signals.

59. The method of claim 29 wherein radio frequency signals emitted are pulsed continuous wave radio frequency signals.

60. The method of claim 29 wherein the motion output signals are produced from demodulating the received reflected ones of the radio frequency signals by the emitted radio frequency signals.

61. The method of claim 29 further comprising range gating of the radio frequency signals.

62. The method of claim 29 wherein the evaluating the motion output signals and identifying the motion based on the phase difference between I and Q signals comprises evaluation of a phasor determined from the I and Q signals.

63. The method of claim 29 wherein evaluating the motion output signals and identifying the motion is based on a phase difference between the emitted radio frequency signals and the received reflected ones of the radio frequency signals.

64. The method of claim 29 wherein further comprising detecting physiological characteristics of a user.

65. The apparatus of claim 1 wherein the processor is configured to evaluate the motion output signals and identify the motion based on frequency of the motion output signals.

66. The apparatus of claim 1 wherein the processor is configured to evaluate the motion output signals and identify the motion based on amplitude of the motion output signals.

67. The apparatus of claim 1 wherein radio frequency signals emitted are pulsed continuous wave radio frequency signals.

68. The apparatus of claim 1 wherein the motion output signals are produced from demodulating the received reflected ones of the radio frequency signals by the emitted radio frequency signals.

69. The apparatus of claim 1 wherein the radio frequency motion sensing apparatus is configured to range gate the radio frequency signals.

70. The apparatus of claim 1 wherein the processor is configured to evaluate the motion output signals and identify the motion based on the phase difference between I and Q signals by evaluation of a phasor determined from the I and Q signals.

71. The apparatus of claim 1 wherein the processor is configured to evaluate the motion output signals and identify the motion based on a phase difference between the emitted radio frequency signals and the received reflected ones of the radio frequency signals.

72. The apparatus of claim 1 wherein the radio frequency motion sensing apparatus is further configured to detect physiological characteristics of a user.

73. The apparatus of claim 1 wherein the processor is further configured to generate the direction change signal by applying hysteresis to avoid a flipping state on fold-over.

74. The apparatus of claim 73 wherein the processor is further configured to identify the motion by differentiating the direction change signal.

75. The method of claim 29 wherein the processor generates the direction change signal by applying hysteresis to avoid a flipping state on fold-over.

76. The method of claim 75 wherein the processor identifies the motion by differentiating the direction change signal.

* * * * *